United States Patent
Sauder et al.

(10) Patent No.: US 9,894,835 B2
(45) Date of Patent: *Feb. 20, 2018

(54) STALK SENSOR APPARATUS, SYSTEMS, AND METHODS

(71) Applicant: The Climate Corporation, San Francisco, CA (US)

(72) Inventors: Timothy A. Sauder, Tremont, IL (US); Derek A. Sauder, Tremont, IL (US); Justin L. Koch, Deer Creek, IL (US); Troy L. Plattner, Goodfield, IL (US); David Huber, Bloomington, IL (US)

(73) Assignee: The Climate Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/137,989

(22) Filed: Apr. 25, 2016

(65) Prior Publication Data

US 2016/0235002 A1 Aug. 18, 2016

Related U.S. Application Data

(63) Continuation of application No. 14/360,209, filed as application No. PCT/US2012/066279 on Nov. 21, 2012, now Pat. No. 9,322,629.

(Continued)

(51) Int. Cl.
*A01D 41/127* (2006.01)
*A01D 45/02* (2006.01)
*A01B 79/00* (2006.01)
*A01D 43/00* (2006.01)
*G01B 5/10* (2006.01)
*A01D 75/00* (2006.01)
*G01B 21/10* (2006.01)
*G01N 33/00* (2006.01)
*G01S 19/42* (2010.01)

(52) U.S. Cl.
CPC .......... *A01D 41/127* (2013.01); *A01B 79/005* (2013.01); *A01D 43/00* (2013.01); *A01D 45/021* (2013.01); *A01D 75/00* (2013.01); *G01B 5/10* (2013.01); *G01B 21/10* (2013.01); *G01N 33/0098* (2013.01); *G01S 19/42* (2013.01); *G01B 2210/00* (2013.01)

(58) Field of Classification Search
CPC .......................... A01B 79/005; A01D 41/1271; A01D 41/127; A01D 43/00; A01D 75/00; A01D 45/021; G01B 5/10; G01B 21/10; G01B 2210/00; G01N 33/0098; G01S 19/42
USPC ....... 56/10.2 A–10.2 F, 10.2 R; 701/50, 408, 701/538
See application file for complete search history.

(56) References Cited

U.S. PATENT DOCUMENTS 5,878,561 A  3/1999  Gunn
6,073,427 A  6/2000  Nichols
(Continued)

FOREIGN PATENT DOCUMENTS

GB   2432096 A   5/2007

OTHER PUBLICATIONS

European Search Report, issued Jul. 2, 2015, pp. 1-5.

*Primary Examiner* — Robert E Pezzuto
(74) *Attorney, Agent, or Firm* — Hickman Palermo Becker Bingham LLP; Malgorzata A. Kulczycka

(57) ABSTRACT

Systems, methods and apparatus for detecting stalks processed by a combine harvester, for measuring stalk diameters, and for displaying harvest metrics and yield data to a user based on stalk locations and stalk diameters.

20 Claims, 47 Drawing Sheets

Related U.S. Application Data

(60) Provisional application No. 61/562,932, filed on Nov. 22, 2011.

(56) References Cited

U.S. PATENT DOCUMENTS

| | | |
|---|---|---|
| 6,185,990 B1 | 2/2001 | Missotten et al. |
| 6,525,276 B1 | 2/2003 | Vellidus et al. |
| 9,322,629 B2 | 4/2016 | Sauder et al. |
| 2002/0173893 A1 | 11/2002 | Blackmore et al. |
| 2010/0010667 A1 | 1/2010 | Sauder et al. |

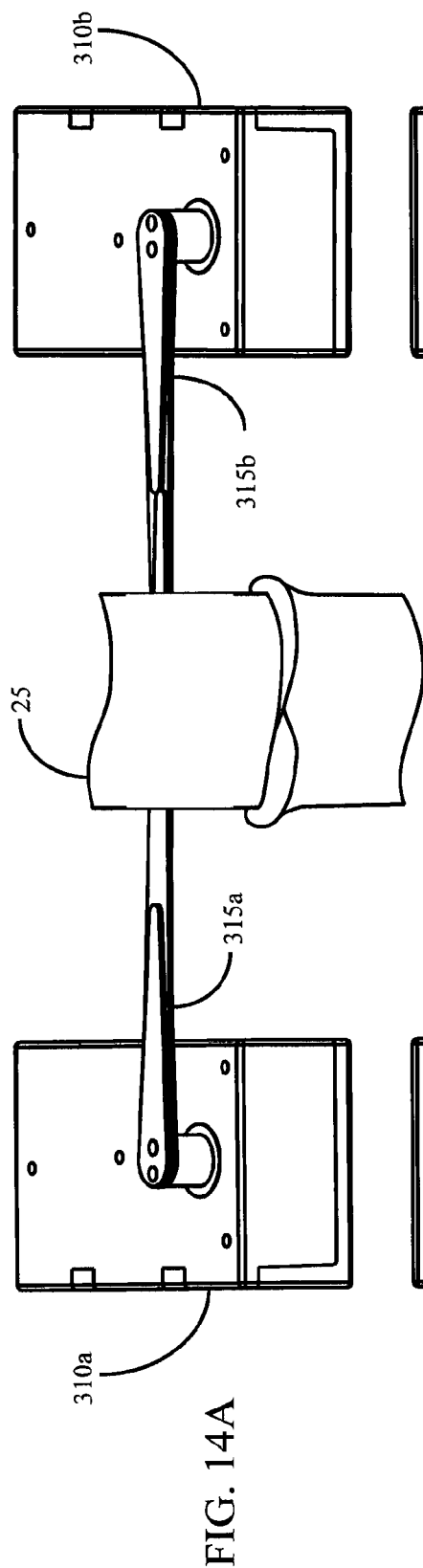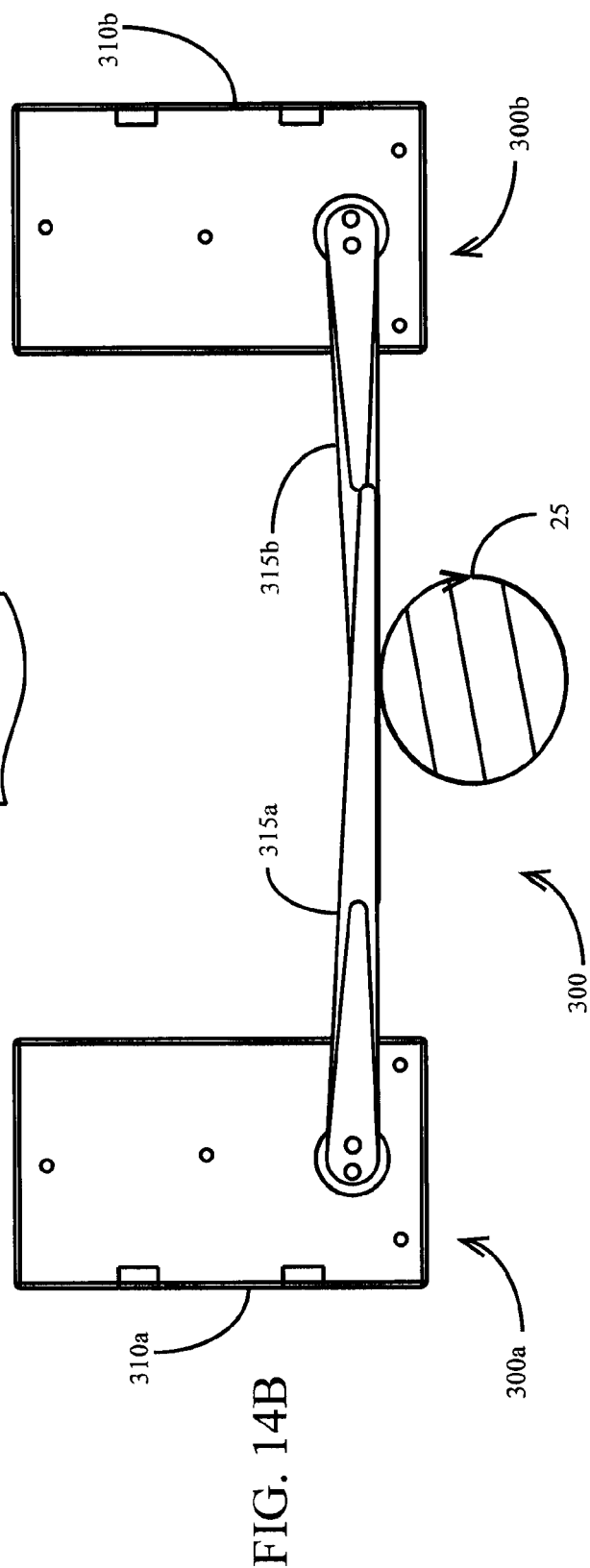
FIG. 14A
FIG. 14B

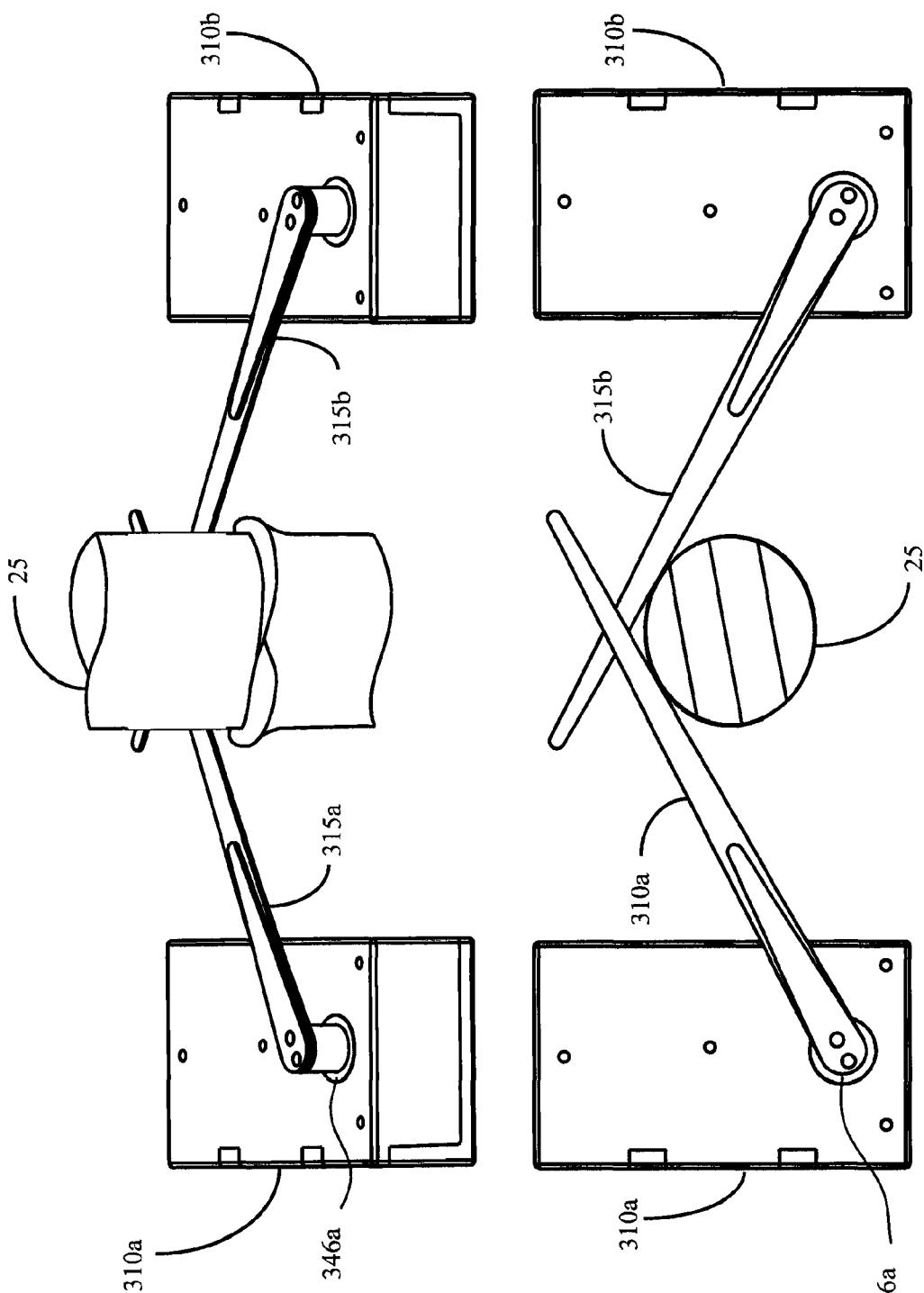

Row 1 Details

| Planter Row | Ear Count | Emergence | Setup |
|---|---|---|---|
| 12 | 25.5 ears/acre | 96.3% | Overview |

Population
Actual  As Planted
28.9   30.0

Stalk Width
Current
.75 inches  94% of full-ear
Field Ave  Full-Ear
.77 in    .8 in

Current Ears
Full-Ear  74%
Half-Ear  16%
No-Ear    10%

Row Compare

Row Visual

Economic Loss
$2.51
Loss Correlation
[Tire Tracks] [Margin] [GC]

Stalk Variation
.07  9%
inches  of mean

Row Yield Contribution
115%

Back

Good Spacing
Actual  As Planted
92.4%   95.2%
Skips: 0.3%
Doubles: 0.2%

FIG. 29

| Overview | | Setup |
|---|---|---|
| Population As Planted<br>Actual 33.0<br>32.1<br>High: 2 Low: 1<br>33.4 29.8 | Stalk Width<br>Current<br>.75 94% of full-ear<br>inches<br>Average Full-Ear<br>.77 in .8 in | Emergence<br>98%<br>Low: 4<br>88% | Row Details |
| | Yield<br>Total High: 2 Low: 4<br>197 122% 64% | Current Ears<br>Full-Ear 78%<br>Half-Ear 13%<br>No Ear 9% | Row Compare |
| Economic Loss<br>$2.87<br>Tire Tracks \| GC \| Margin<br>High: 4 Low: 2<br>$3.14 $1.27 | Stalk Variation<br>.07 9%<br>inches of mean | | Row Visual |
| | | | Back |

FIG. 37

STALK SENSOR APPARATUS, SYSTEMS, AND METHODS

CROSS-REFERENCE TO RELATED APPLICATIONS

This is a continuation of U.S. patent application Ser. No. 14/360,209, filed May 22, 2014 which is a national stage entry of International Application No. PCT/US2012/066279, filed Nov. 21, 2012, which claims the benefit of U.S. Provisional Application No. 61/562,932, filed Nov. 22, 2011

BRIEF DESCRIPTION OF THE DRAWINGS

FIG. 14A is a front perspective view of the stalk sensor of FIG. 12 interacting with a stalk.
FIG. 14B is a top view of the stalk sensor of FIG. 12 interacting with a stalk.
FIG. 15A is a front perspective view of the stalk sensor of FIG. 12 interacting with a stalk.
FIG. 15B is a top view of the stalk sensor of FIG. 12 interacting with a stalk.
FIG. 29 is an embodiment of a monitor screen display for reporting row-specific harvest data.
FIG. 37 is an embodiment of a monitor screen display for reporting harvest data.

DESCRIPTION

Figure 1:
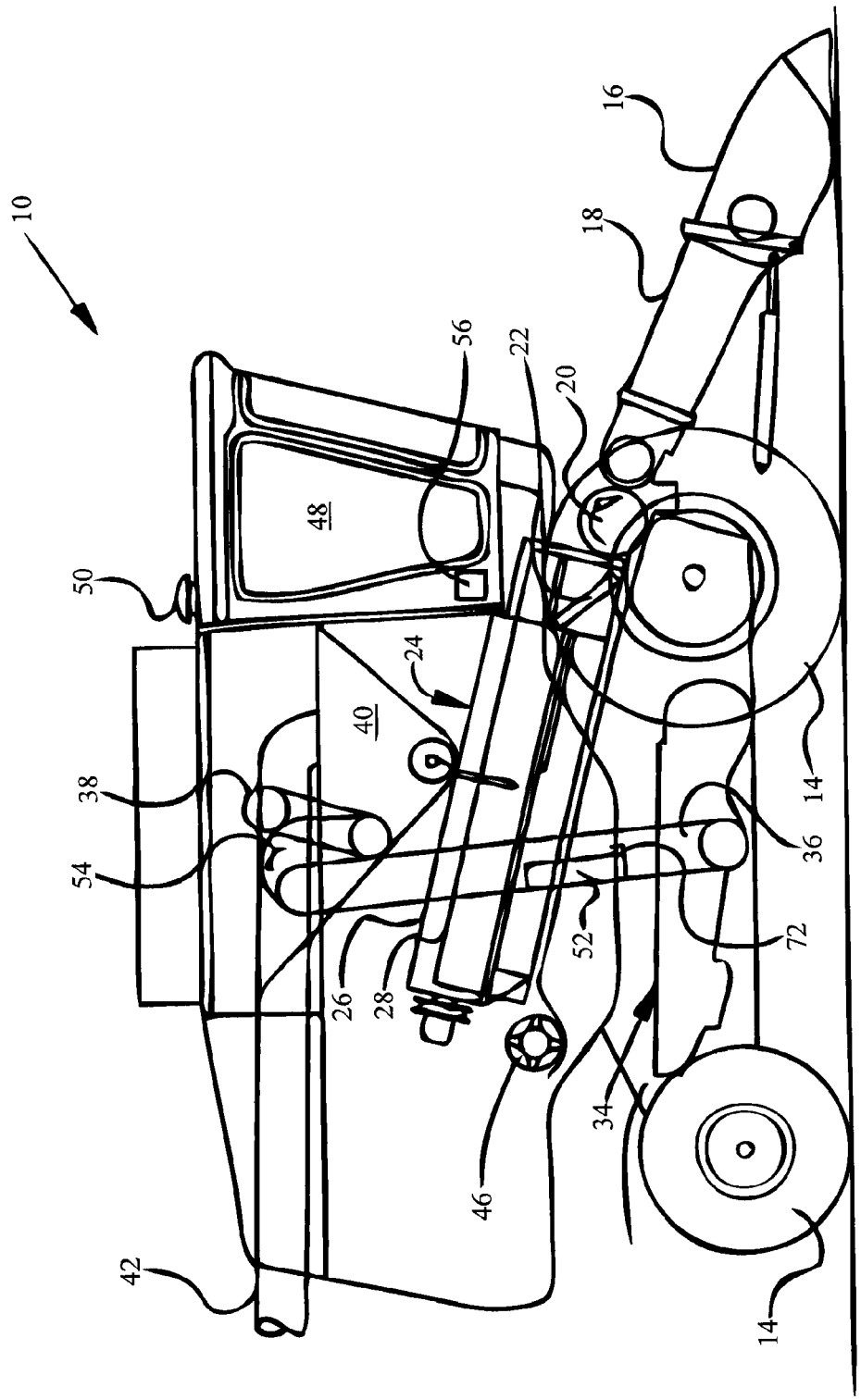
FIG. 1 is a side elevation view of a combine harvester.

Referring now to the drawings, wherein like reference numerals designate identical or corresponding parts throughout the several views, FIG. 1 illustrates a prior art agricultural combine 10 which is supported and propelled by ground engaging wheels 14. Although the combine 10 is illustrated as being supported and propelled on ground engaging wheels 14 it can also be supported and propelled by full tracks or half tracks. A harvesting assembly 16 is used to gather crop and to conduct it to a feederhouse 18. The crop is conducted by the feederhouse 18 to a beater 20. The beater 20 guides the crop upwardly through an intake transition region 22 to a rotary threshing and separating assembly 24. In addition to rotary type combines such as that illustrated in FIG. 1, the prior art includes conventional combines having a transverse threshing cylinder and straw walkers or combines having a transverse threshing cylinder and rotary separator rotors.

The rotary threshing and separating assembly 24 comprises a rotor housing 26 and a rotor 28 arranged in the rotor housing 26. The harvested crop enters the rotor housing 26 through the intake transition region 22. The rotary threshing and separating assembly 24 threshes and separates the harvested crop. Grain and chaff fall through grates at the bottom of the rotor housing onto a cleaning assembly 34.

The cleaning assembly 34 removes the chaff and conducts the clean grain to a grain elevator 36 which conducts grain upwardly to a distributing screw conveyor 38. The distributing screw conveyor 38 deposits the clean grain in a grain tank 40. The clean grain in the grain tank 40 can be unloaded through an unloading auger 42 into a grain cart or auger wagon. Threshed straw separated from the grain is conducted out of the rotary threshing and separating assembly 24 through an outlet to a discharge beater 46. The discharge beater 46 ejects the straw from a rearward end of the combine 10.

The operation of the combine 10 is controlled from an operator's cab 48. A geographic position sensor in the form of a GPS receiver 50 for the reception of GPS (global positioning system) signals is attached above the operator's cab 48. Preferably mounted on one side of the clean grain elevator 36 is a capacitive moisture sensor 52 for measuring the moisture content of the clean grain. A yield sensor 54 is preferably located near the outlet of the clean grain elevator 36. In some embodiments, the yield sensor 54 comprises a sensor plate mounted for deflection; the deflection of the yield sensor is dependent upon the mass flow rate of the clean grain. The deflection of the impeller plate is measured and thus data on the mass flow rate of the harvested grain is provided.

A processor 56 located in the operator's cab 48 (or elsewhere on the combine 10) is preferably in electrical communication with the GPS receiver 50, the moisture sensor 52, and the yield sensor 54. The processor 56 is provided with an internal clock or receives external time signals, for example from the receiver 50. The processor 56 records the amount of harvested grain (measured by means of the yield sensor 54) and its moisture content (measured by means of the moisture sensor 52) dependent on the geographical position of the combine 10 (measured by means of the GPS receiver 50). The processor 56 logs the data and produces a field summary. Thus, it is possible to create a yield map with the logged data.

Figure 2:
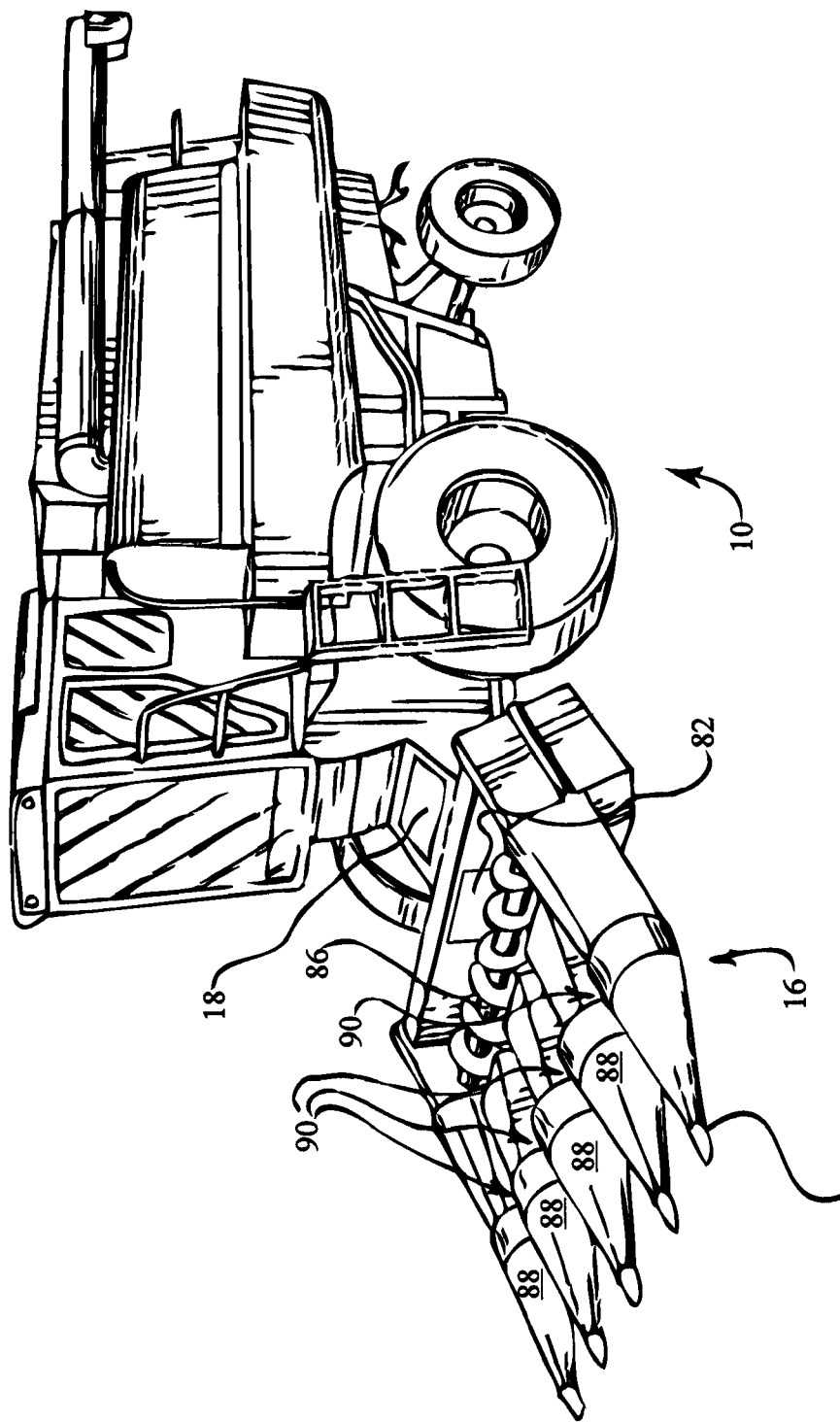
FIG. 2 is a front perspective view of a combine harvester.
Figure 3A:
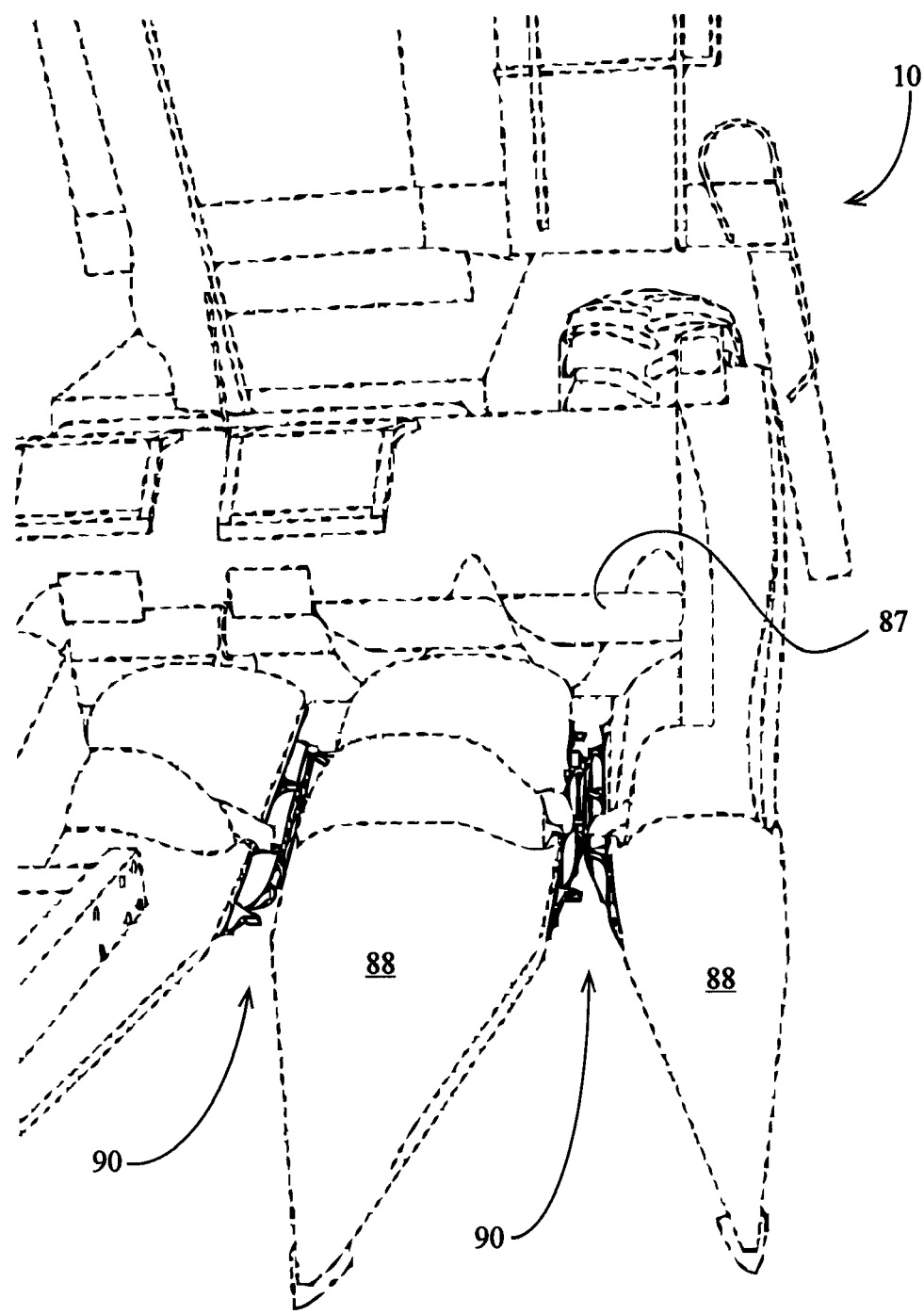
FIG. 3A is a front perspective view of a corn head.
Figure 3B:
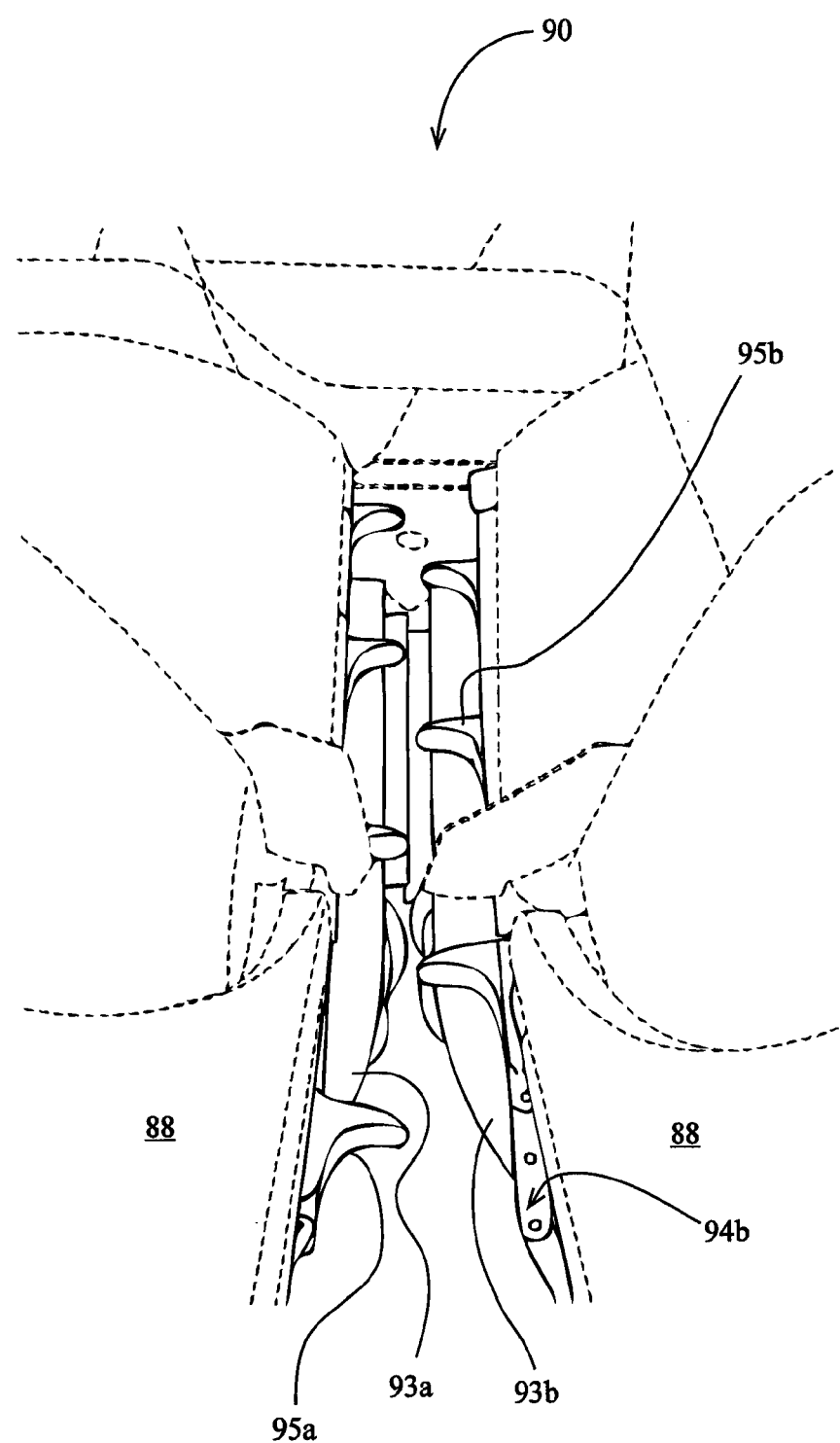
FIG. 3B is a front perspective view of a corn head row unit.

FIGS. 2, 3A and 3B illustrate a prior art combine 10 in which the harvesting assembly 16 comprises a corn head. The illustrated corn head includes four row units 90 disposed between five row dividers 88. Ears of corn are stripped from each of the four rows by a row unit 90 and then carried by an auger 87 to a trough 82 of the corn head 16 and to the feederhouse 18.

Figure 4:
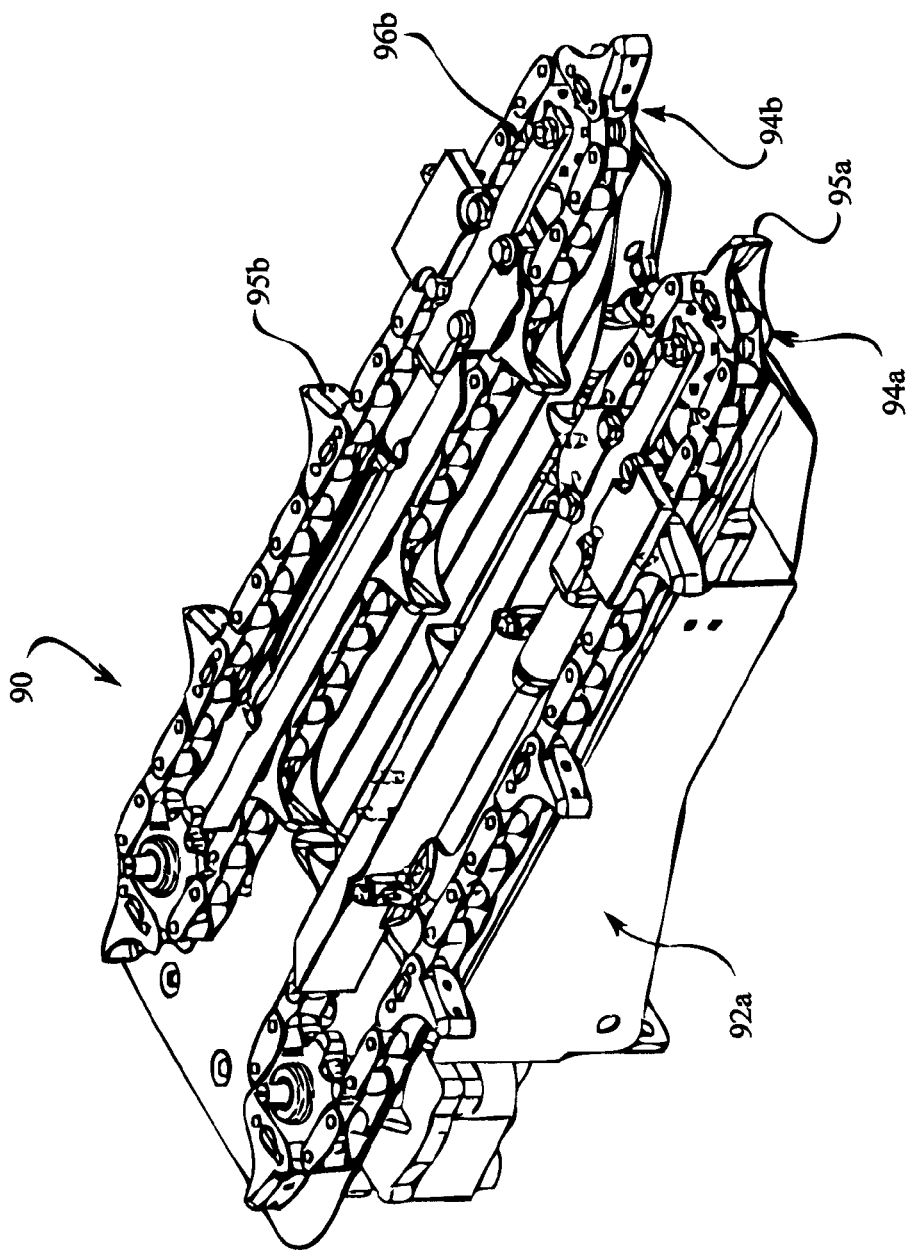
FIG. 4 is a front perspective view of a corn head row unit.
Figure 5:
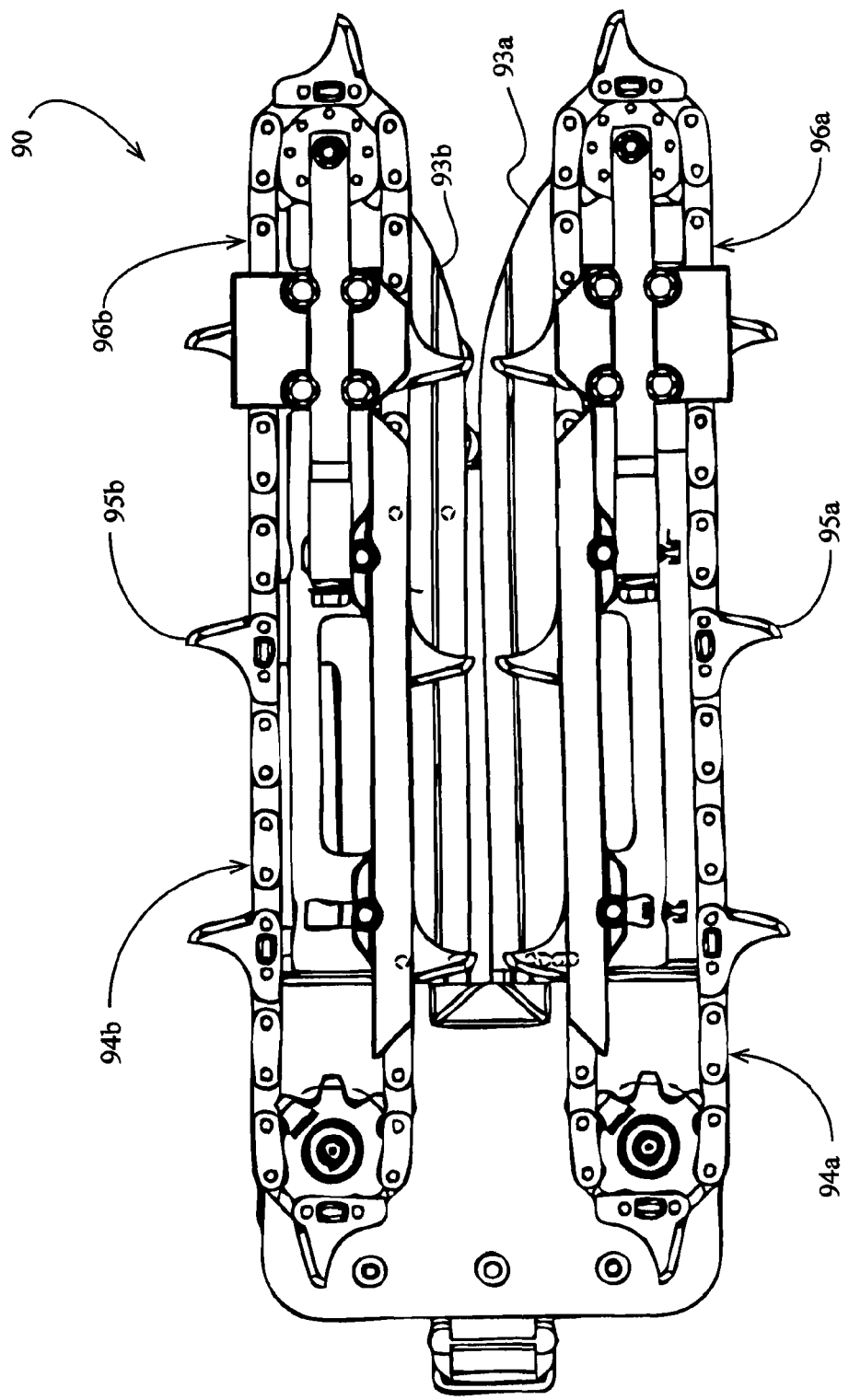
FIG. 5 is a top view of a corn head row unit.

FIGS. 4 and 5 are perspective and top views, respectively, of a corn head row unit 90. The row unit 90 is similar to that disclosed in U.S. Pat. No. 5,878,561, the disclosure of which is hereby incorporated herein in its entirety by reference. Each row unit 90 includes left and right frame portions 92 on which are supported left and right guide and idler assemblies 94a and 94b. The guide and idler assemblies 94 support left and right gathering chains 96a and 96b for driven rotation. The gathering chains 96 include a series of gathering fingers 95. Left and right stripper plates 93a and 93b are mounted to the left and right frame portions 92.

Figure 6:
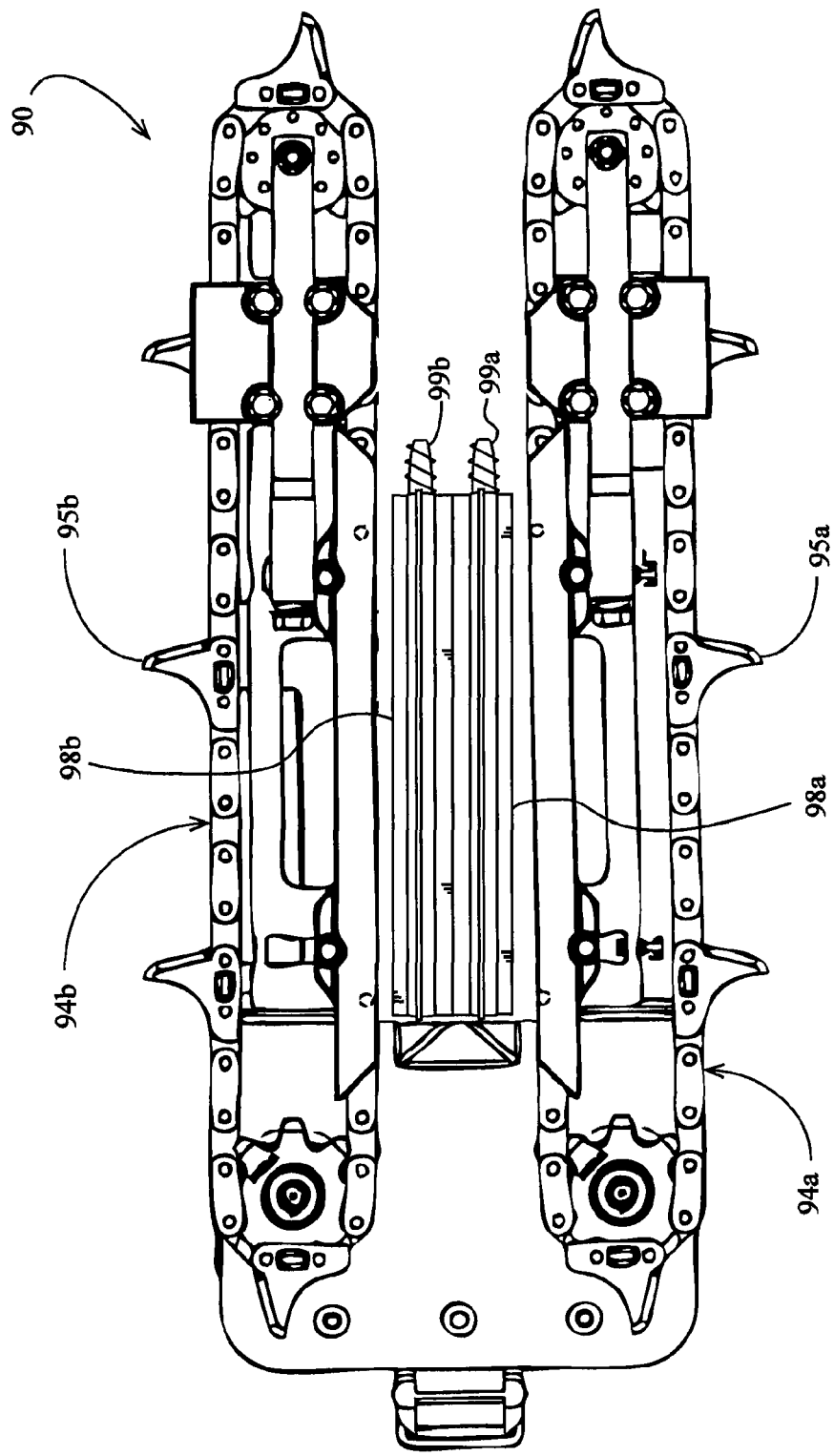
FIG. 6 is a top view of a corn head row unit.

FIG. 6 is a top view of the row unit 90 with the stripper plates 93a and 93b removed, revealing left and right stalk rollers 98a and 98b. Each stalk roller 98 preferably includes a threaded stalk gripper 99. The stalk rollers 98 are mounted to the row unit 90 for driven rotation by a prime mover (not shown). In operation, after stalks are gathered in between the stripper plates 93, the stalks are gripped by the stalk grippers 99. The stalks are then drawn downward by the stalk rollers 98; corn ears attached to the stalks are detached from the stalks and retained above the stripper plates 93 while the stalks are drawn below the stripper plates and discarded. Gathering fingers 95 draw the ears rearward toward the auger 87.

Figure 7A:
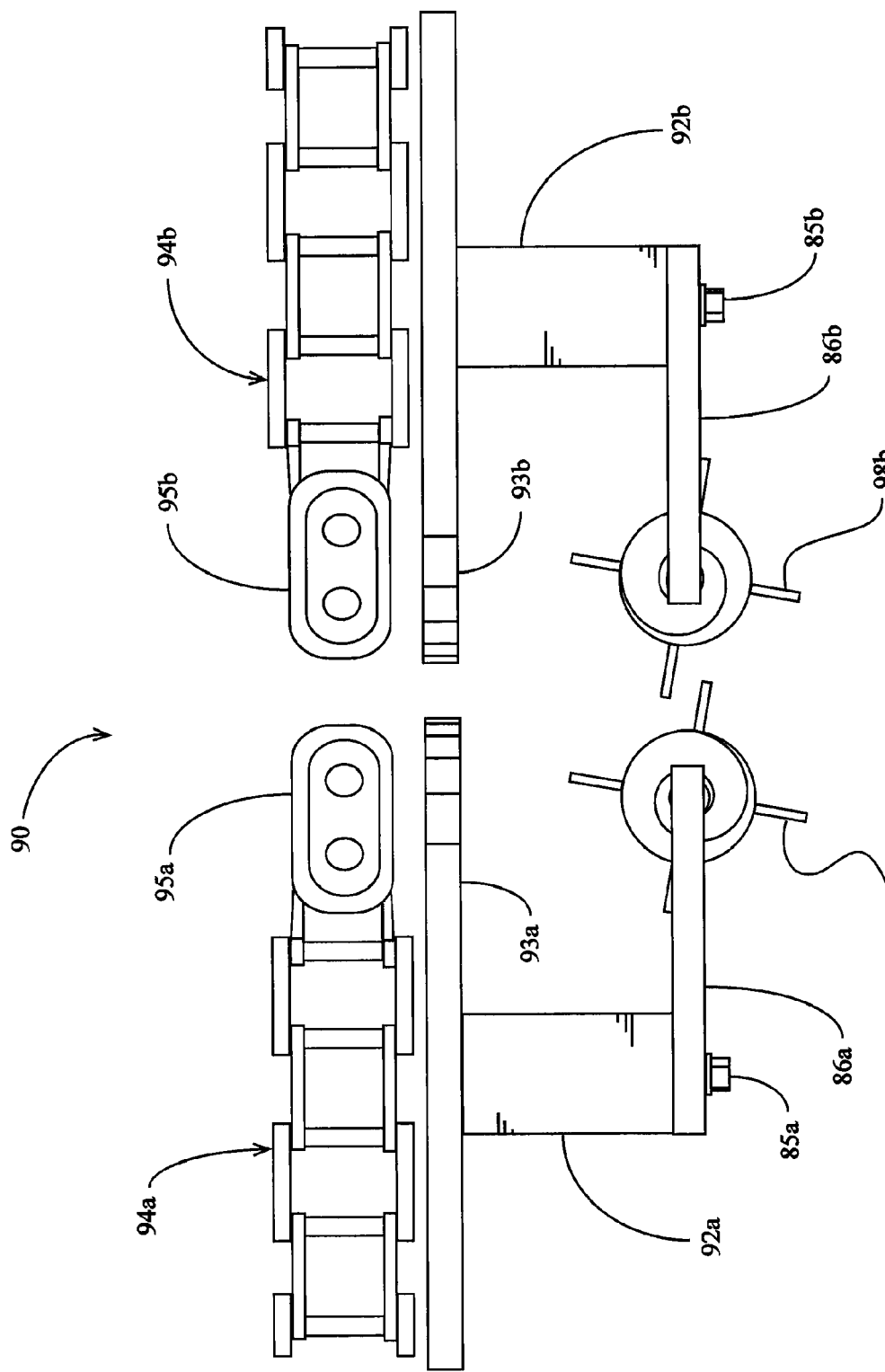
FIG. 7A is front elevation view of a corn head row unit.
Figure 7B:
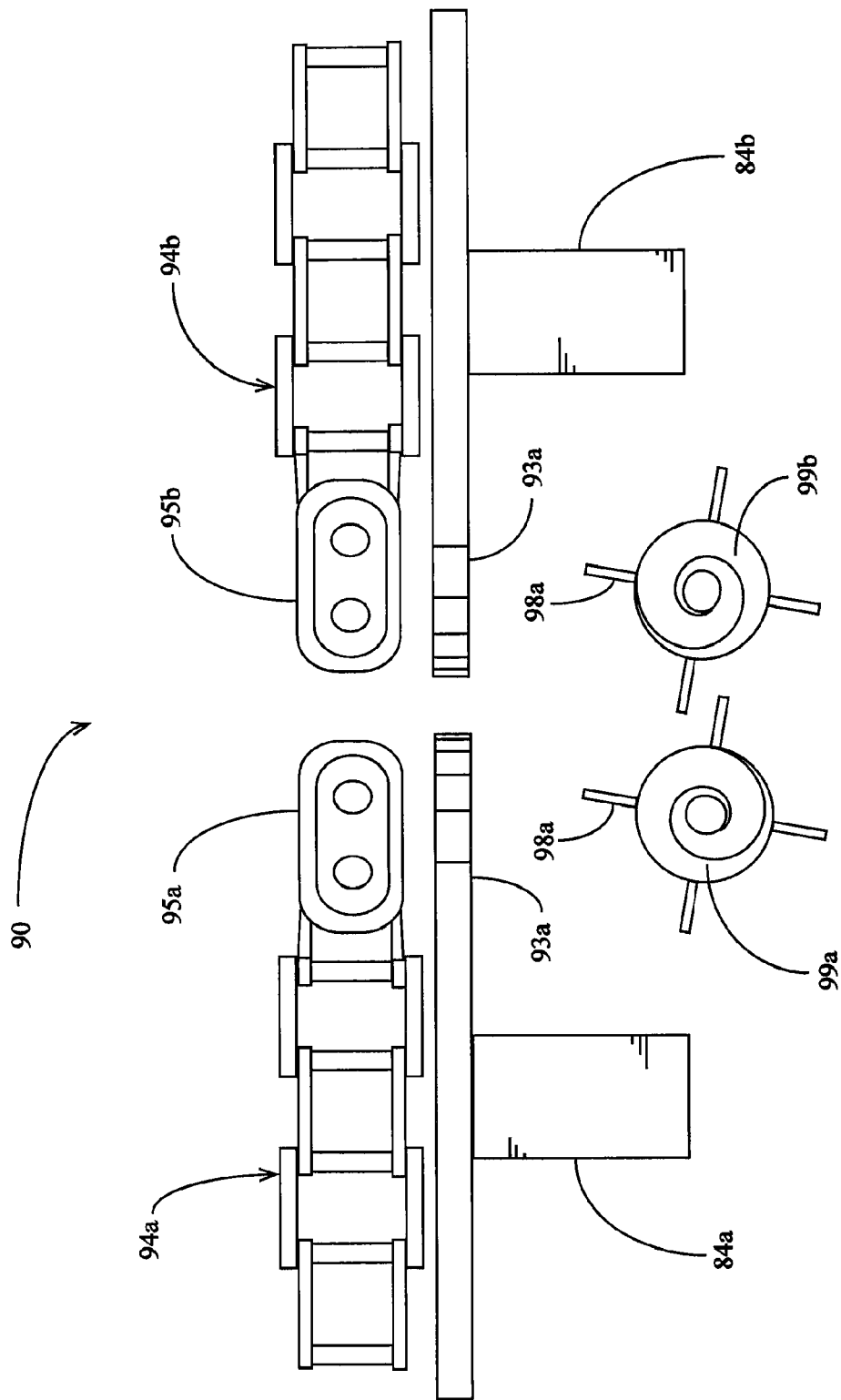
FIG. 7B is a front elevation view of a corn head row unit.
Figure 8:
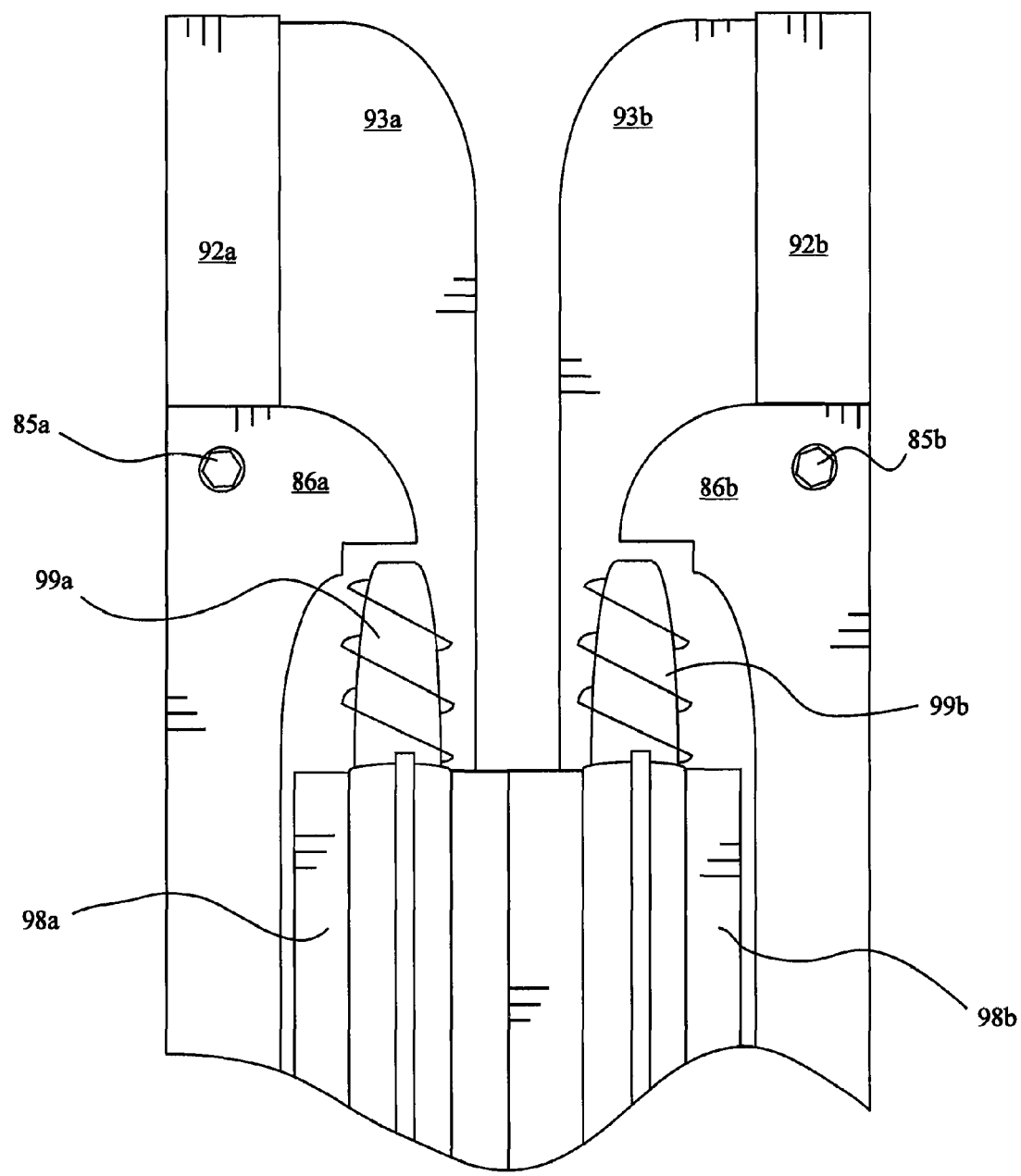
FIG. 8 is a partial bottom view of a corn head row unit.

FIGS. 7A and 8 are front and bottom views, respectively, of the row unit 90. The row unit 90 includes left and right floor portions 86a and 86b. Floor portions 86 are attached to the frame portions 92 by bolts 85. The floor portions 86 are not shown in FIG. 7B in order to provide an unobstructed view of the stalk rollers 98 and stalk grippers 99.

Mechanical Sensor Apparatus

Figure 9:
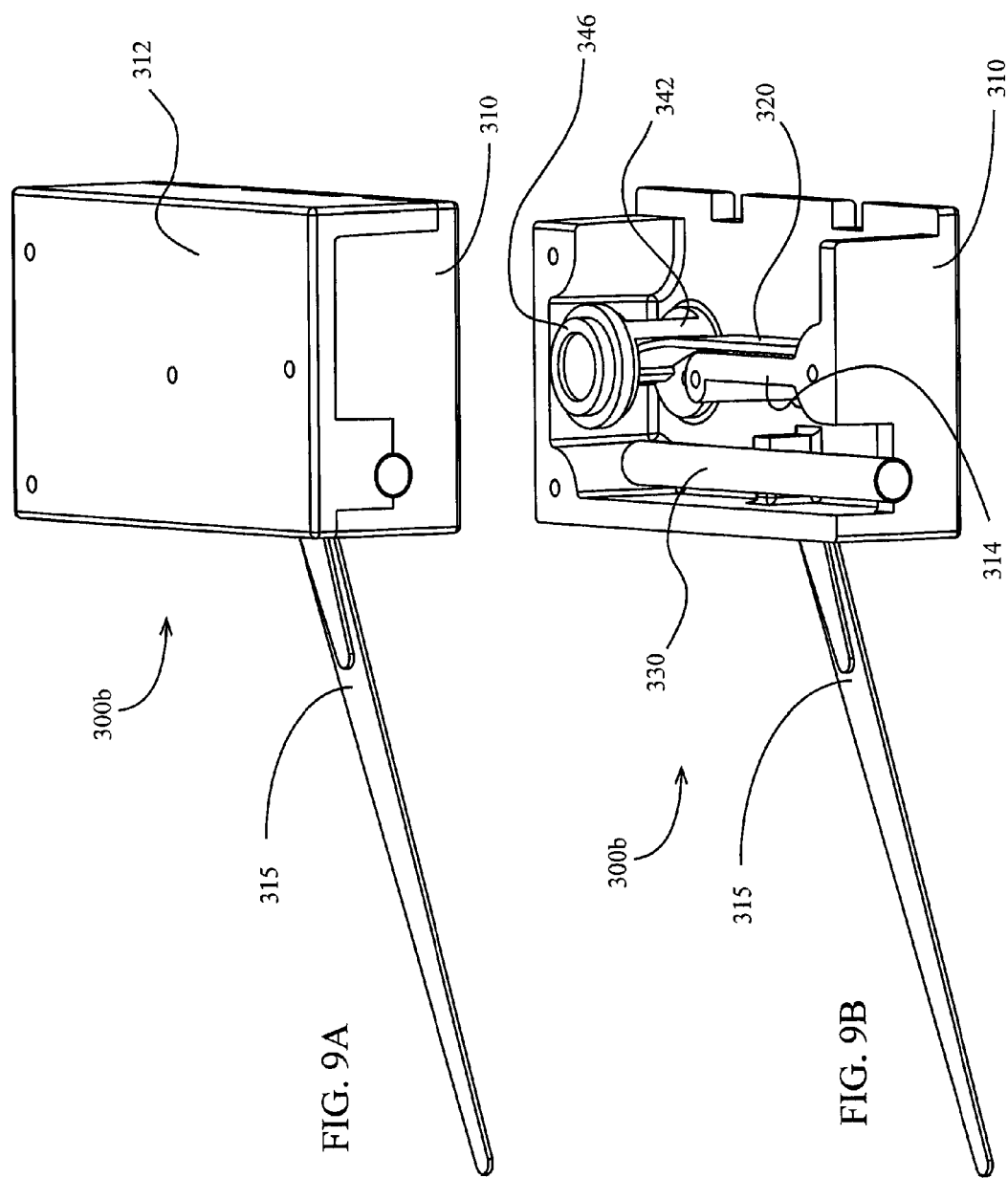
FIG. 9A is a bottom perspective view of an embodiment of a stalk sensor.
FIG. 9B is a bottom perspective view of the stalk sensor of FIG. 9A.
Figure 10:
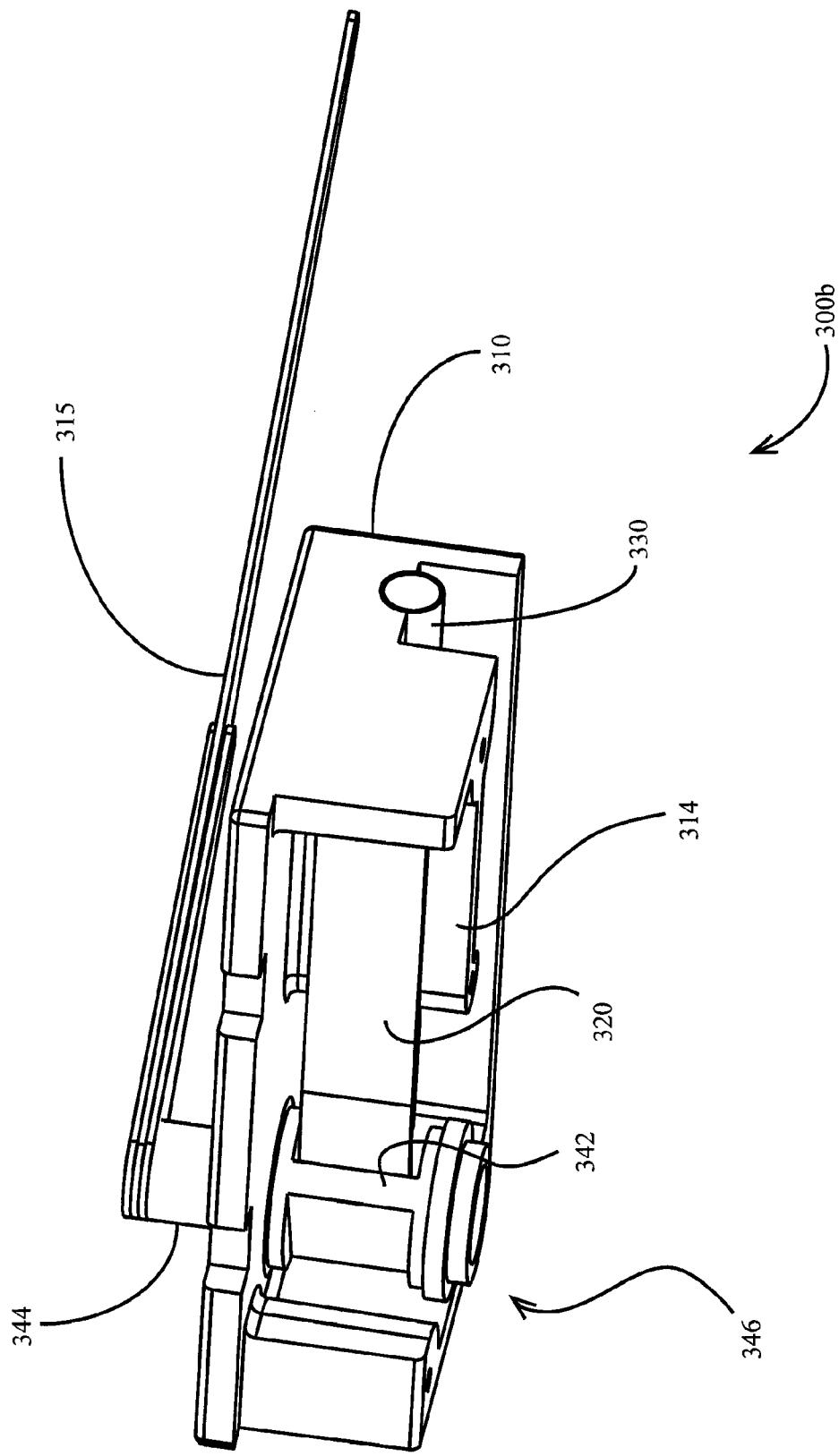
FIG. 10 is a rear perspective view of the stalk sensor of FIG. 9A.

A stalk sensor 300b is illustrated in FIG. 9A. The stalk sensor 300b includes a housing 310 and a cover 312. Turning to FIGS. 9B and 10, in which the cover 312 is removed, a pin 346 is rotatably mounted to the housing 310. A spring 320 is mounted to a platform 314, which platform is preferably formed as a part of housing 310. The spring 320 preferably contacts a flat portion 342 of the pin 346. A sensor tube 330 is preferably housed within the housing 315. A feeler 315 is preferably mounted to the pin 346 by a stem 344.

Figure 11:
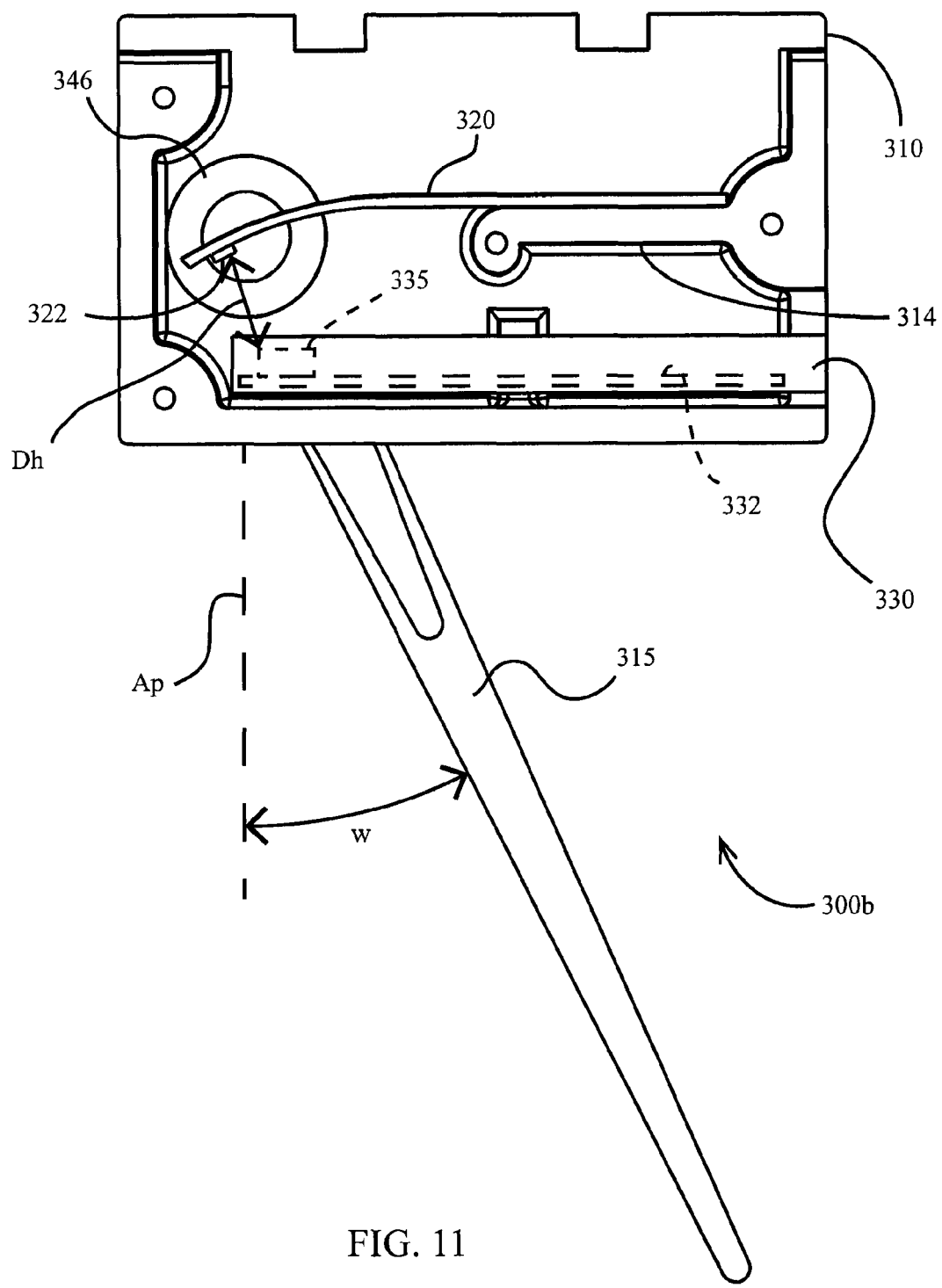
FIG. 11 is a bottom view of the stalk sensor of FIG. 9A.

FIG. 11 illustrates a bottom view of the stalk sensor 300b with the cover 312 removed. A circuit board 332 is preferably mounted within sensor tube 330. A sensor 335 is mounted to the circuit board 332. The sensor 335 is in electrical communication with the circuit board. The sensor 335 is preferably a sensor adapted to generate a signal proportional to the strength of a magnetic field proximate to the sensor, such as a Hall-effect sensor. A magnet 322 is mounted to the spring 320. As the feeler 315 rotates with the pin 346, the flat portion 342 (not shown in FIG. 10) of pin 346 deflects the spring 320. An axis Ap preferably defines the position of feeler 315 for which the spring 320 is at its least deflected (i.e., most relaxed) state. As the feeler 315 rotates through an increasing angle w from the axis Ap, the spring 320 deflects such that a distance Dh between the magnet 322 and the sensor 335 decreases. Thus, the distance Dh is inversely related to the angle w.

Figure 12:
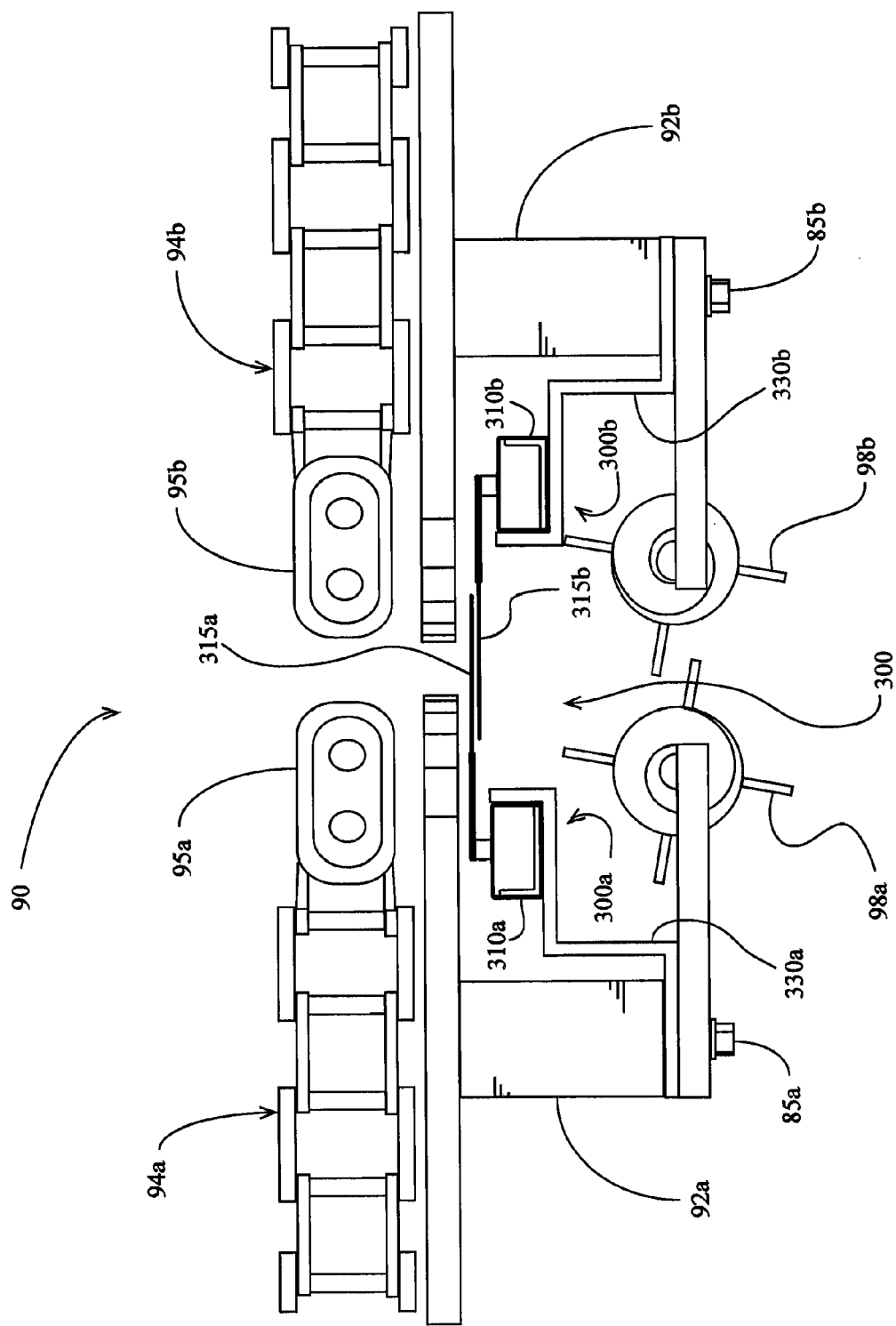
FIG. 12 is a front elevation view of an embodiment of a corn head row unit with the stalk sensor of FIG. 9A mounted thereto.

Comparing FIG. 7A with FIG. 12, two stalk sensors 300a and 300b (together referred to herein as a single stalk sensor 300) are preferably installed in the combine row unit 90. The sensors 300a and 300b are mounted to brackets 330a and 330b, respectively. Brackets 330a and 330b are mounted to the row unit frame portions 92a and 92b, respectively. Mounting of each bracket 330 is preferably accomplished by removing the bolt 85 and the floor portion 86, placing the bracket against the frame portion 92, and bolting the floor portion 86 to the frame portion through a hole (not shown) in the bracket.

Figure 13:
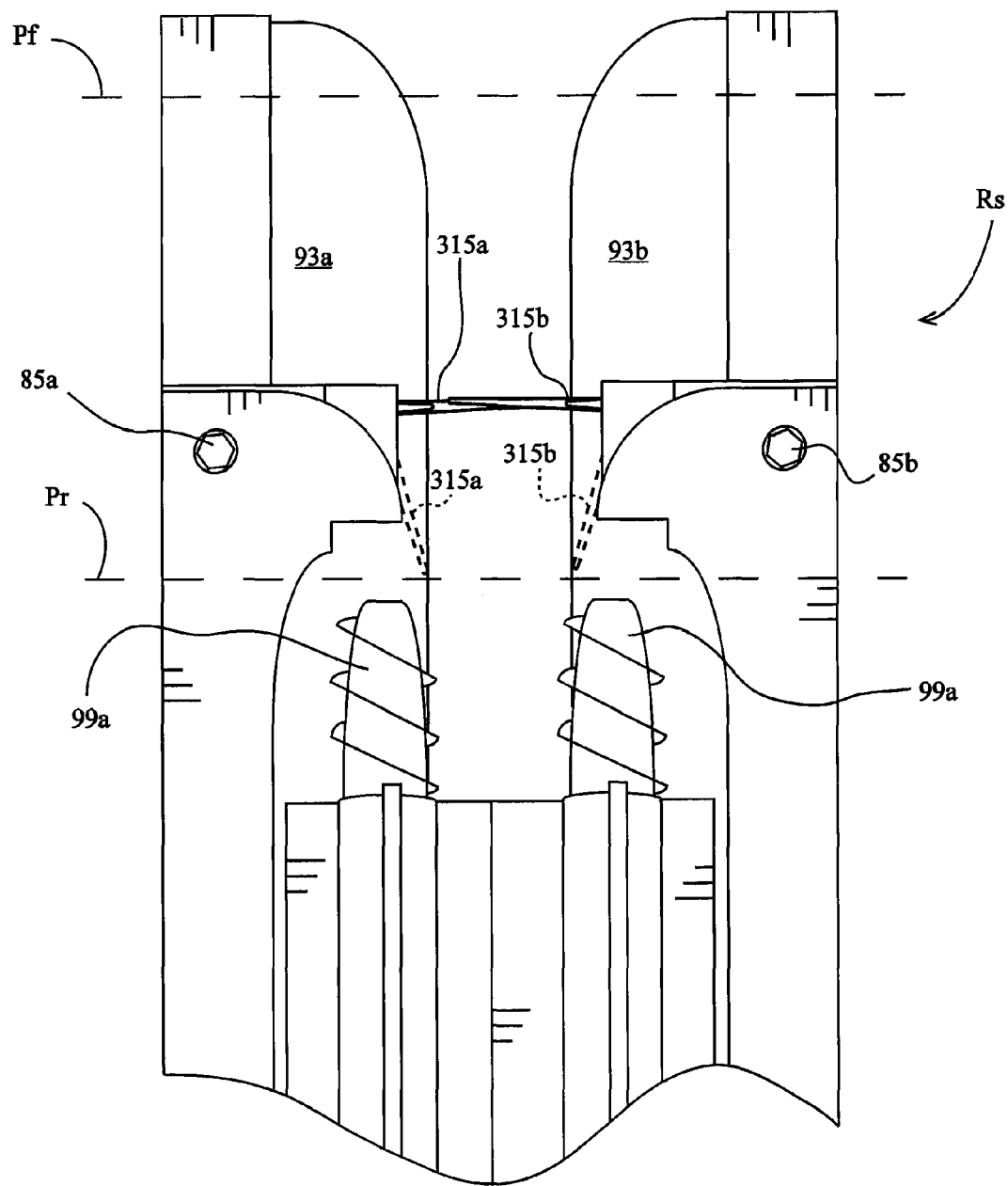
FIG. 13 is a bottom view of the corn head row unit and stalk sensor of FIG. 12.

As illustrated in FIG. 12, the brackets 330 are configured such that the sensors 300a and 300b are disposed with their respective feelers 315 overlapping in the transverse direction. Turning to FIG. 13, the sensors 300a, 300b are mounted to the brackets 330 such that the feelers 315a and 315b also overlap in the travel direction in their undisturbed state. Continuing to refer to FIG. 13, the feelers 315 are indicated in their displaced state in dashed lines. The illustrated displacement would correspond to the maximum displacement imposed by a stalk having a diameter equal to the transverse distance between the stripper plates 93a and 93b.

Continuing to refer to FIG. 13, a plane Pf corresponds to a position along the path of stalk travel at which the stalk is at least partially transversely constrained by the stripper plates 93. A plane Pr corresponds to a position along the path of stalk travel prior to the stalk grippers 99a, 99b. As illustrated, the sensors 300a, 300b are preferably disposed such that the range of motion (e.g., between the solid-line and dashed-line positions in FIG. 13) of feelers 315 lies in a sensing region Rs between planes Pf and Pr.

Figures 16A, 16B:
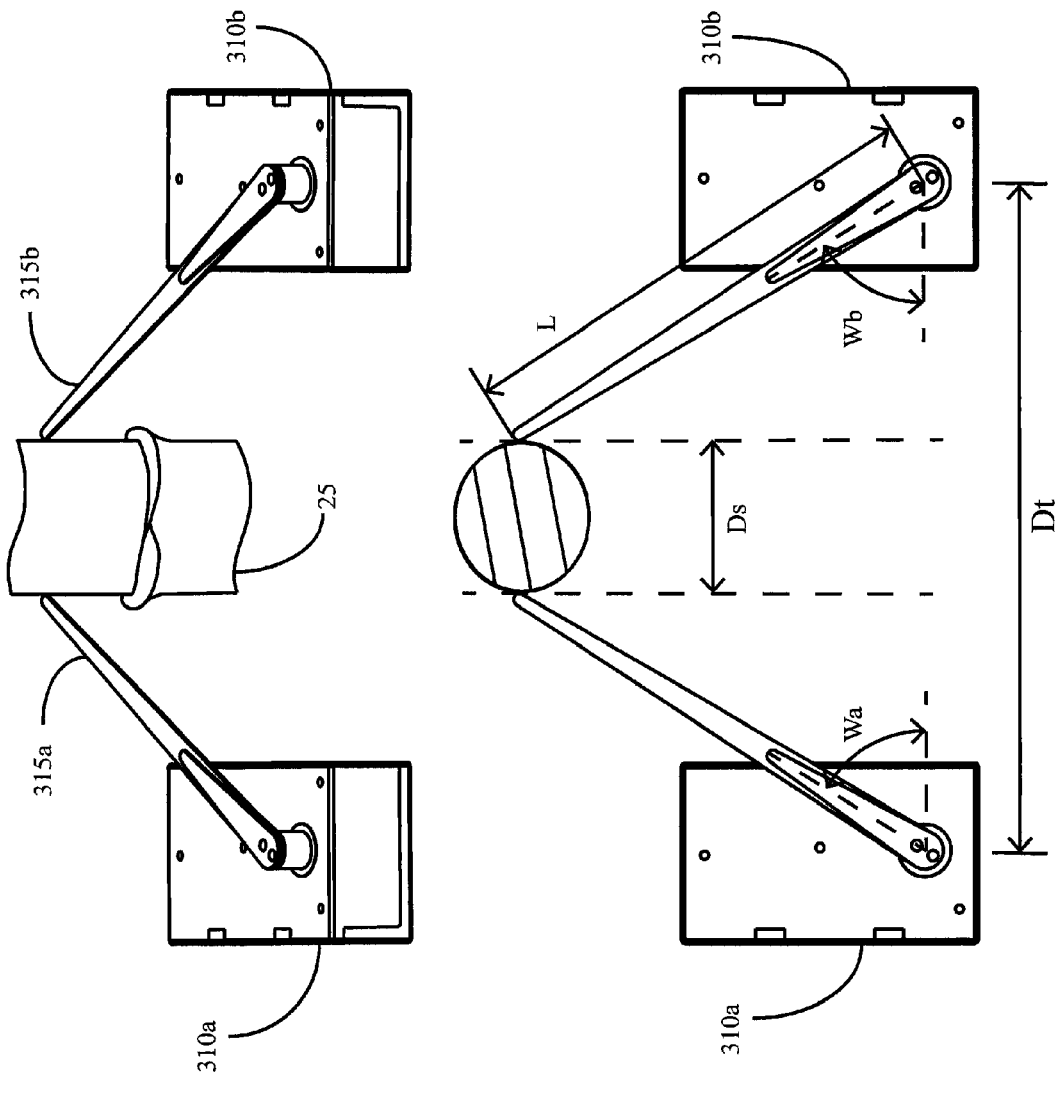
FIG. 16A is a front perspective view of the stalk sensor of FIG. 12 interacting with a stalk.
FIG. 16B is a top view of the stalk sensor of FIG. 12 interacting with a stalk.

Turning to FIGS. 14A through 16B, the action by which the feelers 315 are displaced is illustrated. FIGS. 14A, 15A, and 16A illustrate front perspective views of a stalk sensor 300 comprising left and right sensors 300a and 300b as a stalk 25 moves through the row unit 90. FIGS. 14B, 15B, and 16B illustrate top views of a stalk sensor 300 comprising left and right sensors 300a and 300b as a stalk 25 moves through the row unit 90. In FIGS. 14A and 14B, a stalk 25 is about to contact the feelers 315a and 315b. In FIGS. 15A and 15B, the stalk 25 has moved farther through the row unit 90 and thereby deflected the feelers 315. In FIGS. 16A and 16B, the stalk 25 has deflected both feelers 315 to the maximum extent before allowing the feelers to be returned to their undisturbed state by the springs 320 (FIG. 11). The maximum deflection of the feeler arms 315a, 315b by the stalk 25 is represented by the angles Wa, Wb, respectively.

Stalk Measurement Systems

Figure 17:
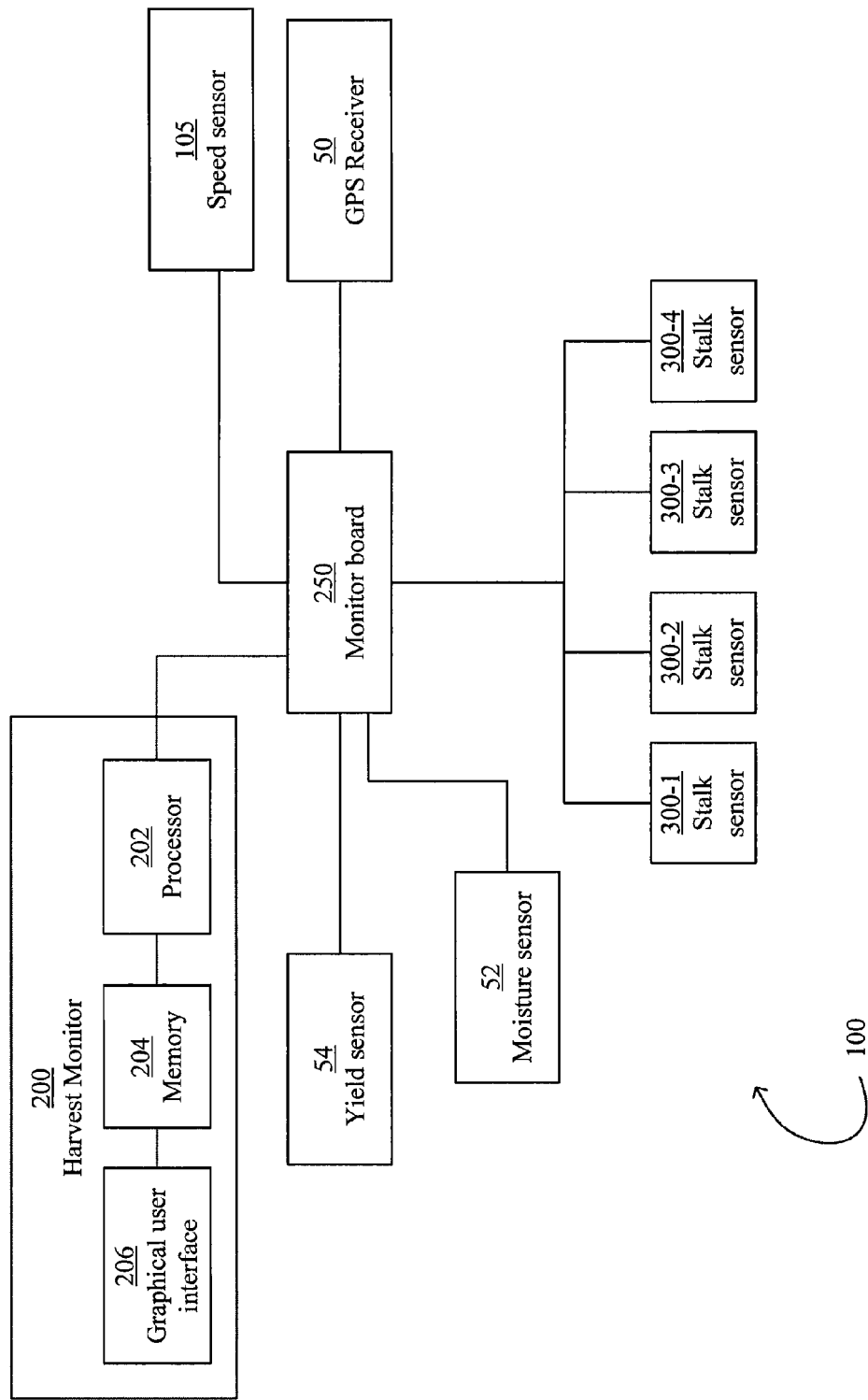
FIG. 17 is a schematic illustration of an embodiment of a stalk sensor system.

A stalk measurement system 100 incorporating a series of stalk sensors 300 is illustrated in FIG. 17. The stalk sensors 300 are preferably in electrical communication with a monitor board 250. As discussed elsewhere herein, each stalk sensor 300 preferably comprises a pair of stalk sensors 300a, 300b. The monitor board 250 preferably includes a CPU and a memory. The monitor board 250 is preferably in electrical communication with a harvest monitor 200. The harvest monitor 200 preferably includes a processor 202, a memory 204, and a graphical user interface (GUI) 206. The harvest monitor 200 also preferably includes a wireless communication device, removable memory port (e.g., USB port), or other device for transmitting data to and from the harvest monitor 200. It should be appreciated in light of the instant disclosure that the monitor board 250 and harvest monitor 200 may be combined in a single piece of hardware in some embodiments. The monitor board 250 is preferably in electrical communication with the yield sensor 54 and the moisture sensor 52. The yield sensor 54 may be an impact-type yield sensor configured to generate a signal proportional to the mass flow rate of grain through the clean grain elevator as is known in the art (such as that disclosed in U.S. Pat. No. 5,561,250), or may comprise another sensor configured to measure the rate at which grain is harvested. The monitor board 250 is preferably in electrical communication with a speed sensor 105, which may comprise a radar speed sensor as is known in the art. The monitor board 250 is preferably in electrical communication with the receiver 50, which may comprise a device configured to receive and interpret signals from GPS or other satellite-based positioning systems (e.g., GLONASS or Galileo).

Figure 18:
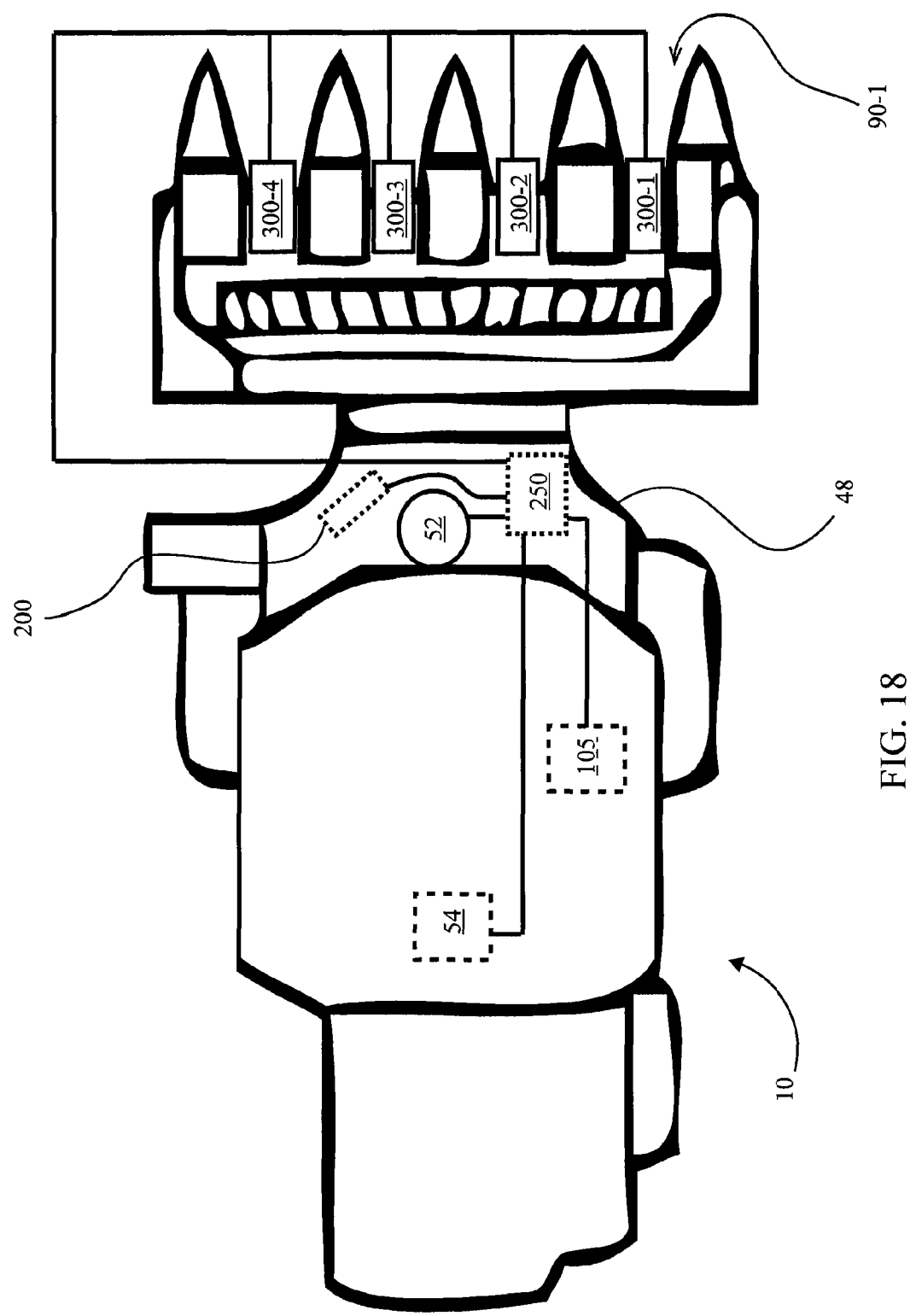
FIG. 18 is a schematic illustration of the stalk sensor system of FIG. 17 on a combine.

The stalk measurement system 100 is shown installed on a combine 10 having four row units 90 in FIG. 18. Each stalk sensor 300 is preferably mounted to a row unit 90. Although a four-row combine is illustrated herein, embodiments with greater numbers of row units and corresponding stalk sensors is possible using the same principles described herein. The monitor board 250 is preferably mounted inside the cab 48 of the combine. The harvest monitor 200 is preferably mounted inside the cab 48 within the view of the operator. The positioning system is preferably mounted to the roof of the combine cab 48. The speed sensor 105 is preferably mounted to the underside of the combine 10. The yield sensor 54 is mounted within the combine, preferably intercepting or interacting with the flow of grain as illustrated in FIG. 1.

Stalk Measurement Methods

Figure 19:
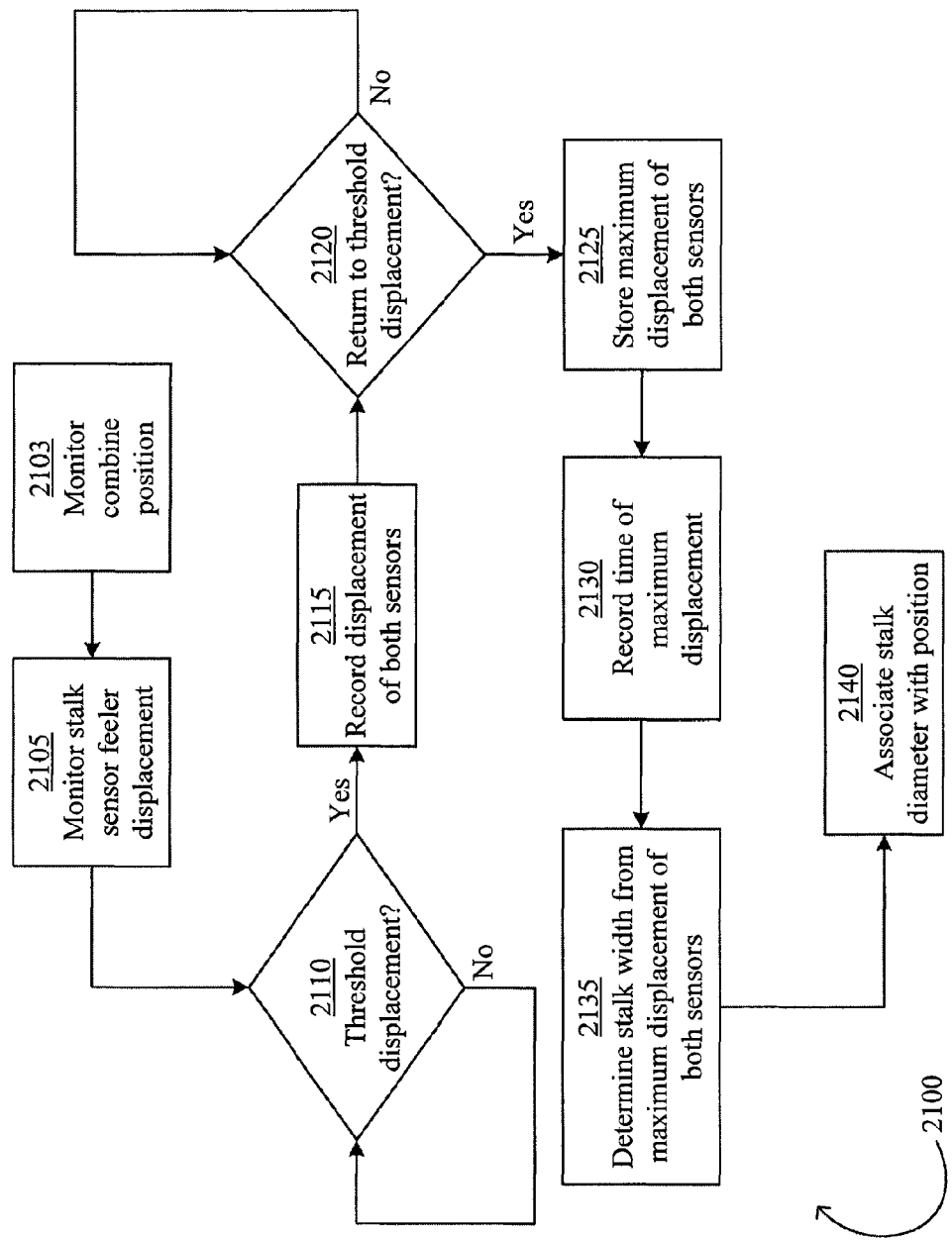
FIG. 19 is a process flow diagram illustrating an embodiment of a process for measuring stalk diameter.

Turning to FIG. 19, a process 2100 is illustrated for measuring stalk width using a system such as the stalk measurement system 100. At step 2103, the monitor board records the position of the combine 10 at discrete times using the signal from the GPS receiver 50. At step 2105, the monitor board 250 monitors the positions of each feeler 315 of the stalk sensors 300a,b from each row unit 90, preferably by monitoring the signals generated by each sensor 335. As described elsewhere herein, the signal generated by each sensor 335 is proportional to the angle of displacement w (FIG. 11) of the associated feeler 315. At step 2110, the monitor board preferably determines whether each feeler 315 has passed a threshold displacement, e.g., 2 degrees from the undisturbed position (along axis Ap, FIG. 11) by comparing the signal from each sensor 335 to a baseline. Once the threshold for either feeler 315a, 315b of any stalk sensor 300 has exceeded the threshold, at step 2115 the monitor board 250 preferably records the displacement of both feelers 315a, 315b of the stalk sensor 300. At step 2120, the monitor board 250 preferably determines whether both feelers 315a, 315b have returned within a threshold angle w (e.g., 2 degrees) of the undisturbed position. Once the feelers 315 are both below the threshold displacement, at step 2125 the monitor board 250 stores the maximum displacement Wa, Wb (FIG. 16B) of each feeler 315a, 315b and at step 2130 stores the time of the maximum displacement of the feelers 315. At step 2135, the monitor board 250 preferably calculates the diameter of the stalk 25.

In accomplishing step 2135, the diameter Ds of the stalk 25 may be measured using the maximum deflection angles Wa, Wb (FIG. 16B) of feeler arms 315a, 315b caused by the stalk as it moves through the row unit 90 using the relationship:

$$Ds = Dt - L(\sin(Wa) + \sin(Wb))$$

Where (as illustrated in FIG. 16B):
  L represents the length of the feelers 315;
  Dt represents the total distance between the feeler rotation axes (i.e., between the axes of rotation of the pins 346).
  The values of Dt and L are preferably pre-loaded in the memory 204.

At step 2140, the monitor board preferably associates the measured stalk diameter with a position in the field by matching the time of maximum displacement of one of the feelers 315 to a position recorded by position sensor 105.

System Setup and Configuration

Figure 20A:
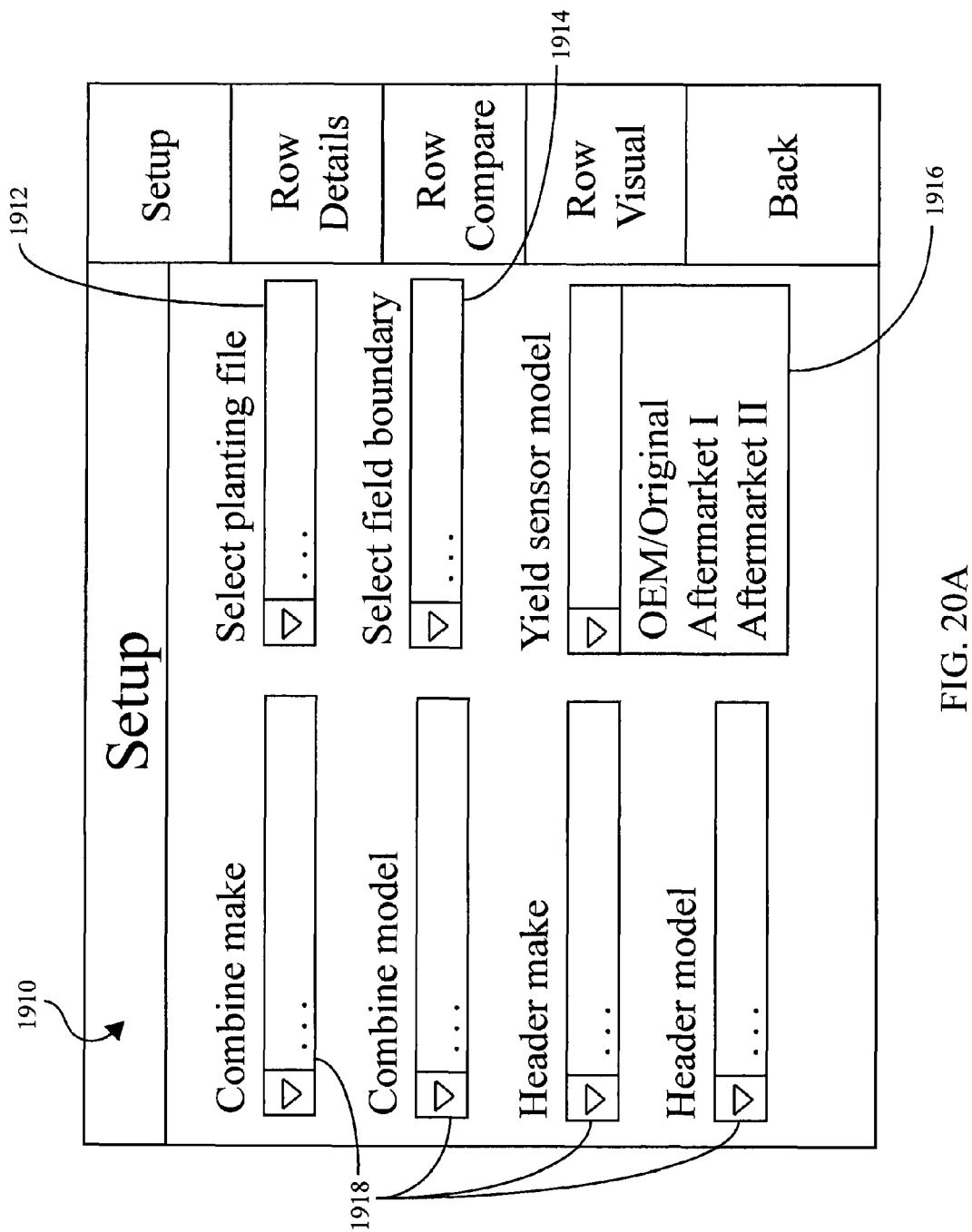
FIG. 20A is an embodiment of a monitor screen display for entering harvest monitor setup parameters.
Figure 20B:
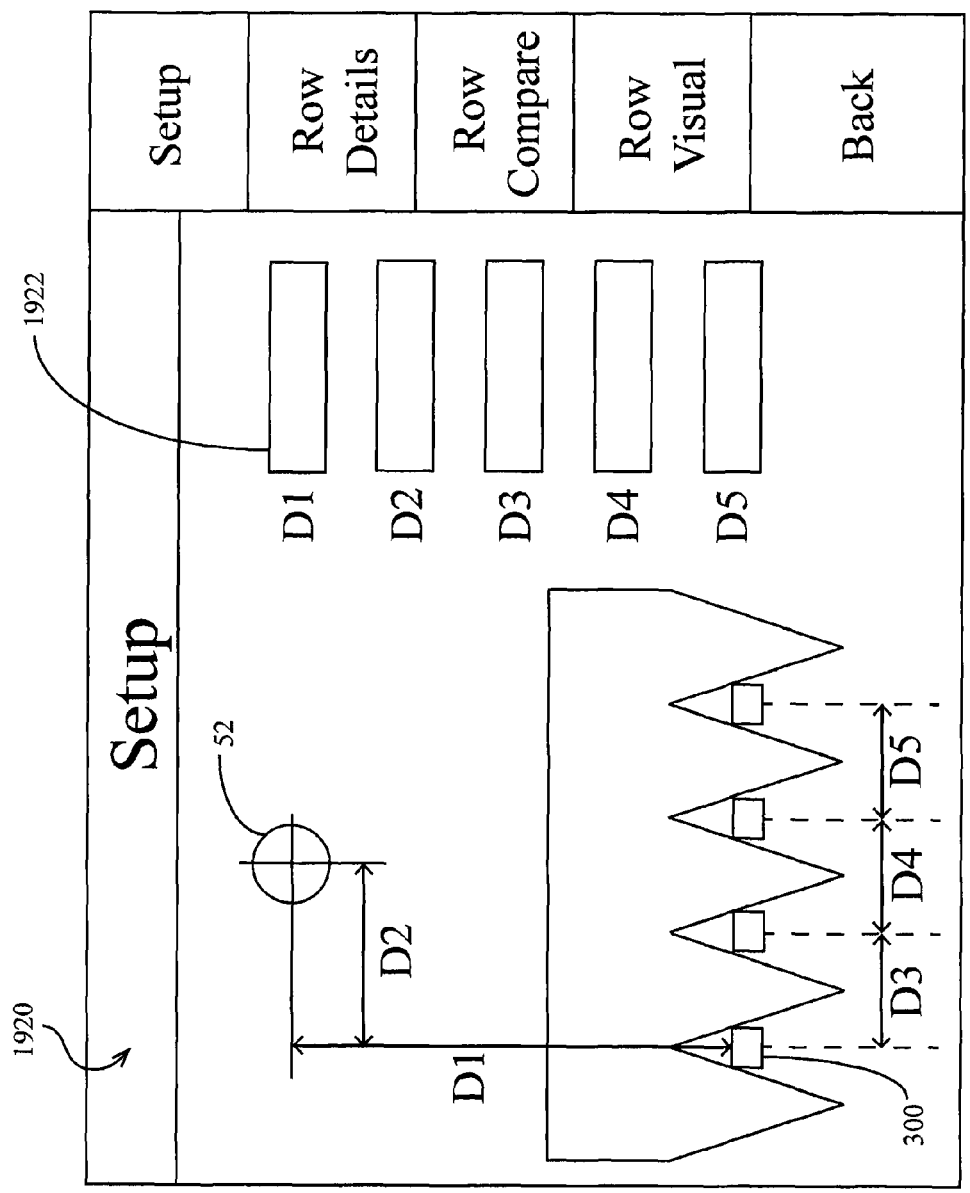
FIG. 20B is an embodiment of a monitor screen display for entering stalk measurement system GPS offsets.

As illustrated in FIGS. 20A and 20B, the harvest monitor 200 preferably displays a series of setup screens allowing the user to provide setup and configuration inputs to the harvest monitor. As illustrated in FIG. 20A, a setup screen 1910 allows the user to select the applicable combine make, combine model, header make, header model and yield sensor model using drop down menu bars 1918. When the operator presses or otherwise selects one of the menu bars 1918, a drop down menu 1916 is preferably displayed such that the operator may select from a set of relevant choices. Once the combine header configuration is entered by the user, the system 100 preferably identifies a system variable (e.g., the distance Dt) based on the user input. The planting file selection bar 1912 preferably allows the user to enter a file name of a planting file containing planting-related data such as seed placement, location of metering errors, population, seed type, and the location of planter tire tracks. The field boundary selection bar 1914 enables the user to select a field boundary file corresponding to a field to be harvested. It should be appreciated that the planting file may be provided using the removable memory port or other device provided in the harvest monitor 200. Turning to FIG. 20B, a setup screen 1920 allows the user to enter GPS offsets for use by the harvest monitor 200 in determining the location of each stalk sensor 300. For example, using entry fields 1922, the operator may enter the forward distance D1 between the GPS receiver 50 and the stalk sensors 300, the transverse distance D2 between the GPS receiver and the left-most stalk sensor 300, and the transverse distances D3,D4,D5 between the stalk sensors 300.

Stalk Yield Estimation Methods

Figure 21:
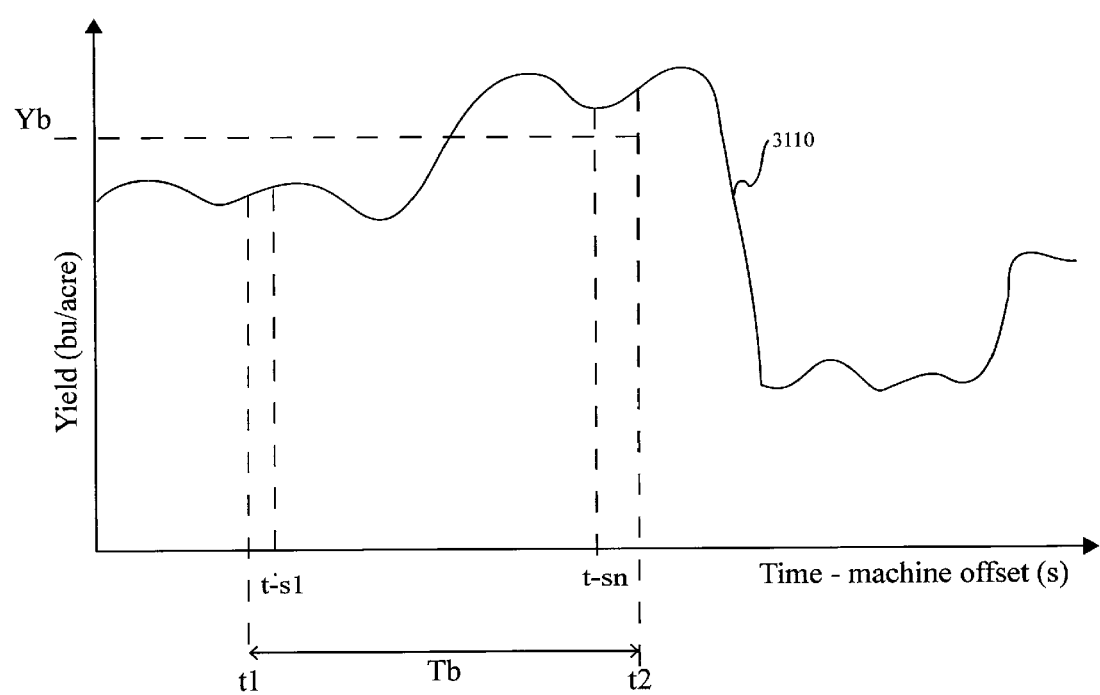
FIG. 21 is a plot of measured yield over time.

As the combine 10 traverses the field, the harvest monitor 200 preferably records the yield over time using the signal from the yield sensor 54 as is known in the art. Turning to FIG. 21, the recorded yield data corresponds to a yield curve 3110. As indicated on the x-axis of the plot, the yield curve 3110 is preferably shifted by a machine offset (e.g., 7 seconds) corresponding to a grain processing delay between the time at which stalks 25 enter the row units 90 and the time at which grain from the stalks reaches the yield sensor 54. Over each recording period Tb (e.g., 1 second) the harvest monitor preferably records an average yield (block yield Yb) corresponding to the average value of yield curve 110 during the recording period (in FIG. 21, between times t1 and t2 marking the beginning and end of the recording period Tb).

Figure 22:
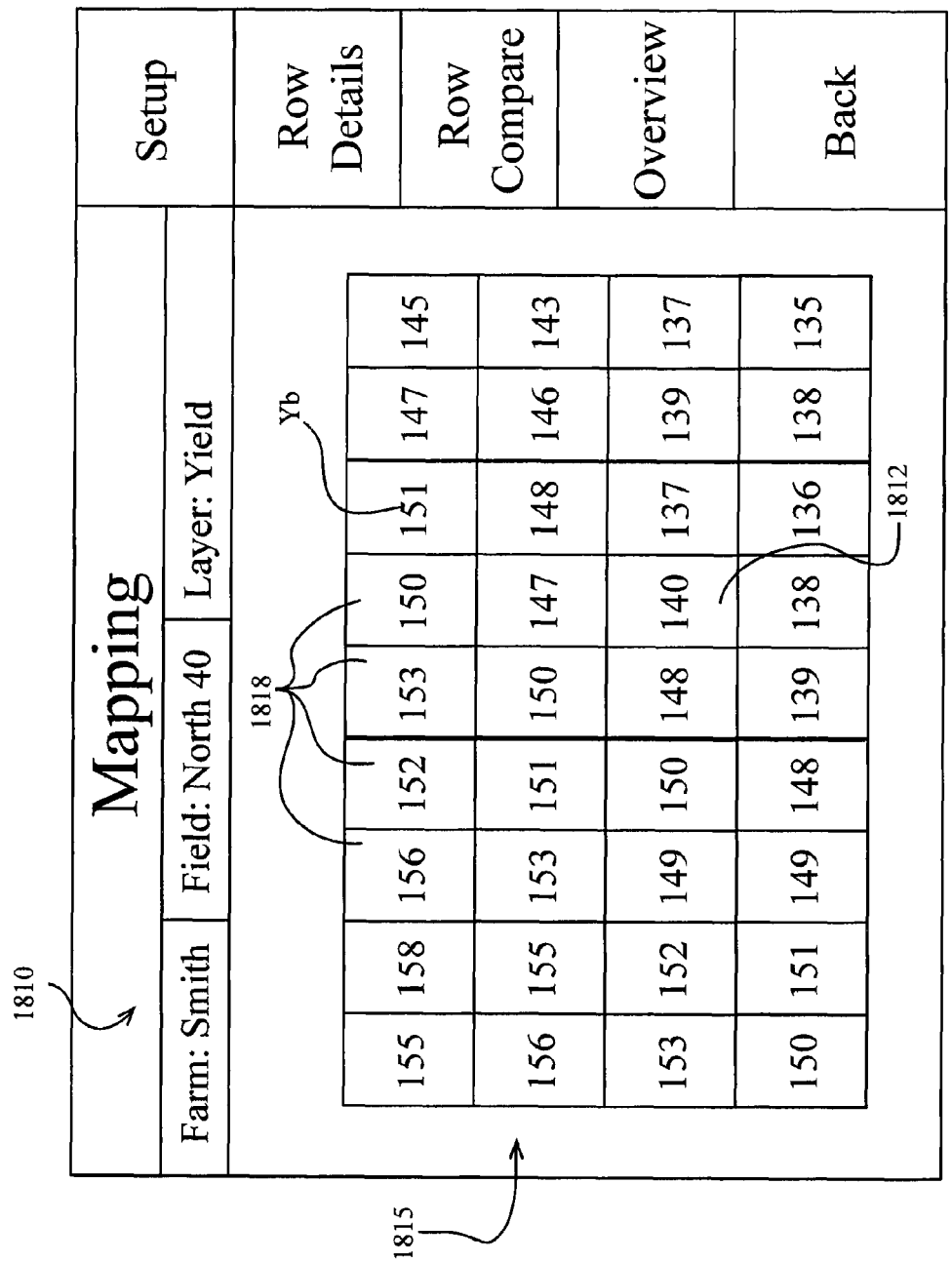
FIG. 22 illustrates another embodiment of a monitor screen displaying a yield map.

Turning to FIG. 22, the harvest monitor 200 preferably displays a yield map screen 1810 including a yield map 1815. The yield map 1815 corresponds to a harvested area of a field and includes yield blocks 1818. The mapped spatial area of yield blocks 1818 preferably) corresponds to the area harvested by the combine 10 during discrete recording periods Tb (FIG. 21). The block yield Yb associated with each yield block 1818 corresponds to the average yield during the associated recording period Tb; e.g., the average yield recorded in the yield block indicated by the reference numeral 1812 was 140 bushels per acre. It should be appreciated that in preferred mapping techniques, each yield block is colored according to a color-yield legend in order to more clearly indicate spatial variation in yield.

Figure 23:
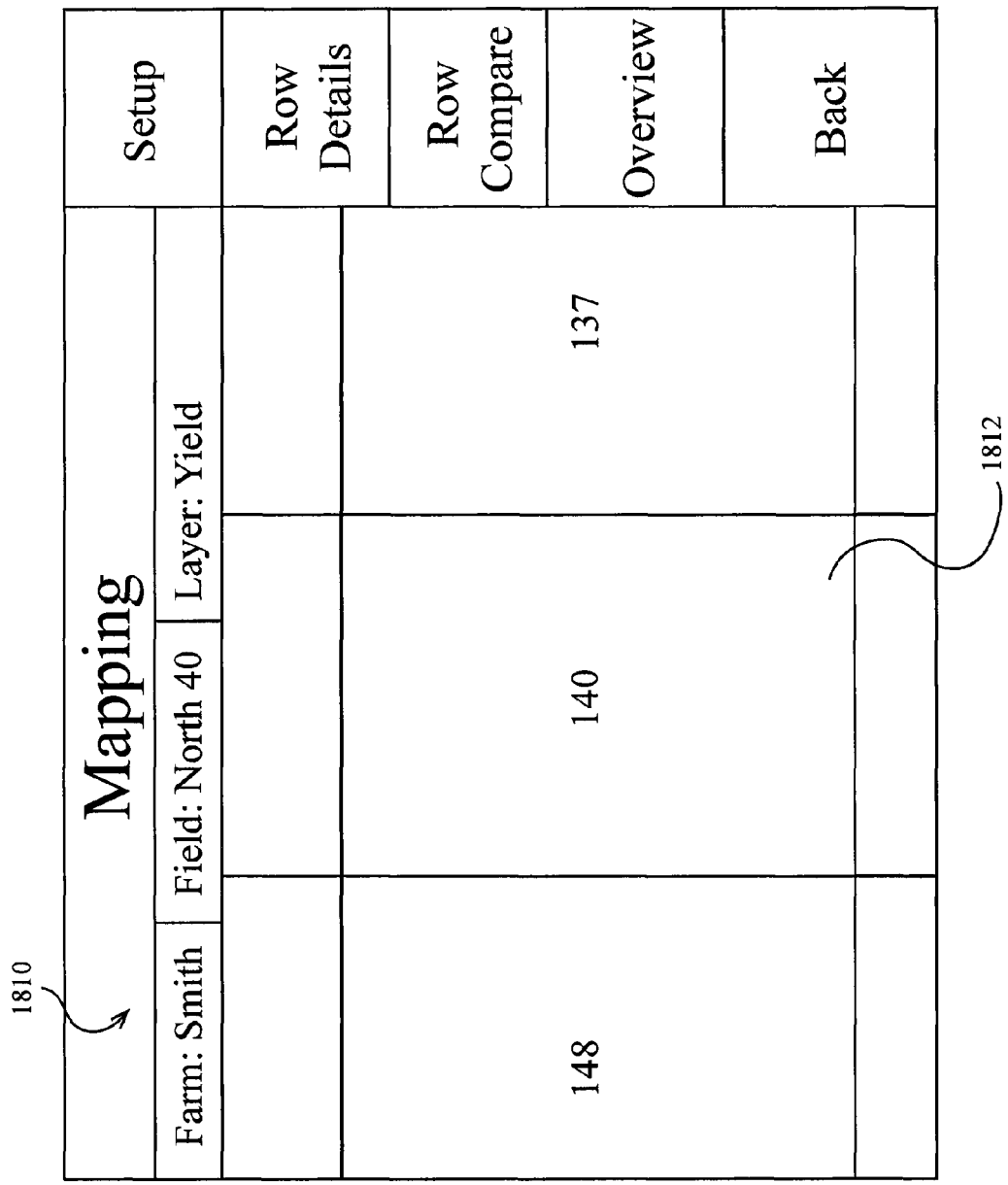
FIG. 23 illustrates the monitor screen of FIG. 22 displaying a yield map at a different zoom level.
Figure 24:
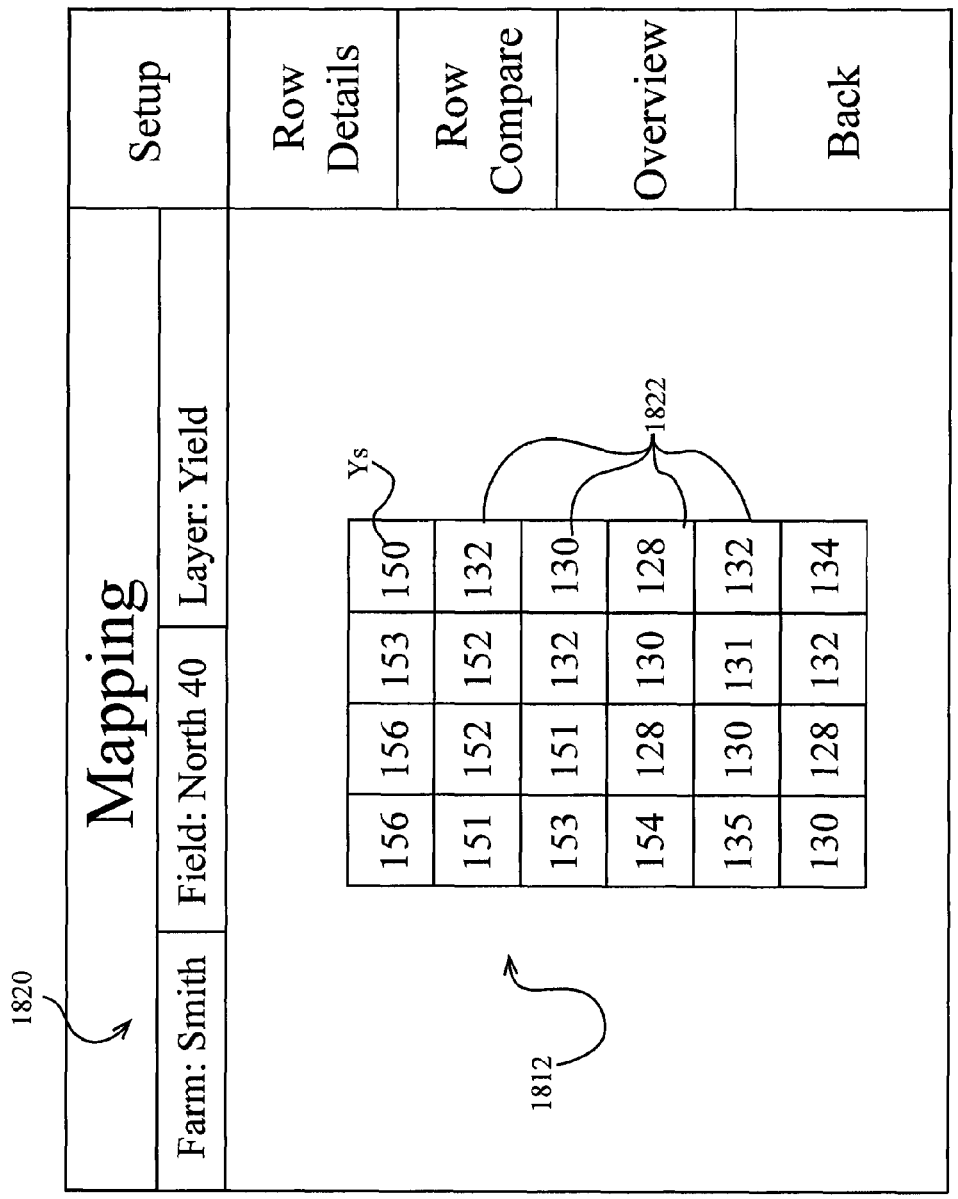
FIG. 24 illustrates another embodiment of a monitor screen displaying a yield map.
Figure 25:
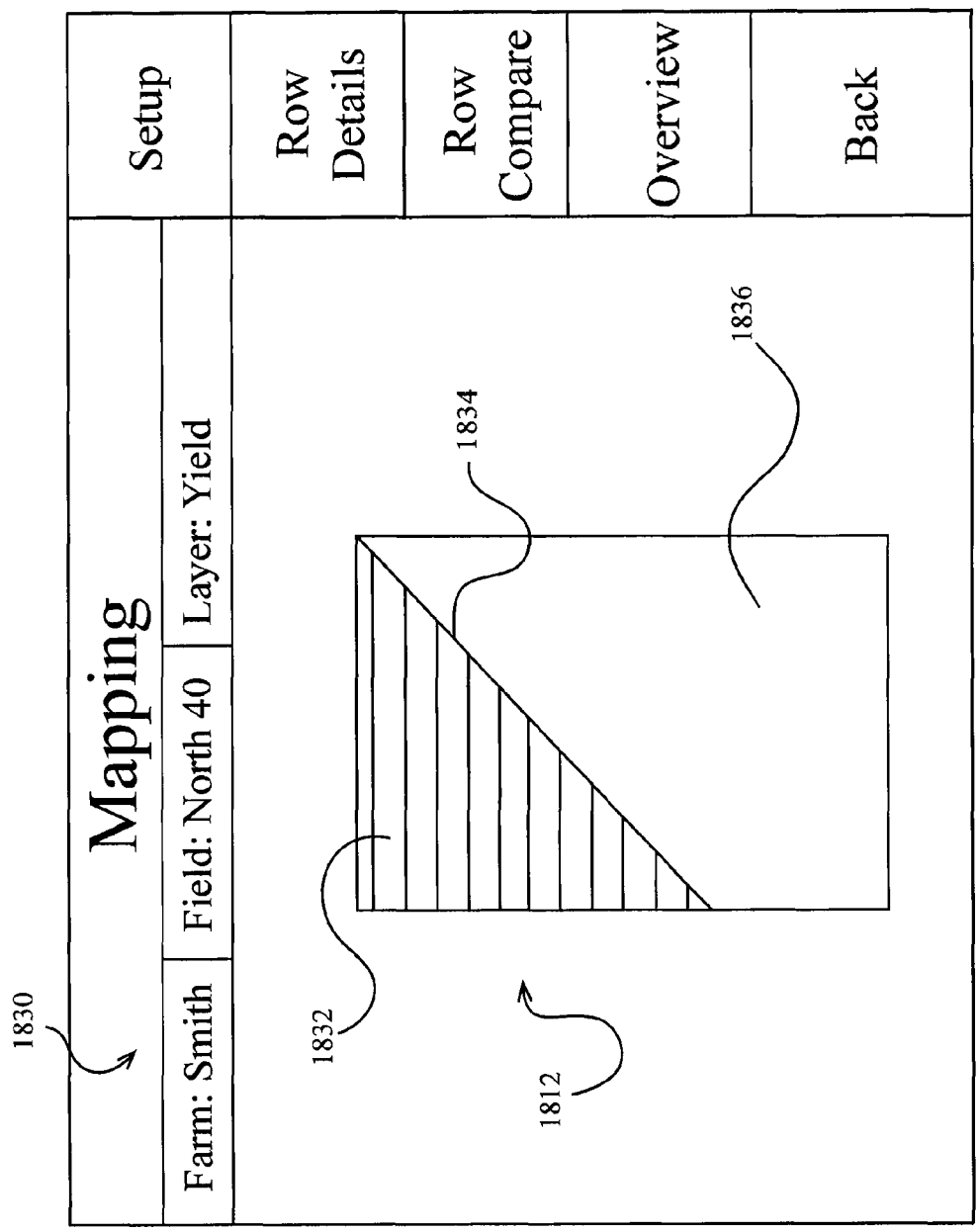
FIG. 25 illustrates another embodiment of a monitor screen displaying a yield map.

In FIG. 23, the yield map screen is zoomed in (using a magnification feature preferably provided by the harvest monitor 200) to the previously identified yield block 1812. Turning to FIG. 24, a screen 1820 preferably displays the yield block 1812 broken down into stalk blocks 1822, each having a spatial area associated with an individual stalk 25. The harvest monitor 200 preferably associates a stalk-specific yield value (referred to herein as stalk yield Ys) to each stalk block 1822, preferably denominated in bushels per acre. Turning to FIG. 25, a screen 1830 is illustrated in which the harvest monitor 200 uses the stalk-specific yield values to graphically depict the yield block 1812 as having multiple yield zones with different yield ranges (e.g., zone 1832 and zone 1836, separated by boundary 1834) rather than a single yield zone. In this way, the yield map 1810 is provided with increased resolution both along and transverse to the harvesting travel direction.

Figure 26:
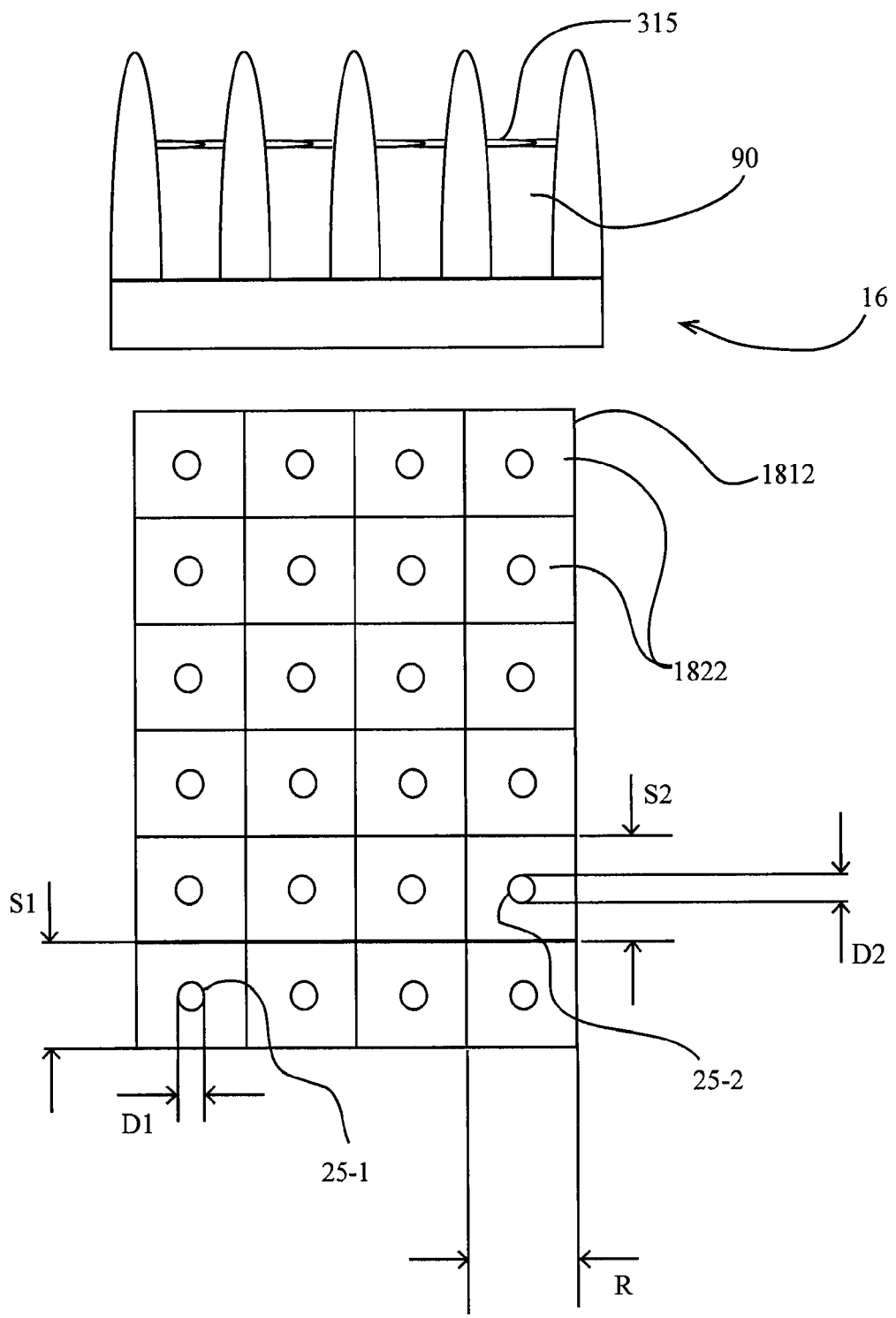
FIG. 26 is a schematic top view of a set of corn stalks divided into stalk blocks.

In order to break a yield block 1812 into stalk blocks 1822 with associated stalk yield estimates, the harvest monitor 200 preferably estimates the yield associated with each stalk 25 based on the diameter of the stalk. Referring to FIG. 26, each stalk 25 (e.g., 25-1 and 25-2) within the yield block 1812 has a measured diameter D (e.g., D1 and D2). Each stalk block 1822 has an area determined by the product of (a) the spacing S (e.g., S1 and S2) between the midpoints between the stalk 25 in the stalk block 1822 and the stalks subsequent and prior to the stalk and (b) the row spacing R between the rows of stalks.

Figure 27:
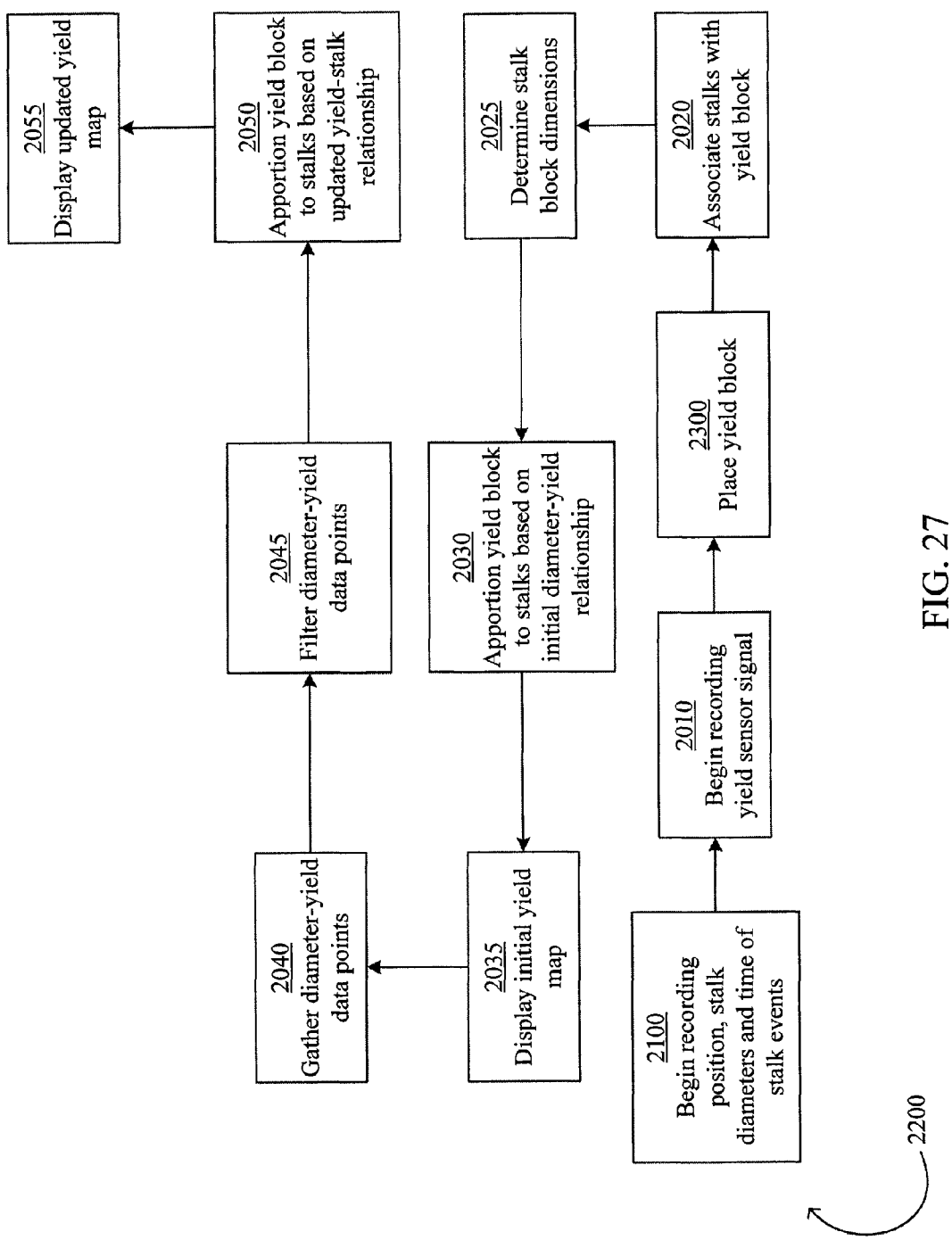
FIG. 27 is a process flow diagram illustrating an embodiment of a process for estimating yield.

A process 2200 for estimating the yield of each stalk is illustrated in FIG. 27. At step 2100, the monitor board 250 begins recording the position of and diameter of each stalk 25 as described herein with respect to FIG. 19. At step 2010, the monitor board begins recording the signal from the yield sensor 54 to generate a yield curve 3110 (FIG. 21). At step 2300 the harvest monitor 200 places a yield block 1812 on the yield map 1815 (FIG. 22) by mapping the area harvested by the corn head 16 during the recording period 21, and associates an average yield Yb with the stalk step 1812. At step 2020 the harvest monitor 200 associates stalks 25 with yield blocks 1812, preferably by determining whether the time t-s of each stalk event (e.g., times t-s1 through t-sn corresponding to stalks 25-1 through 25-n) falls between the extents t1 and t2 of the block recording period Tb (see FIG. 21). At step 2025, the harvest monitor 200 determines the dimensions R and S of each stalk block, preferably using the distance between recorded position of subsequent plants as well as the transverse row width.

Figure 28A:
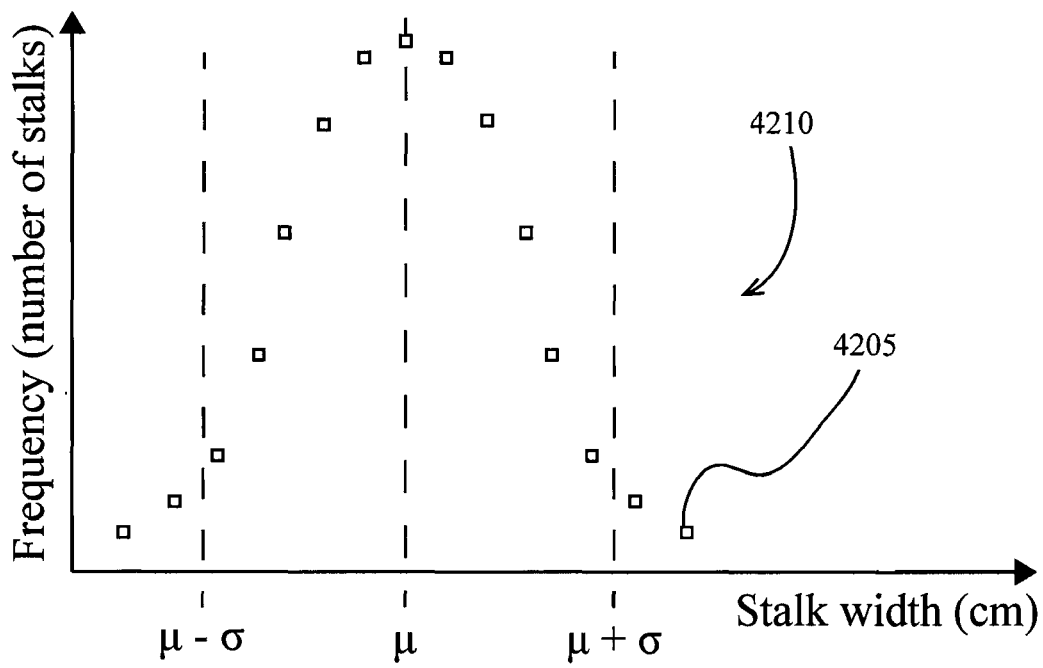
FIG. 28A is a stalk diameter histogram.
Figure 28B:
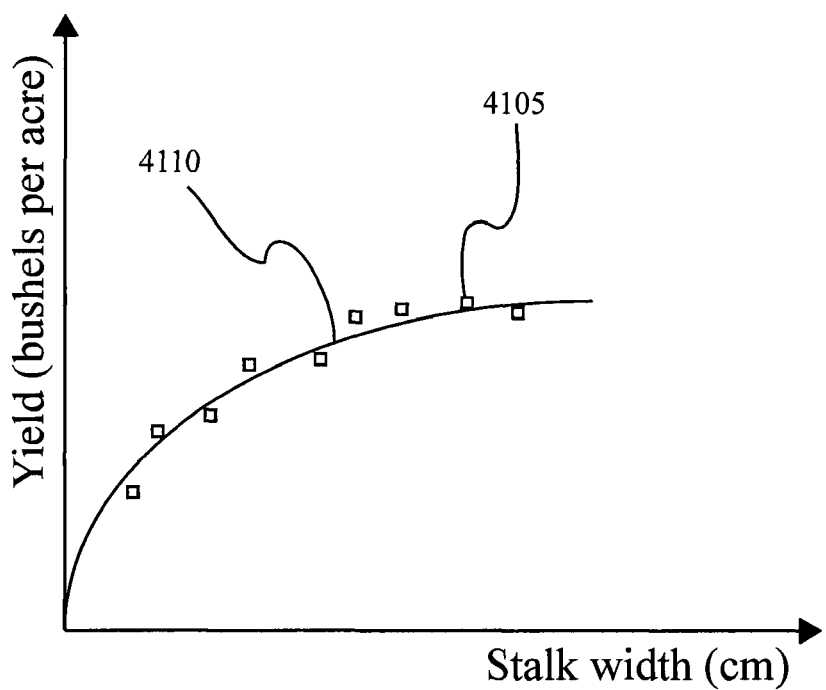
FIG. 28B is a plot of stalk diameter against yield.

Continuing to refer to FIG. 27 and the process 2200, at step 2030 the harvest monitor 2030 preferably apportions the yield Yb of the yield block 1812 based on a relationship between stalk diameter and yield. Such a relationship is illustrated in FIG. 28B, in which a characteristic 4110 relates stalk diameter to stalk yield. An initial characteristic 4110 is preferably determined empirically and pre-loaded into the memory of the harvest monitor 200; in some embodiments the harvest monitor may select between multiple pre-loaded characteristics appropriate for various hybrids, population rates and other variables.

Continuing to refer to step 2030, once the harvest monitor 200 has looked up an estimated yield value for each stalk 25 using the characteristic 4110, the harvest monitor 200 preferably scales all of the stalk yields in the stalk block 1812 so that the average of the estimated stalk yields is equal to the block yield Yb measured by the yield sensor 54. Thus the scaled individual stalk yield Ys-n of a stalk block 1822-n corresponding to a stalk 25-n in a stalk block 1812 having N stalks 25 of unscaled yield Ys may be represented by a relation such as $$Y_{s-n} = Y_s \frac{NYb}{\sum_{n=1}^{N} Yn}$$

Where:

$$Y_s = \frac{f(Ds)}{RS}$$

and f(Ds) is an empirical relationship such as the stalk diameter-yield relationship 4110 (FIG. 28B). At step 2035, the harvest monitor 200 preferably displays an initial yield map based on these yield estimates determined at step 2030.

In order to improve the yield relationship 4110 for the current field, the harvest monitor 200 preferably performs optional steps 2040 through 2055 of process 2200. At step 2040, the harvest monitor 200 gathers additional data points 4105 (FIG. 28B) in the diameter-yield relationship by recording the block yield Yb and an average stalk diameter Da for each yield block. At step 2045, the harvest monitor 200 preferably filters data points 4105 using a statistical criterion. FIG. 28A depicts a histogram 4210 in which each data point 4205 represents the number of stalks 25 in a given stalk block 1812 having a diameter within set of ranges. Using a statistical function as is known in the art, the harvest monitor preferably determines the standard deviation σ of stalk diameters for the yield block 1812 about the mean μ of the histogram. If the standard deviation σ of stalk diameters in a given yield block exceeds a certain threshold (e.g., 0.25μ or 0.5 cm) then the data point 4105 corresponding to the stalk block is preferably filtered out, i.e., not used to update the stalk yield-diameter relationship 4110. After a set of filtered data points have been acquired, at step 2050 the harvest monitor 200 preferably updates the yield-diameter relationship 4110 and repeats the step of step 2030 in order to update the stalk yields Ys based on the new yield-diameter relationship. At step 2055 the harvest monitor preferably displays an updated yield map based on the updated stalk yields Ys.

Harvest Information Screens

In addition to the yield map screen 1810, the harvest monitor 200 preferably displays multiple harvest information screens including row details screen 1200 such as that illustrated in FIG. 29, which illustrates the details of a specific row unit ("the active combine row") 90-1 of a four-row combine 10 (FIG. 18).

The row details screen 1200 preferably includes a planter row window 1210 which identifies the planter row (e.g., 12) that planted the row being harvested by the active combine row 90-1. The harvest monitor preferably compares the position and direction of the active combine row to the position and direction of the planter during each planter pass using the planting file to determine which planter pass corresponds to the pass of the active row. Once a planter pass has been identified, the harvest monitor 200 preferably compares the position of the active row to the range of positions of each planter row unit during the identified pass in order to determine which planter row unit planted the row being harvested by the active combine row unit.

The row details screen 1200 preferably includes a population window 1205 which displays the actual population determined by the stalk measurement system 100 and the as-planted population recorded during planting. The harvest monitor 200 preferably consults the planting file to determine the "as-planted" population for the population (either as-commanded or as-detected) corresponding to the location of the active combine row. The harvest monitor 200 preferably determines the "actual" population by counting the stalks 25 sensed by the stalk sensor 300 of the active row over a predetermined travel distance (e.g., 30 feet) and multiplying by the row spacing R (FIG. 26). The step of counting the stalks 25 is preferably accomplished by adding a value (e.g., 1) to a stalk count stored in the memory 204 when the presence of a stalk is verified (e.g., by recording a stalk diameter above a minimum threshold such as 0.3 inches). The stalk count is preferably associated with the predetermined travel distance prior to the current location of the combine. The stalk count is also preferably associated with a region in the field being harvested. It should be appreciated that where the stalk count is used to determine the actual population, the actual population comprises a harvest metric based on the stalk count.

The row details screen 1200 preferably includes an emergence window 1215 that displays the percentage of seeds planted that emerged into harvestable stalks. The harvest monitor preferably determines the emergence percentage by dividing the actual population by the as-planted population (both of which may be determined as described above with respect to the population window 1205).

The row details screen 1200 preferably includes a spacing window 1245 that displays an "actual" spacing criterion representing the consistency of spacing between plants in the active row as measured by the stalk measurement system 100, an "as-planted" good spacing criterion, as well as the number of "doubles" (seeds planted close together) and "skips" (gaps without seed placement) detected by the stalk measurement system 100. The actual spacing criterion may be measured using the methods of recording and counting misplaced seeds disclosed in Applicant's co-pending U.S. patent application Ser. No. 12/522,252 (Publication No. 2010/10667) ("the '252 application"), the disclosure of which is hereby incorporated herein in its entirety by reference. but measuring the times between the stalk locations detected by the stalk sensor 300 rather than the times between seed placement locations determined by a planter seed sensor. The "as planted" good spacing criterion, the percentage of doubles, and the percentage of skips for the current position in the field may be obtained from the planting file for the relevant planter row determined as described with respect to planter row window 1210.

The row details screen 1200 preferably includes a stalk width window 1240 that displays the current stalk width average of the most recent group of detected stalks and the average stalk width for the field. The stalk measurement system 100 records the diameters of the stalks as described herein with respect to FIG. 19. To determine the current stalk width average, the stalk measurement system 100 calculates the average of the most recent calculated diameters (e.g., the diameters of the previous 50 stalks). The size of the group is preferably adjustable by the user in a setup phase. To determine the field stalk width average, the stalk measurement system associates stalks to the current field (e.g., by comparing the stalks to a field boundary provided by the user in a setup phase) and calculates the average diameter of the stalks in the field. The illustrated indications in the stalk width window 1240 related to "full-ear" stalk width are discussed later herein.

Figure 30:
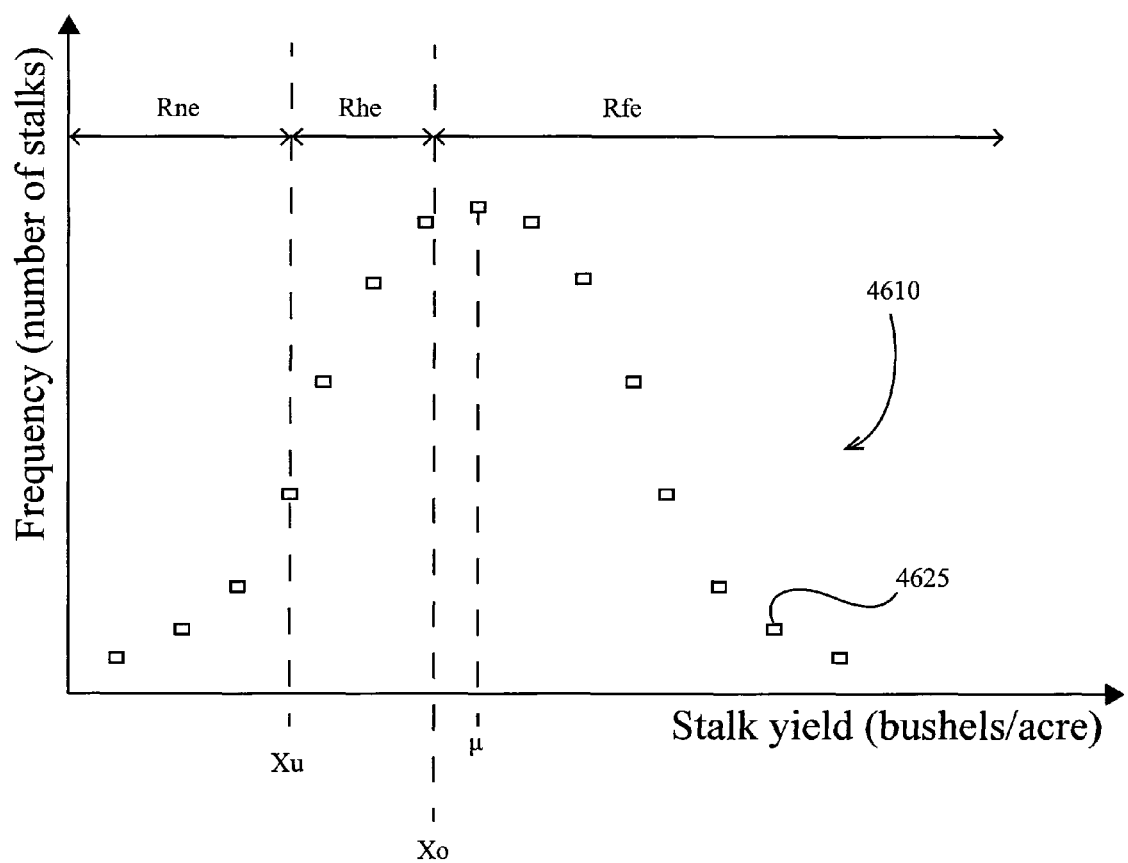
FIG. 30 is a stalk diameter histogram.

The row details screen 1200 preferably includes a current ears window 1225 that displays the number of "full-ear" stalks, "half-ear" stalks, and "no-ear" stalks in the last group of harvested stalks (e.g., the previous 30 stalks). Turning to FIG. 30, a histogram 4610 of the most recently measured stalks is illustrated in which each data point 4625 represents the number of stalks having a stalk yield within a particular range. The stalk yield of each stalk is determined as described herein with respect to FIG. 27. The harvest monitor 200 preferably includes empirically determined thresholds Xu and Xo in memory which define three regions Rne, Rhe, and Rfe. The harvest monitor preferably categorizes stalks having stalk yields Ys within regions Rne, Rhe, and Rfe as having no ear, a half ear, and a full ear, respectively. The percentages displayed in current ears window 1225 preferably correspond to the percentages of ears in the last group of ears cagegorized as no-ear, half-ear and full-ear stalks. The thresholds Xu and Xo may comprise any of the following: multiples or fractions of the standard deviation σ added to or subtracted from the mean μ, multiples or fractions of the mean μ, or constant numerical yield minimums corresponding to minimum-sized "full ears" and "half ears," respectively.

Returning briefly to the stalk width window 1240, the stalk width corresponding to the "full-ear" stalk yield discussed above is preferably displayed therein. The harvest monitor 200 preferably determines the full-ear stalk diameter by consulting a yield-diameter relationship such as the characteristic 4110 described with respect to FIG. 28B. The mean stalk width t is preferably divided by the "full-ear" stalk width and the result is preferably displayed as the percentage of "full-ear" stalk diameter (e.g., 94%) in the stalk width window 1240.

The row details screen 1200 preferably displays an ear count window 1212 in which the total number of ears per acre Et is displayed, e.g., $$Et = \frac{\Sigma Yn}{(Yfe)(R)(Lg)}$$

Where:
R is the transverse row spacing;
Lg is the length along the direction of travel of the group of stalks (e.g., 50) over which the number of half-ears ears is counted;
Yfe is the full-ear stalk yield.

The row details screen preferably displays a stalk variation window 1235 that displays the variation in stalk width. The stalk variation (e.g., 0.07 inches in FIG. 29) is preferably related to a statistical indication of the variation in stalk width for the previous group of stalks (e.g., 50 stalks) in the active combine row. In the illustrated example, the harvest monitor 200 calculates the standard deviation $\sigma$ (FIG. 28A) of stalk diameters and displays the value of $\sigma$ as the stalk variation in inches. The harvest monitor 200 also preferably calculates the mean stalk width t and displays the percentage of variation from the mean, i.e., $100(\sigma/\mu)$ (e.g., 9% in FIG. 29).

The row details screen 1200 preferably includes a yield contribution window 1230 which displays the contribution of the active combine row to the total yield currently reported by the yield sensor 54. To calculate a row yield contribution percentage Ycn for a given row unit 90-$n$ in a combine having N rows, the harvest monitor 200 preferably first averages the stalk yield Ys from the last group of stalks (e.g., 50) for each row unit 90-$n$ of the combine head to obtain an average row yield Yn for each row and then uses the relation:

$$Ycn = 100\frac{NYn}{\sum_{1}^{N} Yn}$$

It should be appreciated that the yield contribution percentage Ycn comprises harvest data (or a "harvest metric") based on the stalk diameters measured by the stalk measurement system 100.

The row details screen 1200 preferably includes an economic loss window 1255 which preferably displays a total planting-related economic loss and a correlation of economic loss to a variable representing a specific planting process characteristic or error. Such variables preferably include margin (downforce on row unit gauge wheels in excess of that required to ensure proper planting depth), ground contact percentage (the percentage of time in which proper planting depth is ensured), or compaction from planter tires adjacent to the active row; other variables are discussed in detail in the '252 application.

Figure 32:
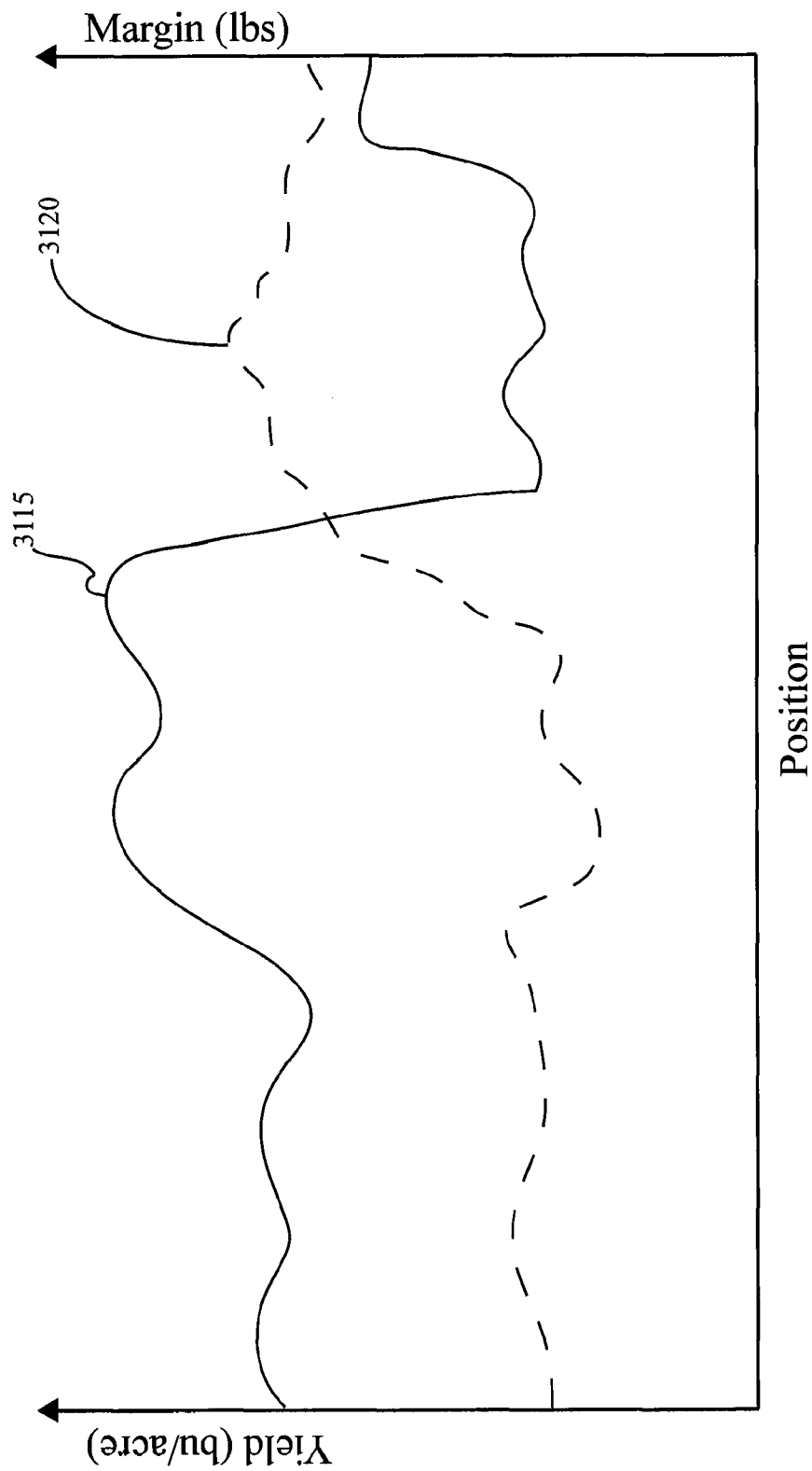
FIG. 32 is a plot of yield and a planting variable over time.

Turning to FIG. 32, row-specific planting-related data (e.g., margin data set 3120) obtained from the planting file may be compared over the same range of positions in which a row-specific yield data set 3115 is obtained by the stalk measurement system 100. The row-specific yield data set 3115 may be generated by associating the stalk yield (determined as discussed elsewhere herein) with the location of each respective stalk.

Figure 31:
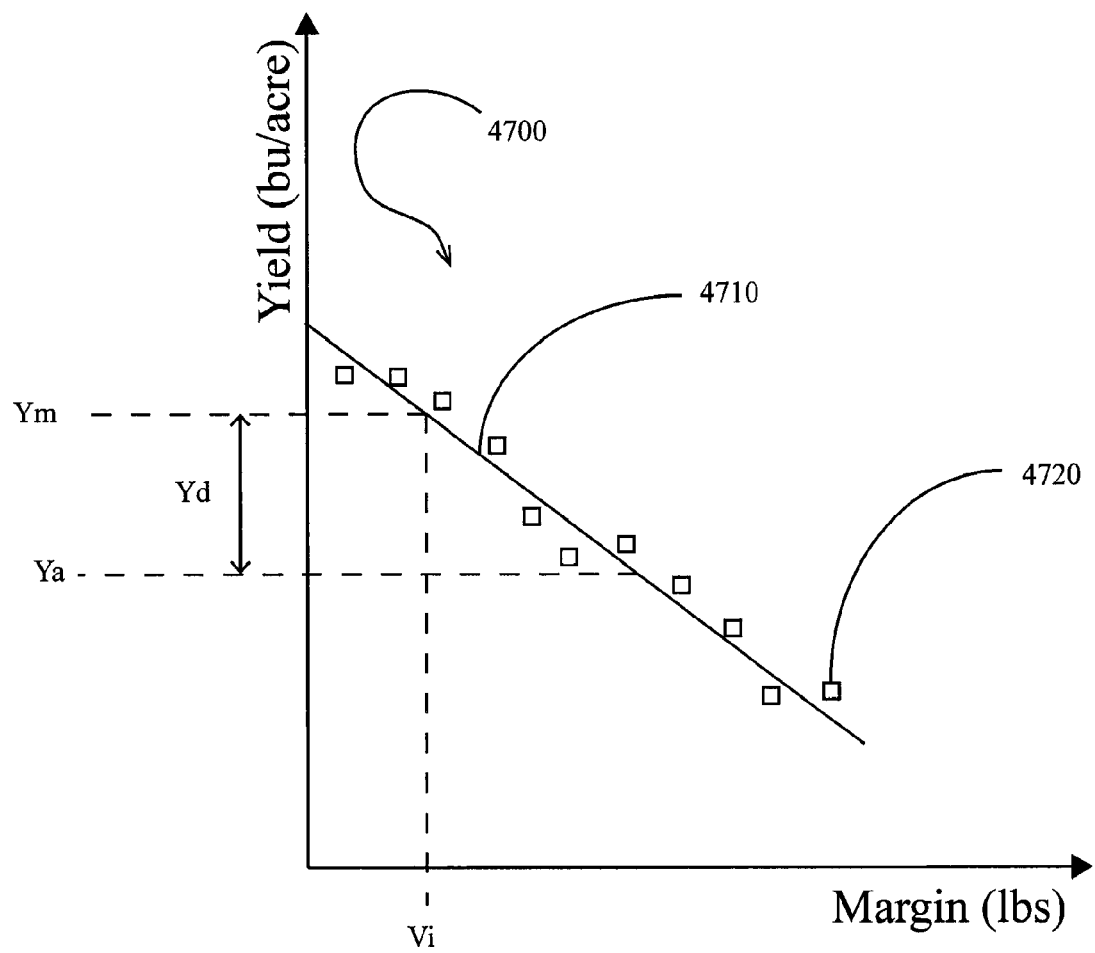
FIG. 31 is a plot of yield against a cultivation variable.
Figure 33:
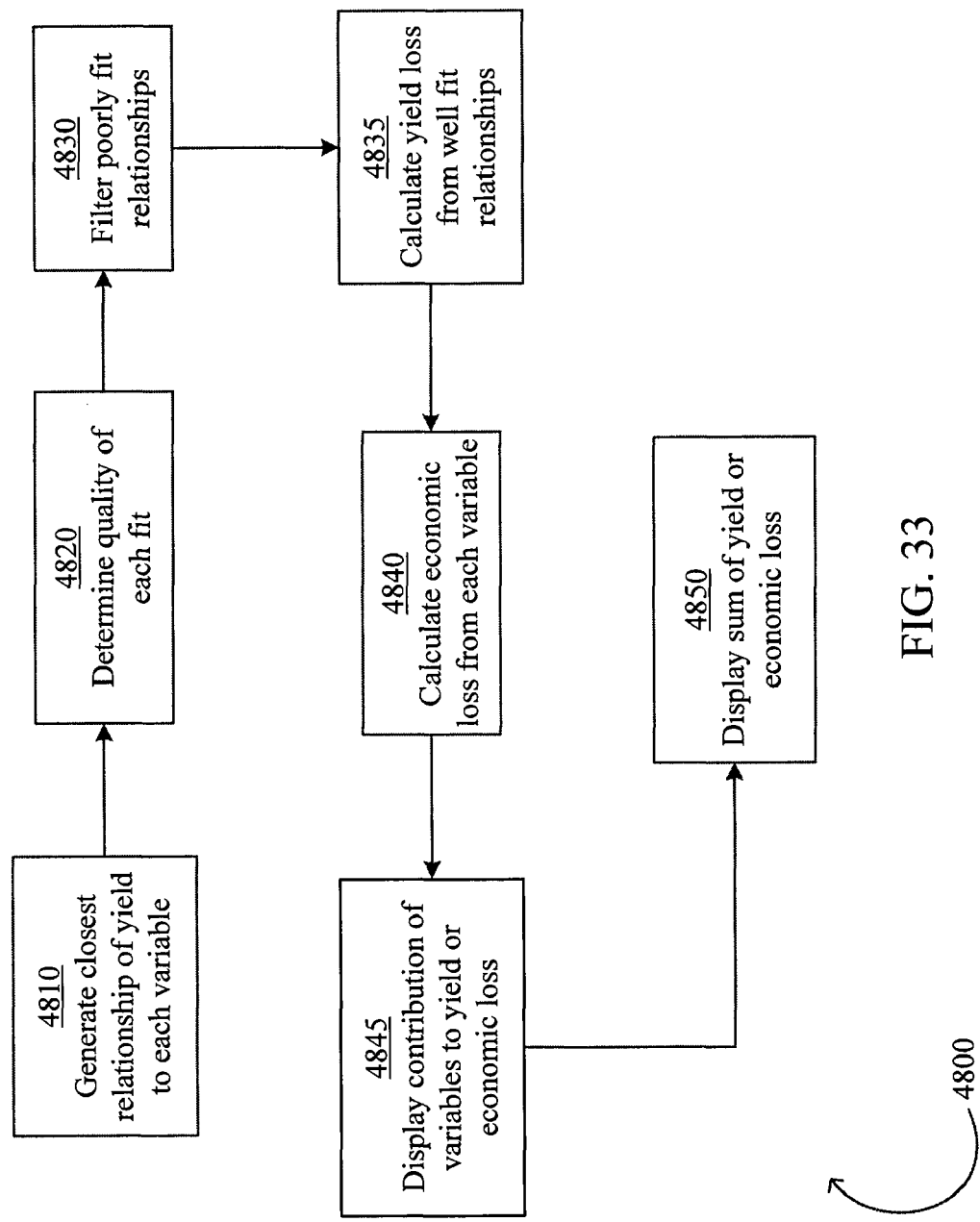
FIG. 33 is a process flow diagram illustrating an embodiment of a process for determining yield loss and economic loss from cultivation variables.

Turning to FIG. 31, each planting-related data set (e.g., margin data set 3120) may be used with the yield data set 3115 to generate a correlation data set 4700 consisting of data points 4720. It should be appreciated that yield data from multiple rows may be used to develop such a correlation. Turning to FIG. 33, a process 4800 for determining economic loss from such a correlation data set is illustrated. At step 4810, the harvest monitor 200 preferably determines the closest relationship (e.g., relationship 4710 in FIG. 31) using least squares regression or other curve-fit methods known in the art. It should be appreciated that the relationship 4710 may be of any power including first-, second- or third-order, and the harvest monitor 200 may also include a limitation in memory of the maximum order relationship to be used to correlate a particular variable to yield. At step 4820, the harvest monitor 200 preferably determines the quality of fit (e.g., the r-squared value) between the relationship 4710 and the correlation data set 4700 for each variable. At step 4830, the harvest monitor 200 preferably compares the quality of fit for each variable to a minimum threshold (e.g., an r-squared value of 0.8) such that relationships whose fit quality is less than the applicable minimum threshold are ignored.

At step 4835, the harvest monitor 200 preferably calculates a positional yield loss Yd associated with each variable having a relationship that passed the filtering step of step 4830. Briefly returning to FIG. 31, this step may be accomplished by determining a theoretical maximum yield Ym associated with an ideal value Vi of the variable (e.g., one pound of margin), determining an actual yield Ya associated with the current position in the field, and determining a yield loss Yd represented by the difference between the maximum yield Ym and the actual yield Ya. At step 4840, the harvest monitor 200 preferably calculates an economic loss associated with each variable by multiplying the yield loss Yd by a pre-loaded commodity price. At step 4845, the harvest monitor preferably displays the contribution of variables to the total yield or economic loss attributable to the planting process. For example, the loss correlation bar 1250 in population window 1255 (FIG. 29) provides a visual indication of the variables correlated to yield loss and their relative contribution to yield loss; in FIG. 29, the loss correlation bar illustrates that tire tracks, margin and ground contact are respectively the largest, second-largest, and third-largest causes of yield loss, respectively. The loss correlation bar 1250 preferably does not display variables whose correlation to yield was filtered out at step 4830. At step 4850, the harvest monitor preferably displays the sum of economic or yield loss attributable to the planting process; in FIG. 29, the total economic loss is $2.51 per acre.

Figure 34:
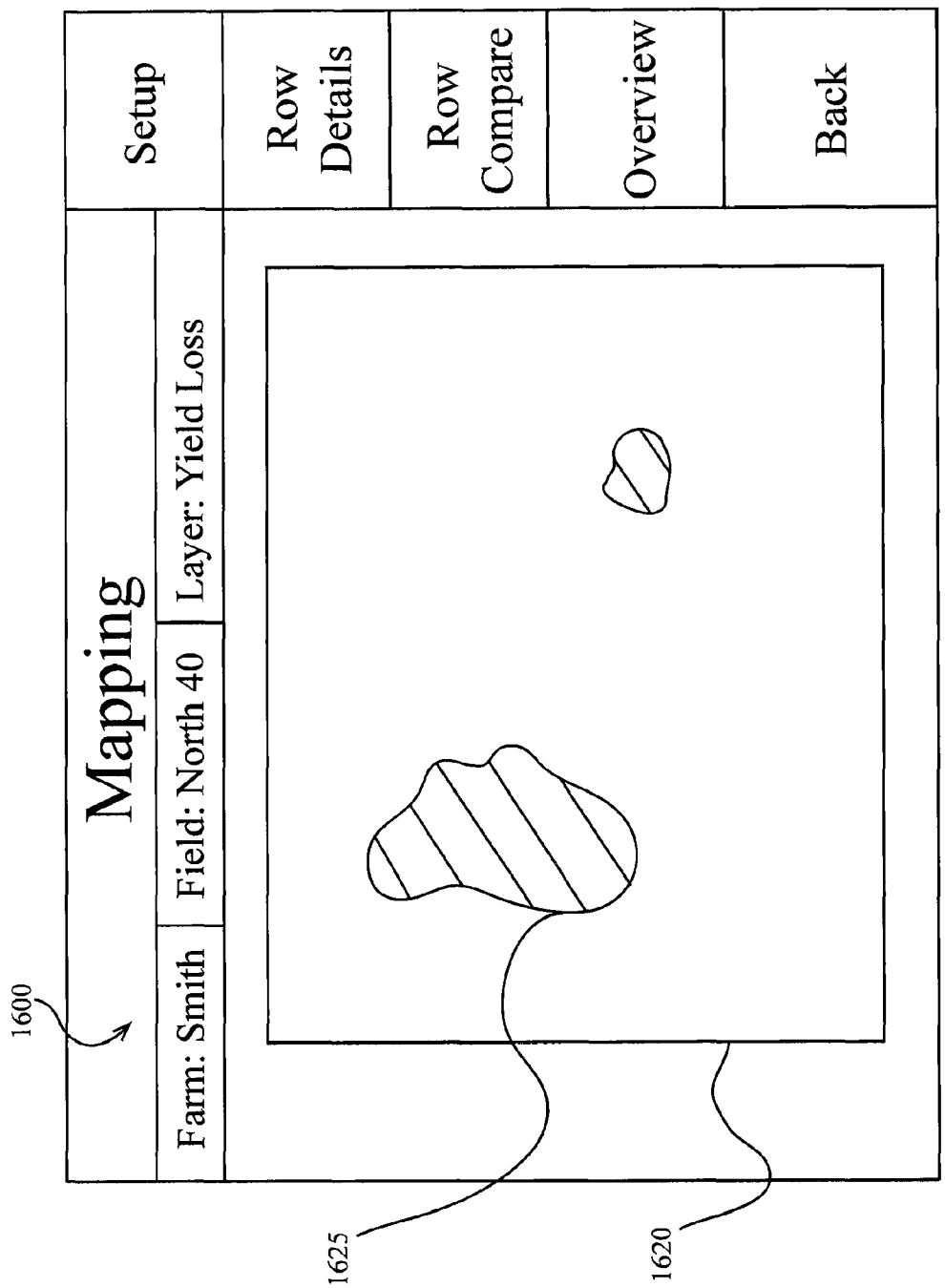
FIG. 34 is an embodiment of a monitor screen display for displaying yield loss map.
Figure 35:
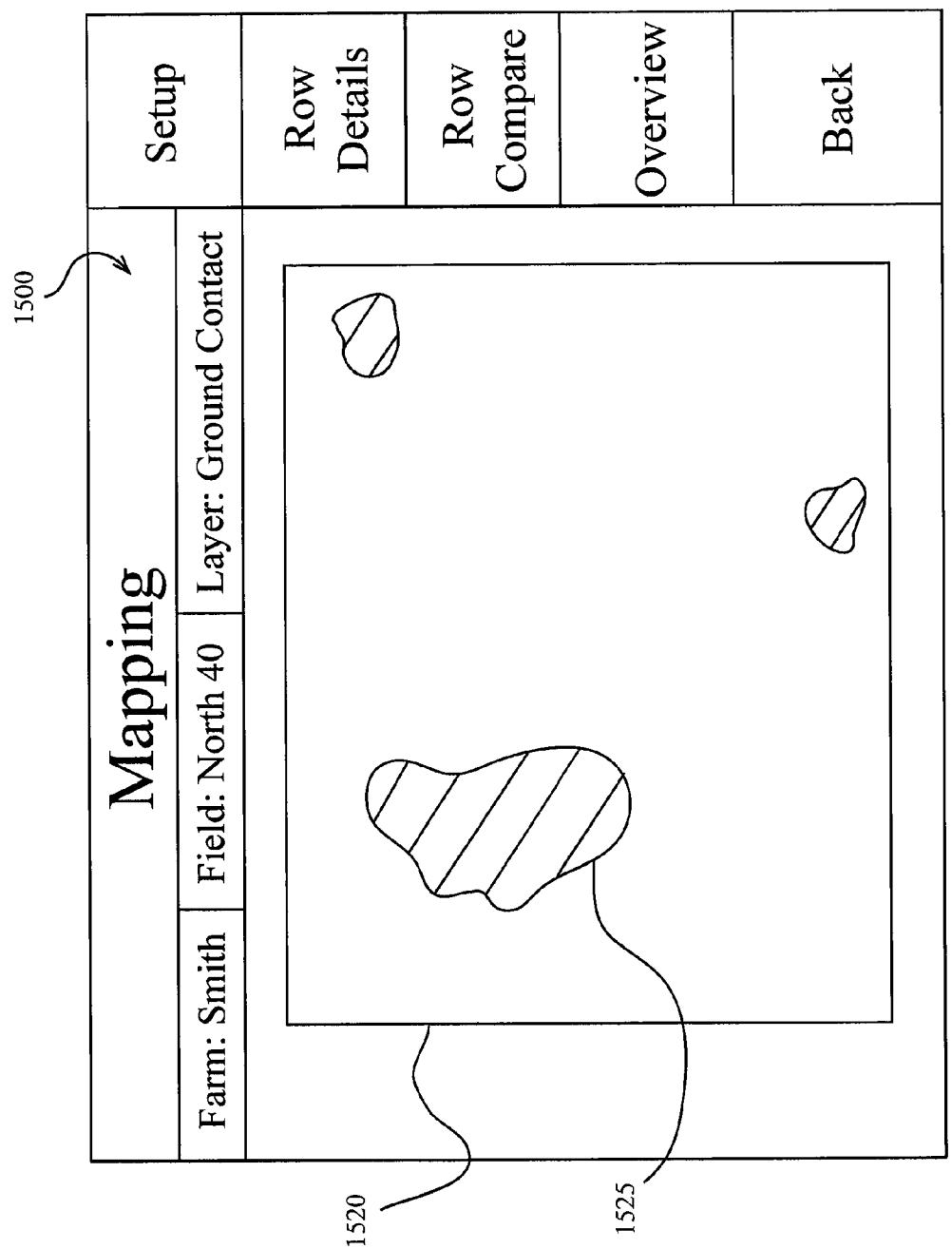
FIG. 35 is an embodiment of a monitor screen display for displaying a cultivation variable map.
Figure 36:
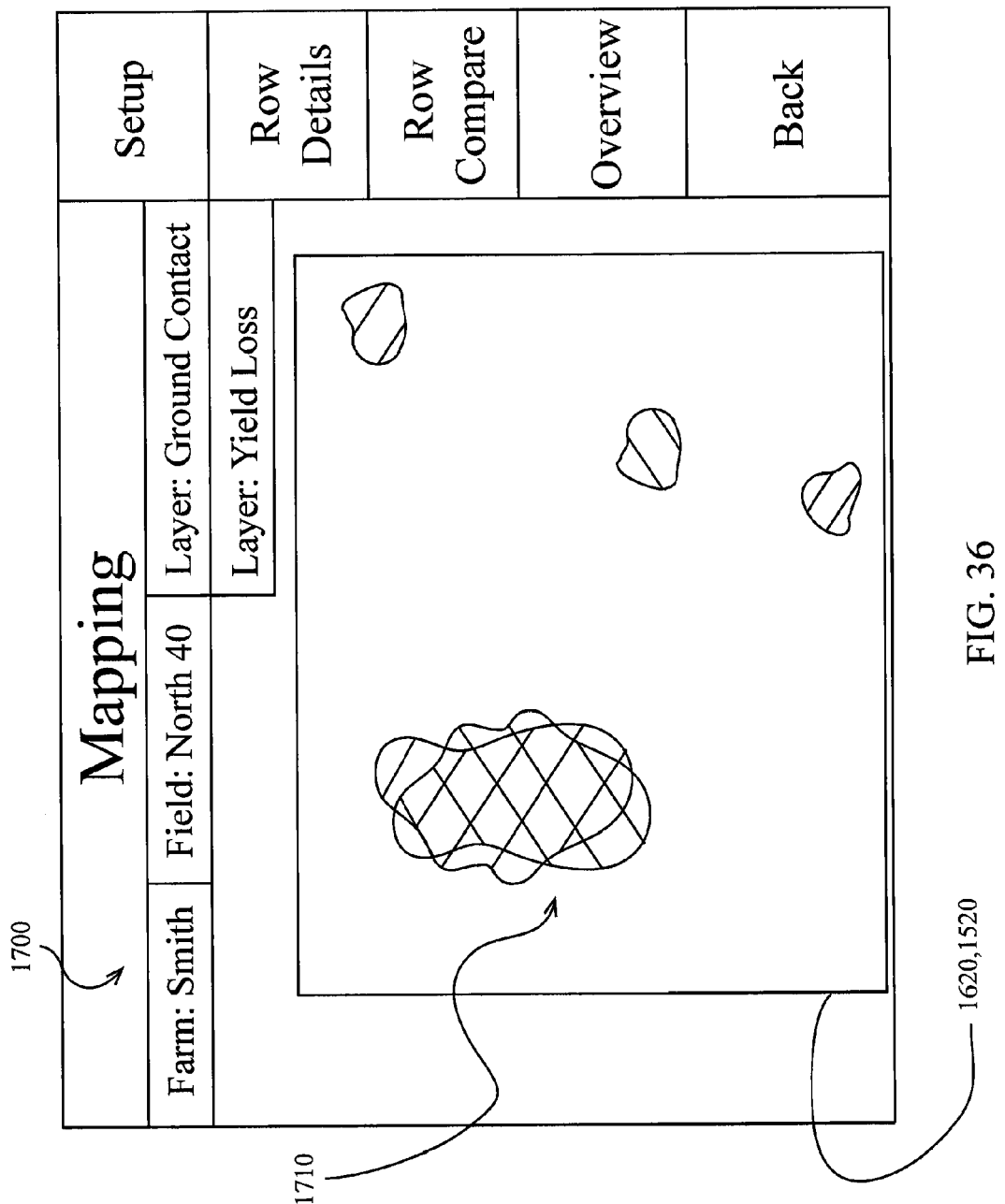
FIG. 36 is an embodiment of a monitor screen display for displaying a yield loss map layered with a cultivation variable map.

In some embodiments, the correlation between planting process variables and yield loss is displayed spatially to the user. Referring to FIG. 34, map screen 1600 displays a field map 1620 including yield loss polygons 1625. Yield loss polygons 1625 are preferably generated by including each area of the field in which the total yield loss exceeds a threshold value (e.g., 10 bushels per acre). Referring to FIG. 35, a map screen 1500 displays a field map 1520 including ground contact loss polygons 1525. Ground contact loss polygons 1625 may be generated by including each area of the field in which the planter row unit ground contact was less than a threshold value (e.g., 80%). Turning to FIG. 36, map screen 1700 displays both field maps 1520 and 1620. A region 1710 of spatial overlap between polygons 1625 and 1525 displays an area of correlation between ground contact and yield loss to the operator. It should be appreciated that different hatching, coloring, or shading of polygons may be used to indicate areas of overlap to the user. In addition, polygons 1625,1525 may be shaded to represent increasing levels of yield loss and ground contact loss such that the shading of overlap region 1710 represents the strength of correlation between ground contact and yield loss.

Turning to FIG. 37, an overview screen 1100 is illustrated. The overview screen includes a population window 1115, a stalk width window 1105, an emergence window 1110, an economic loss window 1120, a stalk variation window 1130, and a field ears window 1135, which apply the algorithms used in the corresponding row detail windows (described herein with respect to FIG. 29) to data from all rows rather than a single row. The overview windows also preferably display which row currently at which the highest and/or lowest value of the relevant criterion is measured; for example, the emergence window 1110 displays the overall emergence percentage for all rows, the row number (2) of the row exhibiting the lowest emergence percentage, as well as the emergence percentage (88%) for that row. In addition, the yield window 1125 preferably displays the current yield being reported by the yield sensor 54 as well as the high and low row yield contributions.

Figure 38:
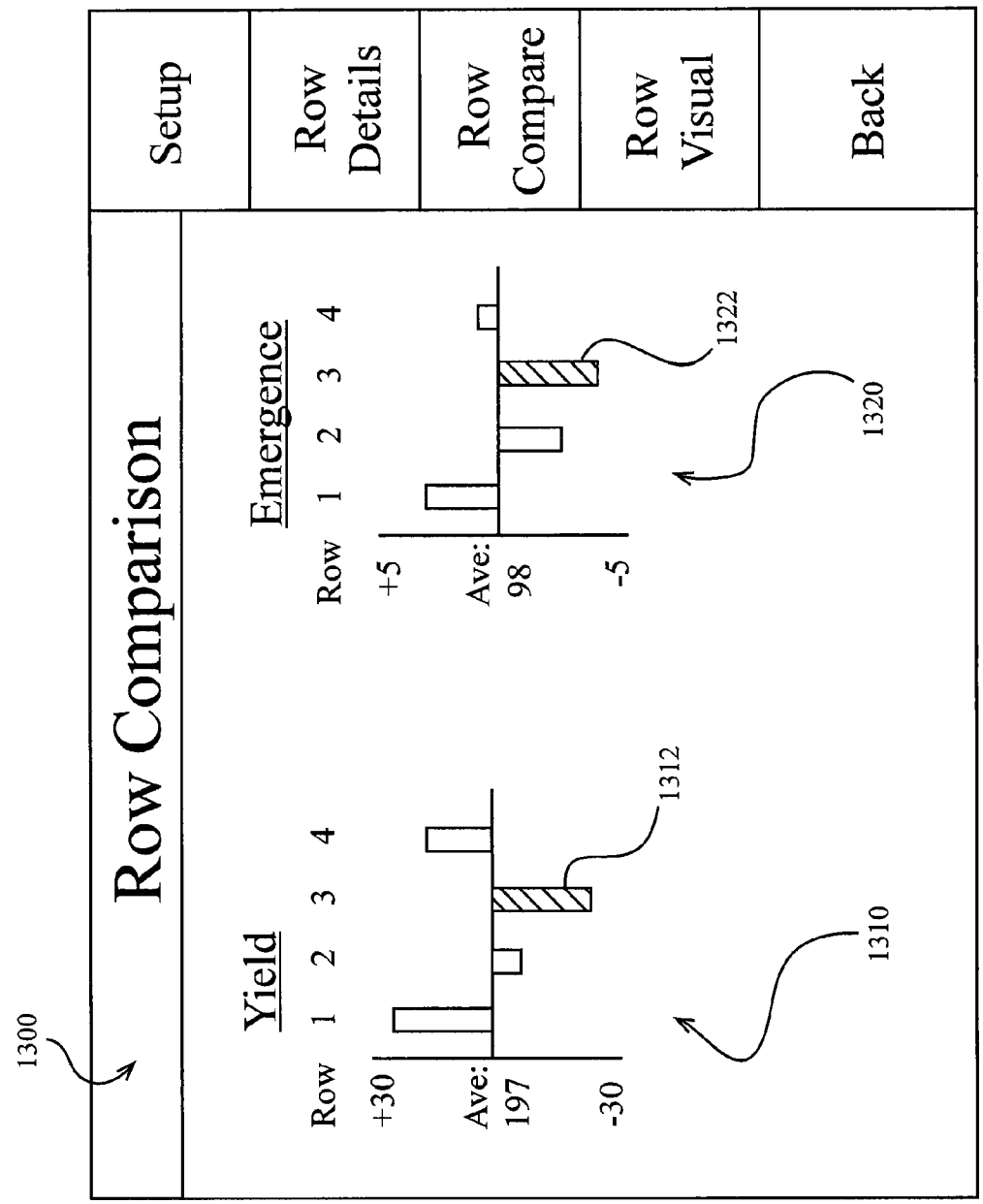
FIG. 38 is an embodiment of a monitor screen display for displaying a comparison of harvest data between multiple rows.

In addition to displaying the high and low row values as described above with respect to FIG. 36, the harvest monitor 200 preferably displays a row-by-row comparison for various harvest criteria. Turning to FIG. 38, a row comparison screen 1300 preferably includes yield row comparison 1310 and an emergence row comparison 1320. Bars 1312,1322 visually illustrate the variation of the criterion for the row unit from the average value for all the row units. Hatching of the bars labeled 1312,1322 visually indicates that the associated row exhibits the most negative variation of the criterion from the average.

Figure 39:
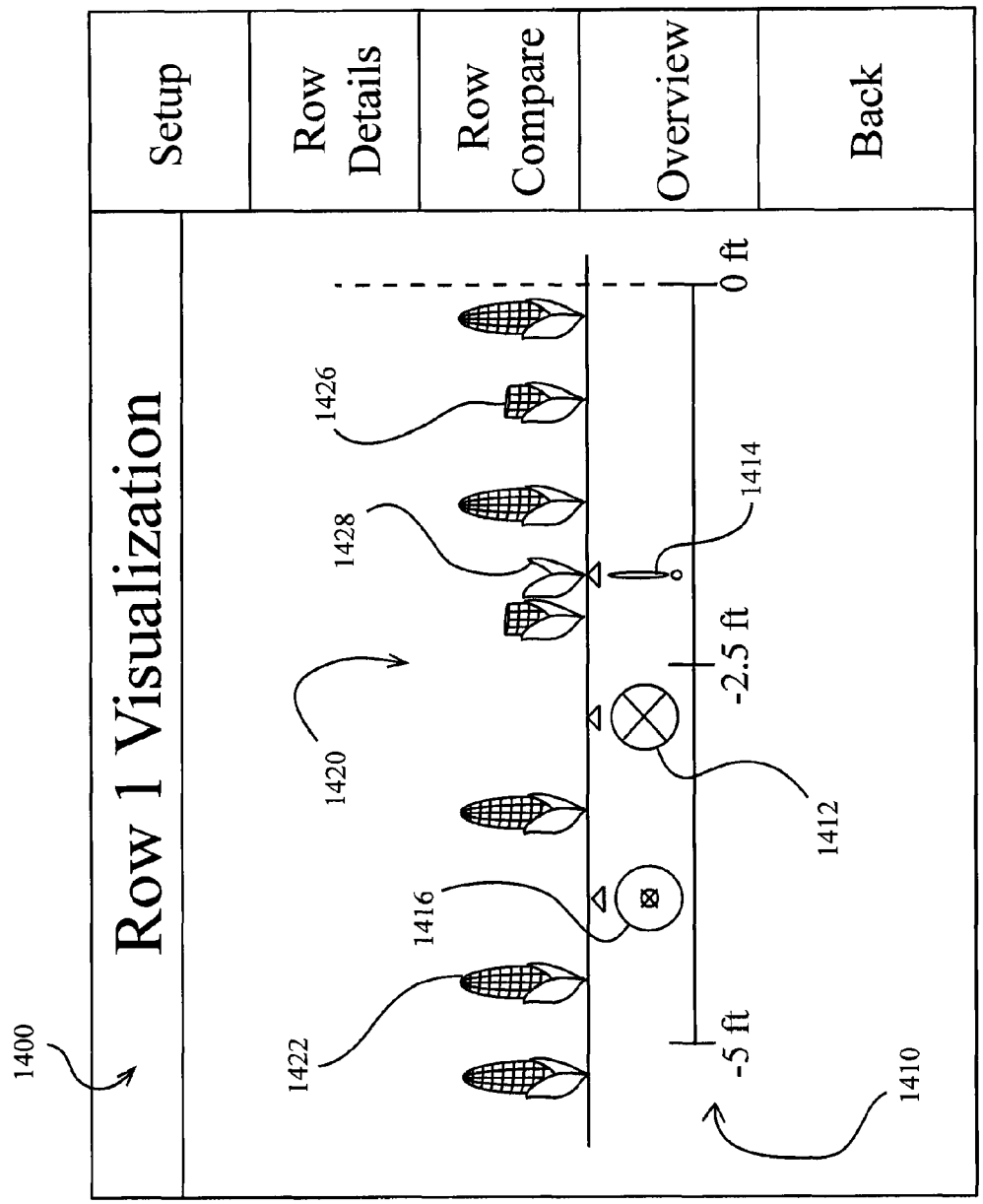
FIG. 39 is an embodiment of a monitor screen display for displaying a visualization of harvest data for a row.
Figure 40:
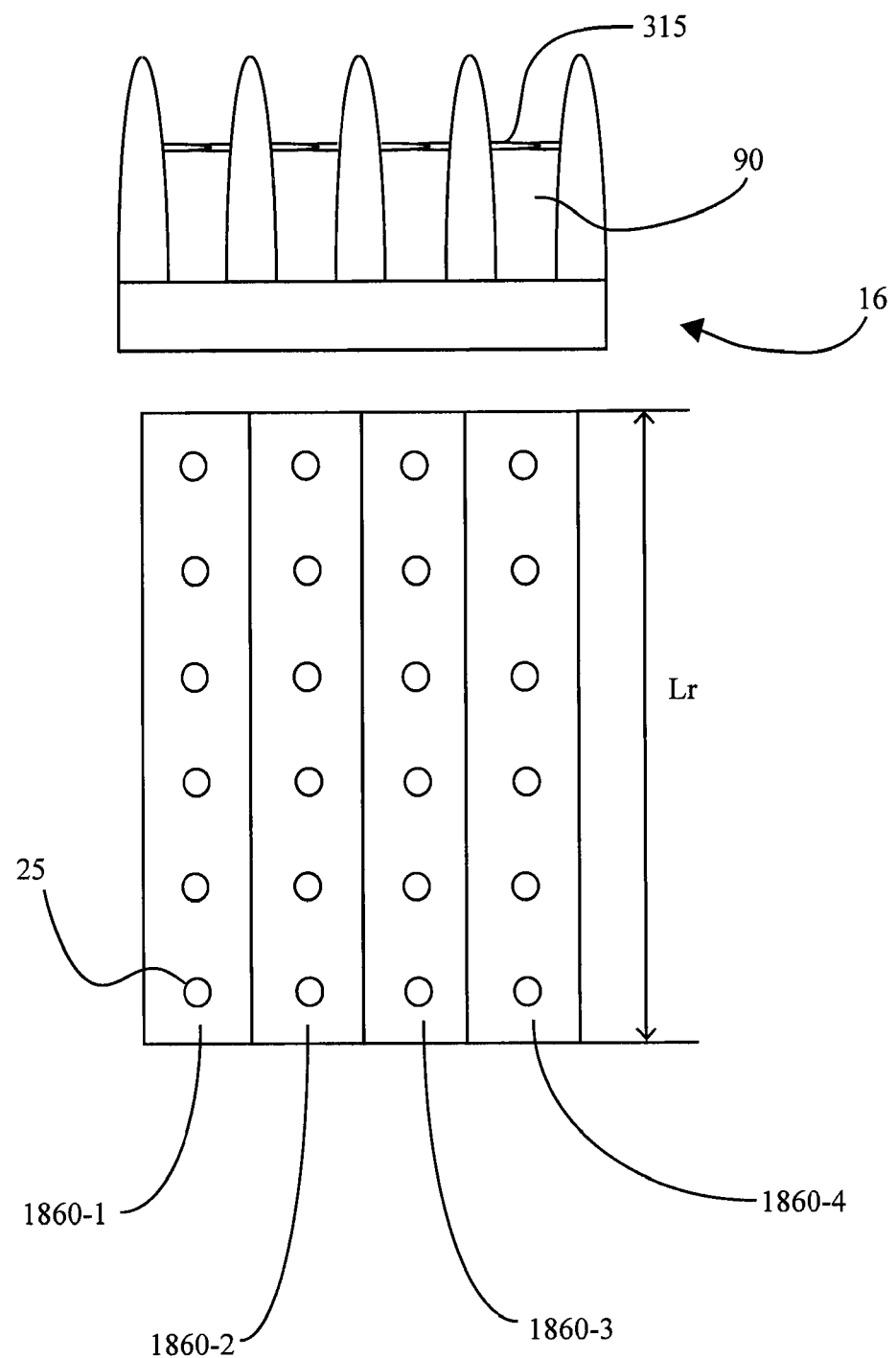
FIG. 40 is a schematic top view of a set of stalks divided into row blocks.

Turning to FIG. 39, the harvest monitor 200 preferably displays a row visualization screen 1400 visually illustrating stalk spacing and ear quality for individual rows. The visualization screen 1400 includes a row illustration 1420 in which full-ear pictograms 1422, half-ear pictograms 1426 and no-ear stalk pictograms 1428 illustrate the location along a scale 1410 at which a stalk with yields corresponding to full ears, half-ears and no-ear stalks, respectively. The position of each pictogram along scale 1410 preferably corresponds to the current distance by which the stalk sensor 300 has passed the stalk 25 associated with the pictogram. Skip pictogram 1412 indicates locations at which a skip occurred during planting. Emergence failure pictogram 1416 indicates a location in which a seed was planted according to the planting file but failed to emerge according to the stalk sensor 300. Empty stalk pictogram 1414 comprises an alarm indicating a no-ear stalk.

Alternative Stalk Measurement Apparatus and Methods

Figure 42:
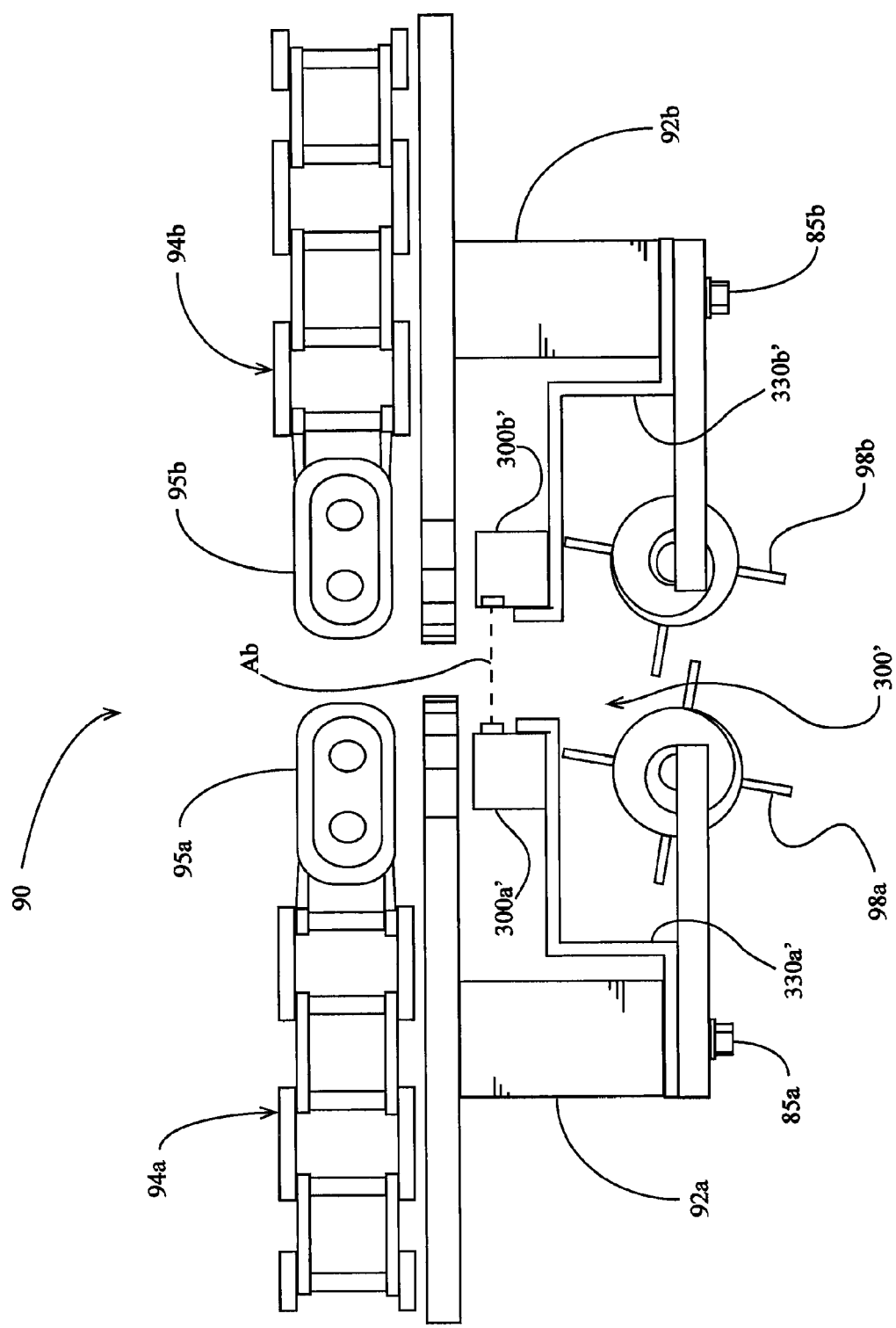
FIG. 42 is a front view of a combine row unit with an embodiment of an optical stalk sensor mounted thereto.

In other stalk measurement system embodiments, alternative stalk measurement devices are used report data to the user as disclosed herein. For example, an optical stalk measurement device 300' is illustrated in FIG. 42 installed in combine row unit 90. The optical stalk measurement device 300' includes an emitter 300a' mounted to a bracket 330a' and a receiver 300b' mounted to a bracket 330b'. In other embodiments the stalk measurement device 300' may be mounted to the undersides of the stripper plates 93. The emitter 300a' and receiver 300b' may comprise a Mini-Beam emitter Model No. SM31EL and Mini-Beam receiver Model No. SM31RL available from Banner Engineering in Minneapolis, Minn. The brackets 330 are mounted between frame portions 92 and floor portions 86 of the row unit 90. The emitter and receiver 300a',300b' are disposed such that light emitted along an axis Ab from the emitter is received by an infrared sensor in the receiver. The receiver 300b' is preferably configured to generate a signal proportional to the intensity of light provided by the emitter 300a'. The receiver 300b' is preferably in electrical communication with the monitor board 250.

Figure 43:
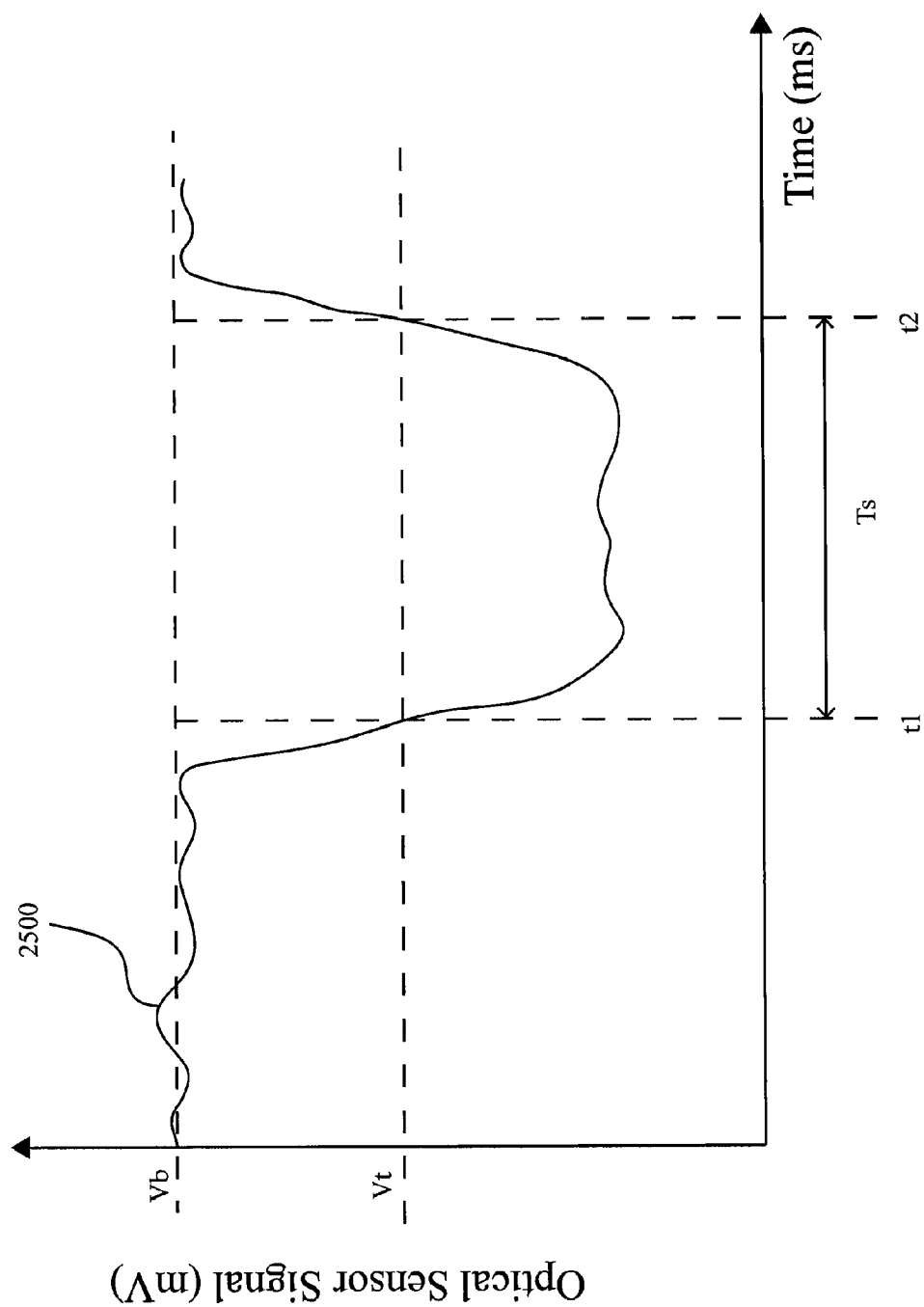
FIG. 43 illustrates an optical stalk sensor signal.
Figure 44:
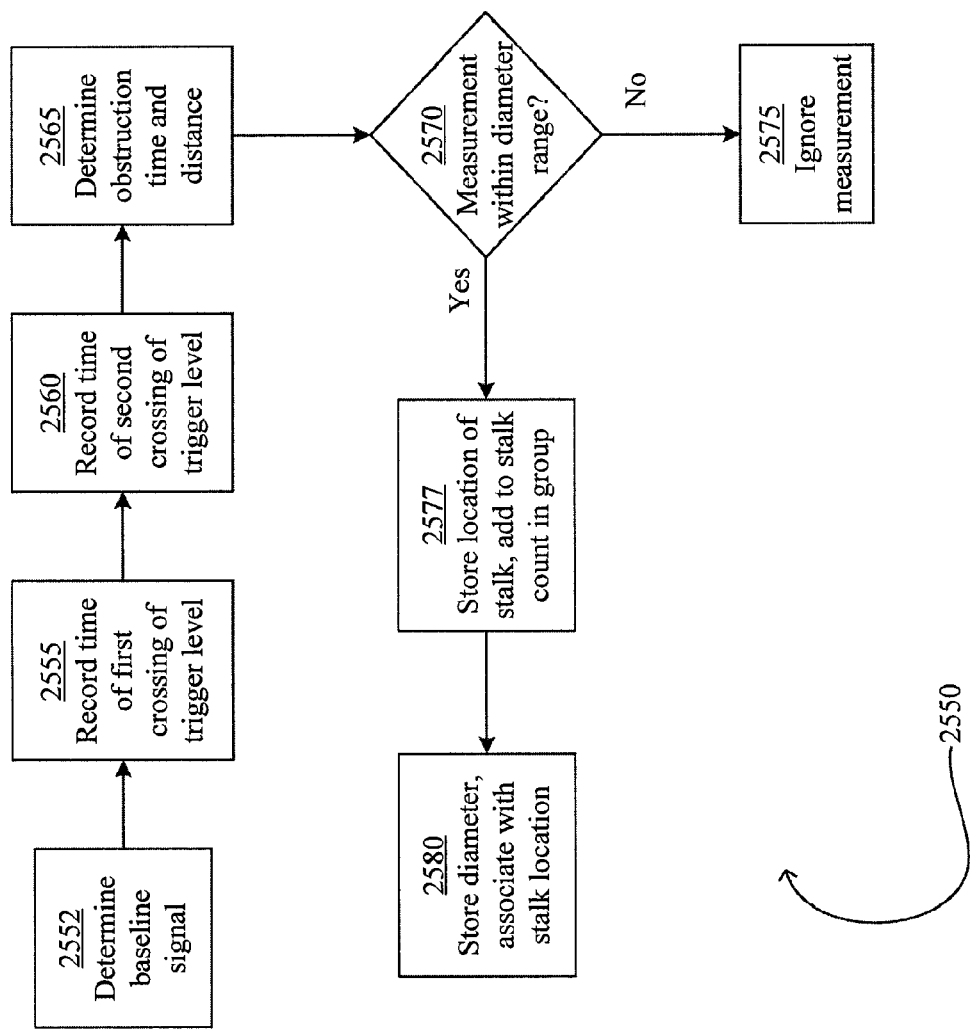
FIG. 44 illustrates an embodiment of a process for using a non-contact sensor to measure stalk diameter.

Turning to FIG. 43, a signal 2500 from the receiver 300b' over time is illustrated during a period in which a stalk has passed through the optical stalk sensor 300'. A baseline Vb of the signal 2500 is obtained when unobstructed light travels between the emitter 300a' and receiver 300b'. Turning to FIG. 44, a process 2550 for measuring a stalk diameter is illustrated. At step 2552, the monitor board 250 preferably determines the value of the baseline signal 2552. The baseline Vb may be a value measured while the combine speed is in excess of likely harvesting speed or may be pre-loaded into the memory of the monitor board 250. At step 2555, the monitor board 250 preferably records the time t1 of a first signal crossing of a trigger value Vt. The trigger value Vt may be a multiple of the baseline signal, e.g., 0.6Vb. At step 2560, the monitor board 250 preferably records the time t2 of a second signal crossing of the trigger value Vt. At step 2565, the monitor board 250 preferably determines the period Ts of the obstruction and preferably determines the distance traveled during the obstruction, either by integrating the combine speed signal from t1 to t2 or by determining the difference in position reported by the receiver 52 from t1 to t2. At step 2570, the monitor board 250 preferably determines whether the measured distance is within a diameter range potentially corresponding to a stalk, e.g., 0.75 cm to 3.0 cm. If the measurement is outside the predefined range, then at step 2575 the measurement is discarded. If the measurement is within the predefined range, then at step 2577 the monitor board preferably stores the stalk location (preferably corresponding to the midpoint between the positions of the stalk sensor 300' at times t1 and t2) and increases a stalk count stored in the memory 204 by one. It should be appreciated that the monitor board 250 may use the stalk count independently of the diameter measurement in order to determine such values as the emergence and actual population values described herein. At step 2580 the stalk diameter is preferably stored and associated with the stalk location.

It should be appreciated that the methods described with respect to FIG. 44 may be used with other stalk sensors replacing the optical stalk measurement device 300'. For example, a capacitive sensor such as that disclosed in U.S. Pat. No. 6,073,427 may be used to obtain a signal proportional to the capacitance of a sensing region, thus indicating the presence of stalks adjacent to the sensor.

As discussed above with respect to FIG. 26, the stalk measurement system 100 may record stalk diameter data for individual stalk blocks 1822. Referring to 5, in other embodiments the stalk measurement system may record stalk diameter data in row blocks 1860 including multiple stalks. The stalk measurement system 300 preferably associates a stalk diameter value to each row block 1860 corresponding to the average diameter of the stalks 25 contained within the row block. The row blocks are preferably created at regular time intervals (e.g., 1 Hertz) such that the length Lr of the row blocks 1860 varies with the speed of the combine 10. The calculations described herein using stalk blocks may instead be performed using row blocks.

Figure 41:
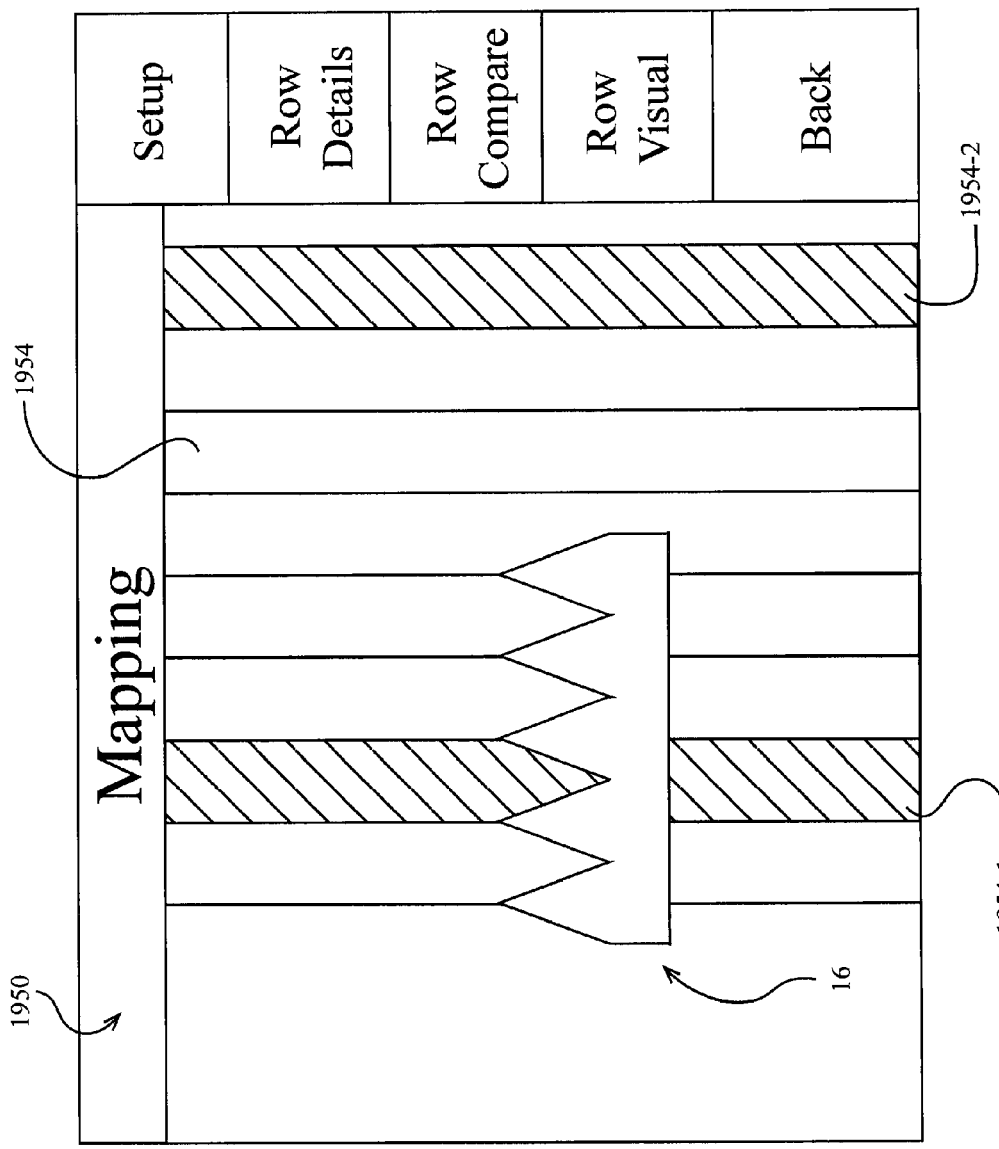
FIG. 41 illustrates an embodiment of a harvest map screen displaying planting data indicating rows affected by tire compaction.

As discussed above with respect to FIG. 31, a correlation between yield and different planting process variables may be determined by plotting yield against each variable. In some embodiments this may be achieved by plotting a variable for one planter row against the yield for that row, or by plotting a variable for all planter rows against yield for all planter rows. In alternative embodiments, particularly where a variable affects specific known rows, the correlation between yield and the variable may be accomplished by comparing yields for rows affected by the variable to yields for rows unaffected by the variable. As illustrated in FIG. 41, the harvest monitor may display a harvesting map screen 1950 in which the corn head 16 is illustrated traveling over a planting map consisting of planted rows 1954. The cross-hatched rows designated 1954-1 and 1954-2 represent "pinch rows" planted between two planter tires. Tire compaction on both sides of a planted row has been empirically shown to affect yield in the row. The identity of the pinch rows is preferably recorded in the planting file provided by the operator in the setup phase described herein. Whenever a combine row unit (e.g., the third row unit in FIG. 41) harvests a pinch row, the average yield Ypr from the pinch rows is recorded. When the combine has harvested all or a portion of a field resulting in a total yield Yt, the harvest monitor 200 preferably calculates the yield loss Yd associated with tire tracks by subtracting Ypr from Yt.

It should be appreciated in light of the instant disclosure that although correlation of yield with planting process variables recorded in planting files is discussed herein, similar methods could be used to correlate yield with variables related to post- or pre-planting cultivation activities. For example, rows affected by tire compaction from post-planting field activity could be identified in a cultivation activity file such that overall yield could be compared to yield from rows affected by post-planting tire compaction.

The foregoing description is presented to enable one of ordinary skill in the art to make and use the invention and is provided in the context of a patent application and its requirements. Various modifications to the preferred embodiment of the apparatus, and the general principles and features of the system and methods described herein will be readily apparent to those of skill in the art. Thus, the present invention is not to be limited to the embodiments of the apparatus, system and methods described above and illustrated in the drawing figures, but is to be accorded the widest scope consistent with the spirit and scope of the appended claims.

The invention claimed is:

1. A method of measuring stalk diameter as an agricultural combine traverses a field, comprising:
   measuring a quantity of grain harvested by the agricultural combine with a yield sensor;
   determining a yield value based on said quantity of grain;
   associating said yield value with a region of the field;
   moving a first stalk sensor associated with a row unit of the agricultural combine past a first stalk in the field, said first stalk sensor generating a first signal related to a position of said first stalk sensor relative to said first stalk;
   storing said first signal in memory;
   determining a first stalk diameter of said first stalk based on said first signal;
   generating a subsequent signal, said subsequent signal related to a position of said first stalk sensor relative to a subsequent stalk;
   storing said subsequent signal in memory;
   determining a subsequent stalk diameter of said subsequent stalk based on said subsequent signal;
   associating a subset of said yield value with a subset of said region of the field based on said first stalk diameter and said subsequent stalk diameter; and
   displaying a yield map associating a graphical representation of said subset of said region of the field with said subset of said yield value.

2. The method of claim 1, further comprising:
   recording a geo-referenced position of a global positioning receiver, said global positioning receiver disposed at a first offset from said first stalk sensor;
   determining a geo-referenced position of said first stalk based on said first offset; and
   storing in memory a first association.

3. The method of claim 2, further comprising:
   contacting the first stalk from a first side with a first feeler, said first feeler rotatably mounted to said first stalk sensor;
   contacting said first stalk from a second side with a second feeler, said second feeler rotatably mounted to said first stalk sensor;
   measuring a first displacement of said first feeler;
   measuring a second displacement of said second feeler; and
   determining said first stalk diameter based on said first displacement and said second displacement.

4. The method of claim 2, further comprising:
   generating an electromagnetic field;
   detecting said electromagnetic field;
   intercepting said electromagnetic field with said first stalk over a time interval; and
   determining said first stalk diameter based on speed of the agricultural combine during said time interval or a position of the agricultural combine during said time interval.

5. The method of claim 2, further comprising:
   moving a second stalk sensor associated with a second row unit of the agricultural combine past a second stalk in the field, said second stalk sensor generating a second signal related to a position of said second stalk sensor relative to said second stalk;
   storing said second signal in memory;
   determining a second stalk diameter of said second stalk based on said second signal;
   determining a geo-referenced position of said second stalk based on a second offset from said second stalk sensor to said global positioning receiver;
   storing in memory a second association between said second stalk diameter and said geo-referenced position of said second stalk;
   measuring a quantity of grain harvested by the agricultural combine with a yield sensor;
   determining a yield value based on said quantity of grain;
   associating said yield value with a region of the field;
   storing in memory a partial allotment of said yield value to a subset of said region of the field based on said first stalk diameter, said subset of said region including said geo-referenced position of said first stalk; and
   displaying a yield map associating a graphical representation of said subset of said region of the field with said partial allotment of said yield value.

6. The method of claim 2, further comprising:
displaying harvest data to a user on a display screen located in the agricultural combine, said harvest data based on said first stalk diameter.

7. The method of claim 6, wherein said harvest data includes said first stalk diameter.

8. The method of claim 6, wherein said harvest data includes a portion of yield attributable to the row unit associated with said first stalk sensor.

9. The method of claim 6, wherein said harvest data includes an economic loss value.

10. The method of claim 6, wherein said harvest data includes a statistical variation in said determined stalk diameters.

11. A method of measuring a diameter of a stalk processed by an agricultural combine as the agricultural combine traverses a field, comprising:
providing a stalk sensor associated with a row unit of the agricultural combine;
moving said stalk sensor past a stalk in the field;
generating a signal using said stalk sensor, said signal related to a position of the stalk sensor relative to said stalk;
storing said signal in memory;
adding to a stalk count based on said signal, said stalk count representing a number of stalks harvested by the row unit during a sampling period; and
displaying harvest data to a user in the agricultural combine, said harvest data based on said stalk count.

12. The method of claim 11,
wherein said harvest data is related to the number of stalks harvested by the agricultural combine;
wherein the method further comprises: displaying an as-planted population value recorded during planting to the user in the agricultural combine, wherein said harvest data includes an actual population.

13. The method of claim 11, wherein said harvest data includes an emergence value.

14. The method of claim 11, further comprising:
displaying an indication of a planter row that planted the stalks being harvested by the row unit of the agricultural combine.

15. A stalk sensor system for use with an agricultural combine harvester while the agricultural combine harvester traverses a field, comprising:
a first stalk sensor associated with a first combine row unit;
a second stalk sensor associated with a second combine row unit;
a yield sensor configured to generate a signal related to a quantity of grain harvested by the agricultural combine harvester;
a global positioning receiver mounted to the agricultural combine harvester and configured to generate a position signal, said position signal related to a position of the agricultural combine harvester; and
processing circuitry in electrical communication with said first stalk sensor, said second stalk sensor, said yield sensor and said global positioning receiver,
said processing circuitry configured to determine stalk diameter measurements and stalk measurement locations based on signals generated by said first and second stalk sensors,
said processing circuitry further configured to generate a map, said map associating said stalk measurement locations with said stalk diameter measurements.

16. The stalk sensor system of claim 15, wherein said processing circuitry is further configured to calculate a harvest metric based on said stalk diameter measurements, and further comprising:
a monitor in electrical communication with said processing circuitry, said monitor having a graphical user interface, said monitor configured to display said harvest metric to a user in the agricultural combine harvester.

17. The stalk sensor system of claim 15, wherein said stalk measurement locations of said first stalk sensor are based on a first offset between said global positioning receiver to said first stalk sensor and said stalk measurement locations of said second stalk sensor are based on a second offset between said global positioning receiver to said second stalk sensor, wherein said first stalk sensor includes a feeler disposed to contact stalks passing through the first combine row unit, and wherein said first stalk sensor is configured to generate a displacement signal related to a displacement of said feeler.

18. The stalk sensor system of claim 15, wherein said first stalk sensor includes an electromagnetic field transmitter and an electromagnetic field detector, said electromagnetic field transmitter disposed to generate an electromagnetic field intercepting a path traveled by stalks entering the first combine row unit.

19. The stalk sensor system of claim 15, wherein said processing circuitry is configured to associate a yield value with a region of the field, wherein said yield value is based on said stalk diameter measurements, said stalk diameter measurements associated with said region of the field, and wherein said yield value is based on a correlation between measurements of stalk diameters and yield.

20. The stalk sensor system of claim 19, further comprising:
a monitor in electrical communication with said processing circuitry, said monitor having a graphical user interface, wherein said monitor is configured to display a yield map based on said yield value.

* * * * *